(12) United States Patent
Av-Gay et al.

(10) Patent No.: US 11,890,421 B2
(45) Date of Patent: Feb. 6, 2024

(54) METHODS FOR POTENTIATING ANTIMICROBIAL AGENTS

(71) Applicant: BEYOND AIR LTD, Rehovot (IL)

(72) Inventors: Yossef Av-Gay, Vancouver (CA); David Greenberg, Omer (IL); Asher Tal, Meytar (IL)

(73) Assignee: BEYOND AIR LTD, Rehovot (IL)

( * ) Notice: Subject to any disclaimer, the term of this patent is extended or adjusted under 35 U.S.C. 154(b) by 1032 days.

(21) Appl. No.: 16/787,921

(22) Filed: Feb. 11, 2020

(65) Prior Publication Data

US 2020/0246573 A1 Aug. 6, 2020

Related U.S. Application Data

(63) Continuation of application No. 15/758,108, filed as application No. PCT/IB2016/001447 on Sep. 9, 2016, now abandoned.

(Continued)

(51) Int. Cl.
*A61M 16/10* (2006.01)
*A61M 16/12* (2006.01)
(Continued)

(52) U.S. Cl.
CPC ............ *A61M 16/12* (2013.01); *A61K 33/00* (2013.01); *A61K 45/06* (2013.01); *A61P 31/00* (2018.01);
(Continued)

(58) Field of Classification Search
CPC .............. A61B 90/40; A61F 13/00068; A61F 13/0206; A61F 13/0216; A61F 2007/0059; A61F 2013/00357; A61H 33/14; A61H 9/0057; A61K 2300/00; A61K 31/131; A61K 31/155; A61K 31/198; A61K 31/21; A61K 33/00; A61K 9/0078; A61M 1/75;
(Continued)

(56) References Cited

U.S. PATENT DOCUMENTS 5,873,359 A * 2/1999 Zapol ................ A61M 15/0086
128/200.14
6,369,050 B1 4/2002 Tawara et al.
(Continued)

FOREIGN PATENT DOCUMENTS

WO 2006125262 A1 11/2006
WO 2010048724 A1 5/2010

OTHER PUBLICATIONS

Tal, A. et al., "Intermittent, High-Dose Nitric Oxide Inhalation Therapy for Hospitalized Infants 1-9 With Bronchiolitis: A Double-Blinded, Randomized Controlled Trial", American Thoracic Society 2015 Conference Abstracts, May 18, 2015.
(Continued)

*Primary Examiner* — Annette Dixon
(74) *Attorney, Agent, or Firm* — ELMORE PATENT LAW GROUP, PC; JOSEPH C. ZUCCHERO

(57) ABSTRACT

The invention provides a method of treating a subject having a medical condition associated with a pathogenic microorganism, the method comprising administering to said subject a potentiating effective amount of nitric oxide; and administering to said subject a therapeutically effective amount of an antimicrobial agent, wherein said antimicrobial agent is other than said nitric oxide.

18 Claims, 12 Drawing Sheets

Related U.S. Application Data

(60) Provisional application No. 62/220,321, filed on Sep. 18, 2015, provisional application No. 62/215,809, filed on Sep. 9, 2015.

(51) Int. Cl.
    *A61K 33/00*    (2006.01)
    *A61P 31/00*    (2006.01)
    *A61K 45/06*    (2006.01)
    *A61B 5/083*    (2006.01)
    *A61B 5/145*    (2006.01)

(52) U.S. Cl.
    CPC ......... *A61B 5/0833* (2013.01); *A61B 5/14507* (2013.01); *A61M 2202/0007* (2013.01); *A61M 2202/0275* (2013.01)

(58) Field of Classification Search
    CPC .......... A61M 1/77; A61M 1/772; A61M 1/85; A61M 1/915; A61M 1/916; A61M 1/92; A61M 1/94; A61M 1/96; A61M 13/003; A61M 15/00; A61M 15/0086; A61M 15/009; A61M 2202/0208; A61M 2202/0275; A61M 2202/064; A61M 2205/3653; A61M 2205/368; A61M 27/00; A61M 3/0204; A61M 3/0212; A61M 3/0229; A61M 35/30; A61P 11/00; A61P 11/08; A61P 43/00; A61P 9/12
    See application file for complete search history.

(56) References Cited

U.S. PATENT DOCUMENTS

| | | | | |
|---|---|---|---|---|
| 7,753,894 | B2 * | 7/2010 | Blott | ...... A61M 1/96 604/320 |
| 7,794,450 | B2 * | 9/2010 | Blott | ...... A61M 1/92 604/320 |
| 2002/0182162 | A1 | 12/2002 | Shahinpoor et al. | |
| 2004/0037897 | A1 | 2/2004 | Benjamin et al. | |
| 2007/0144515 | A1 | 6/2007 | Stenzler et al. | |
| 2008/0167603 | A1 * | 7/2008 | Stenzler | ...... A61M 13/003 604/26 |
| 2015/0034084 | A1 | 2/2015 | Av-Gay et al. | |

OTHER PUBLICATIONS

Bang, C. D. et al., "The antibacterial effect of nitric oxide against ESBL-producing uropathogenic *E. coli* is improved by combination with miconazole and polymyxin B nonapeptide", BMC Microbiology, 14(65), 2014, 65-73.

Barraud, et al., "Cephalosporin-3'-diazeniumdiolates: Targeted NO-Donor Prodrugs for Dispersing Bacterial Biofilms", Angewandte Chemie, vol. 51, 2012, 9057-9060.

Barraud, et al., "Nitric Oxide: A Key Mediator of Biofilm Dispersal with Applications in Infectious Diseases", Current Pharmaceutical Design, vol. 21, 2015, 31-42.

Coban, A. Y. et al., "The Effect of Nitric Oxide Combined with Fluoroquinolones against *Salmonella enterica* Serovar Typhimurium in Vitro", Memórias do Instituto Oswaldo Cruz, vol. 98, No. 3, 2003, 419-423.

Fang, F. C. "Mechanisms of Nitric Oxide-related Antimicrobial Activity", Journal of Clinical Investigation, vol. 99, No. 12, 1997, 2818-2825.

Miller, C. C. et al., "Gaseous nitric oxide bactericidal activity retained during intermittent high-dose short duration exposure", Nitric Oxide: Biology and Chemistry, Academic Press, Amsterdam, NL, vol. 20(1), Feb. 1, 2009, 16-23.

Schairer, et al., "The potential of nitric oxide releasing therapies as antimicrobial agents", Virulence, vol. 3, No. 3, 2012, 271-279.

Zaitseva, et al., "Effect of nitrofurans and NO generators on biofilm formation by Pseudomonas aeruginosa PAO1 and Burkholderia cenocepacia 370", Research in Microbiology, vol. 160, 2009, 353-357.

* cited by examiner

A.

B.

C.

D.

A.

B.

C.

D.

METHODS FOR POTENTIATING ANTIMICROBIAL AGENTS

CROSS REFERENCE TO RELATED APPLICATIONS

This application is a continuation of U.S. application Ser. No. 15/758,108, filed on Mar. 7, 2018, which is a US National stage entry of International Application No. PCT/IB2016/001447, which designated the United States and was filed on Sep. 9, 2016, published in English, which claims priority to U.S. Provisional Patent Application Ser. No. 62/215,809, filed on Sep. 9, 2015, and U.S. Provisional Patent Application Ser. No. 62/220,321, filed on Sep. 18, 2015, the entire contents of which are incorporated by reference in their entirety.

FIELD OF THE INVENTION

Some embodiments relate to therapies, methods and devices for treating bronchiolitis in infants. Some embodiment relate to therapies, methods and devices for potentiating antimicrobial agents and/or sensitizing antimicrobial agent-resistant microorganisms to an antimicrobial treatment.

SUMMARY

The following embodiments and aspects thereof are described and illustrated in conjunction with systems, tools and methods which are meant to be exemplary and illustrative, not limiting in scope.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

According to some embodiments, the present invention is a method for treating bronchiolitis in an infant in need thereof, wherein the wherein the method comprises repeatedly administering to the infant a gas mixture comprising nitric oxide at a concentration from about 144 to about 176 ppm for a first period of time, followed by a gas mixture containing no nitric oxide for a second period of time, wherein the administration is repeated for a time sufficient to: a) reduce the length of time of hospitalization required to achieve oxygen saturation greater than or equal to 92% in room air, compared an infant that is not subjected to the repeated administration of nitric oxide; b) reduce the length of time of hospitalization required to achieve a clinical score of less than or equal to 5, compared an infant that is not subjected to the repeated administration of nitric oxide; c) reduce the length of time of hospitalization required to be discharged, compared an infant that is not subjected to the repeated administration of nitric oxide; or d) any combination thereof.

In some embodiments, the first time period is 30 minutes and the second time period is from about 3 to about 5 hours.

In some embodiments, the administration is repeated six times per day.

In some embodiments, the nitric oxide is repeatedly administered for a period of time from about one day to three weeks.

In some embodiments, the nitric oxide is repeatedly administered for five days.

In some embodiments, the method further comprises monitoring at least one on-site oximetric parameter in the infant, the on-site parameter being selected from the group consisting of: oxyhemoglobin saturation ($SpO_2$); methemoglobin (SpMet); perfusion index (PI); respiration rate (RRa); oxyhemoglobin saturation (SpO2); total hemoglobin (SpHb); carboxyhemoglobin (SpCO); methemoglobin (SpMet); oxygen content (SpOC); and pleth variability index (PVI).

In some embodiments, the method further comprises monitoring at least one additional on-site spirometric parameter in the infant, the at least one additional on-site parameter being selected from the group consisting of: forced expiratory volume (FEV1); maximum mid-expiratory flow (MMEF); diffusing capacity of the lung for carbon monoxide (DLCO); forced vital capacity (FVC); total lung capacity (TLC); and residual volume (RV).

In some embodiments, the method further comprises monitoring at least one on-site parameter in the gas mixture inhaled by the infant, the on-site parameter being selected from the group consisting of: end tidal $CO_2$ ($ETCO_2$); nitrogen dioxide ($NO_2$), nitric oxide (NO); serum nitrite/nitrate; and fraction of inspired oxygen ($FiO_2$).

In some embodiments, the method further comprises monitoring at least one off-site bodily fluid parameter in the infant, the parameter being selected from the group consisting of: a bacterial and/or fungal load; urine nitrite; blood methemoglobin; blood pH; a coagulation factor; blood hemoglobin; hematocrit ratio; red blood cell count; white blood cell count; platelet count; vascular endothelial activation factor; renal function; an electrolyte; a pregnancy hormone; serum creatinine; and liver function.

According to some embodiments of an aspect of the present invention, there is provided a method of treating a subject having a medical condition associated with a pathogenic microorganism, the method includes:
  (i) administering to the subject a potentiating effective amount of nitric oxide; and
  (ii) administering to the subject a therapeutically effective amount of an antimicrobial agent, wherein the antimicrobial agent is other than the nitric oxide.

In some embodiments, the potentiating effective amount is lower than a therapeutically effective amount of the nitric oxide with respect to the pathogenic microorganism.

In some embodiments, the potentiating effective amount is lower than 1 MIC unit of nitric oxide with respect to the pathogenic microorganism.

In some embodiments, the pathogenic microorganism exhibits a resistance to the antimicrobial agent prior to the administering of the potentiating effective amount of nitric oxide.

In some embodiments, the resistance to the pathogenic microorganism is innate or acquired.

In some embodiments, the antimicrobial agent is inactive when used against the pathogenic microorganism per se (without administration of NO).

According to some embodiments of an aspect of the present invention, there is provided a method of treating a subject having a medical condition associated with a pathogenic microorganism in which an antimicrobial resistance has been uncovered following treating the subject with the antimicrobial agent, the method is effected by:
  (i) administering to the subject, following a treatment with the antimicrobial agent and uncovering antimicrobial resistance, a re-sensitizing effective amount of nitric oxide; and
  (ii) administering to the subject a therapeutically effective amount of the antimicrobial agent, wherein the antimicrobial agent is other than said nitric oxide and the re-sensitizing effective amount of nitric oxide is lower than a therapeutically effective amount of nitric oxide with respect to the microorganism.

According to some embodiments of an aspect of the present invention, there is provided a method for sensitizing or re-sensitizing a microorganism to an antimicrobial agent, includes:
  (i) contacting the microorganism with a sensitizing or re-sensitizing effective amount of nitric oxide; and
  (ii) contacting the microorganism with a therapeutically effective amount of the antimicrobial agent, wherein the antimicrobial agent is other than the nitric oxide.

In some embodiments, the sensitizing or re-sensitizing effective amount is lower than a therapeutically effective amount of the nitric oxide with respect to the pathogenic microorganism.

In some embodiments, the sensitizing or re-sensitizing effective amount is lower than 1 MIC unit of nitric oxide with respect to the pathogenic microorganism.

In some embodiments, contacting the microorganism with the nitric oxide includes administering to a subject having a medical condition associated with the microorganism, the sensitizing or re-sensitizing effective amount of the nitric oxide.

In some embodiments, the method presented herein further includes administering to the subject the antimicrobial agent.

In some embodiments, (i) is effected prior to (ii).

In some embodiments, (ii) is effected prior to (i).

In some embodiments, (i) is effected concomitantly with (ii).

According to some embodiments of an aspect of the present invention, there is provided a pharmaceutical composition which includes a sensitizing or re-sensitizing effective amount of nitric oxide, and a therapeutically effective amount of an antimicrobial agent, and at least one pharmaceutically acceptable carrier.

In some embodiments, the pharmaceutical composition presented herein is in a multi-part form wherein the nitric oxide is in a first part and the antimicrobial agent is in a second part.

According to some embodiments of an aspect of the present invention, there is provided a pharmaceutical composition unit dosage form includes a therapeutically effective amount of an antimicrobial agent in a first unit dosage form, and a sensitizing or re-sensitizing effective amount of nitric oxide in a second unit dosage form, the sensitizing or re-sensitizing effective amount being such that effects a sensitization or re-sensitization of a pathogenic microorganism to the antimicrobial agent, wherein the sensitizing or re-sensitizing effective amount is lower than a therapeutically effective amount of nitric oxide with respect to the pathogenic microorganism.

According to some embodiments of an aspect of the present invention, there is provided a pharmaceutical kit includes packaging material and a therapeutically effective amount of an antimicrobial agent packaged in said packaging material, the kit being labeled for treating a medical condition associated with a pathogenic microorganism and/or for sensitizing or re-sensitizing a pathogenic microorganism to the antimicrobial agent upon co-administering to a treated subject a sensitizing or re-sensitizing effective amount of nitric oxide.

In some embodiments, the kit further includes a sensitizing or re-sensitizing effective amount of nitric oxide, such that the antimicrobial agent and the nitric oxide are packaged individually within the kit.

In some embodiments of the method, composition, unit dosage form or kit presented herein, the therapeutically effective amount of the antimicrobial agent is lower than a 1 MIC with respect to the pathogenic microorganism.

In some embodiments of the method, composition, unit dosage form or kit presented herein, nitric oxide is administered or contacted in a form of gaseous nitric oxide or a nitric oxide releasing compound.

In some embodiments of the method, composition, unit dosage form or kit presented herein, nitric oxide is administered or contacted with the microorganism by inhalation.

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention. The figures are listed below.

MetHb levels over time for the 1$^{st}$ treatment (ITT, N=43). Panel B: Mean (±SE) pre-treatment and end of treatment metHb levels by treatment number for the no treatment group (ITT). ITT=intent-to-treat subgroup; MetHb=methemoglobin; N=number of infants at each treatment number; SE=standard error.

Figure 4:
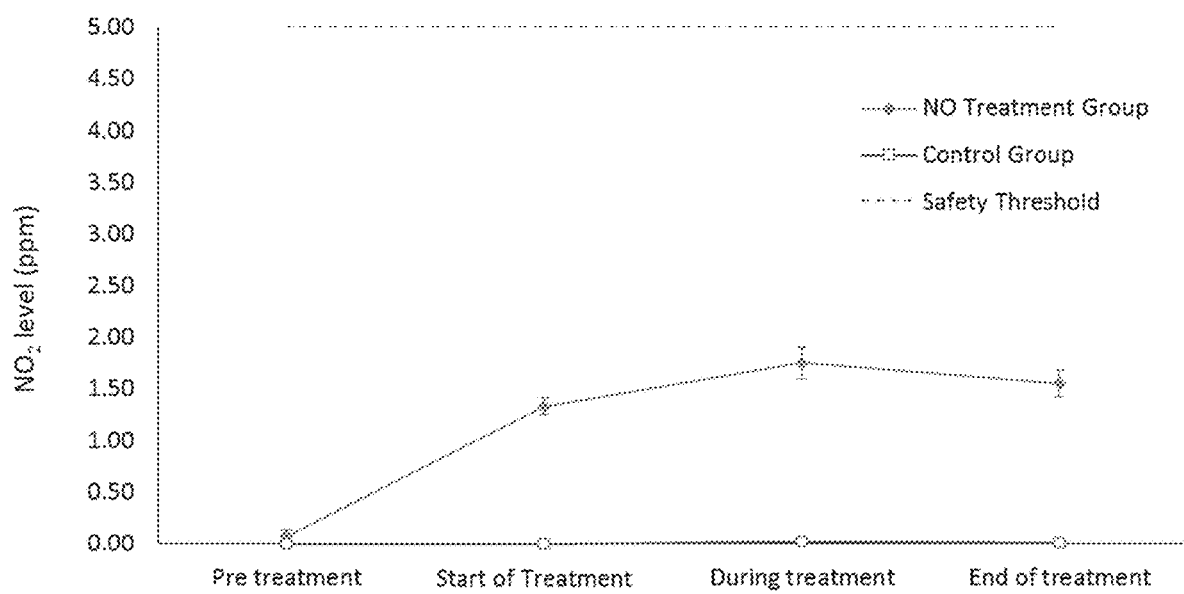

FIG. 4 shows $NO_2$ levels in the first administration of NO in infants treated according to some embodiments.

Figure 5:
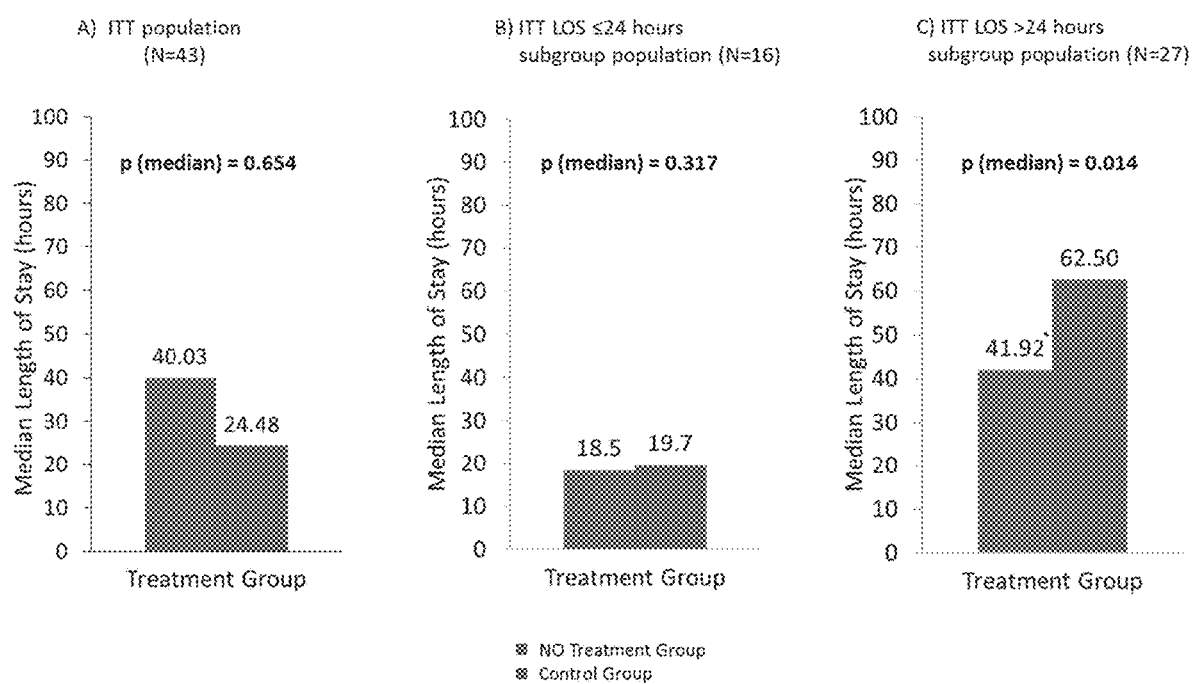

FIG. 5 shows the observed median length of stay (LOS) in infants treated according to some embodiments, according to treatment and subgroup. Panel A: ITT analyses (n=43). Panel B: ITT for LOS<24 hours (n=16). Panel C: ITT for LOS>24 hours (n=27).

Figure 6:
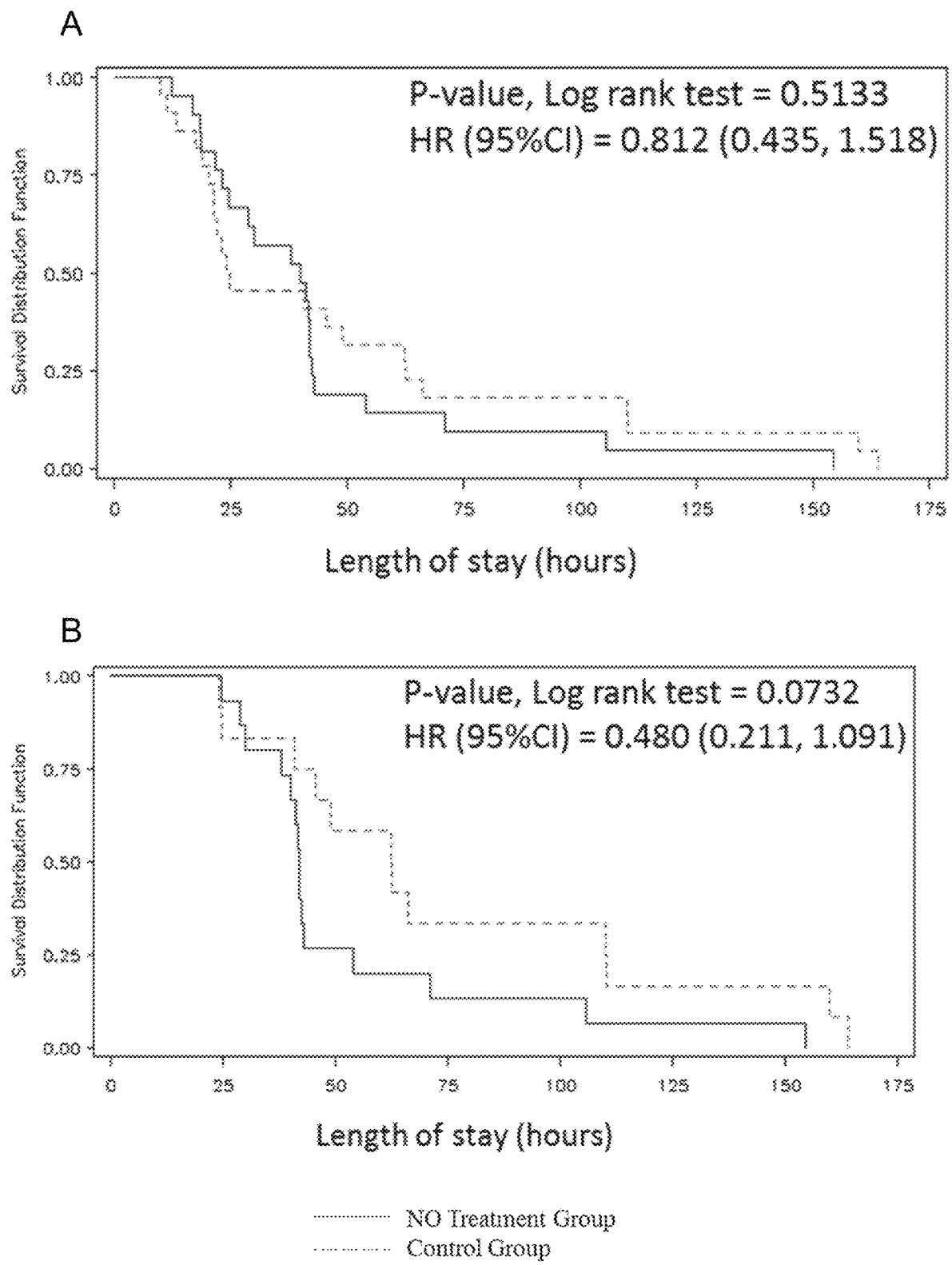
Figure 6:
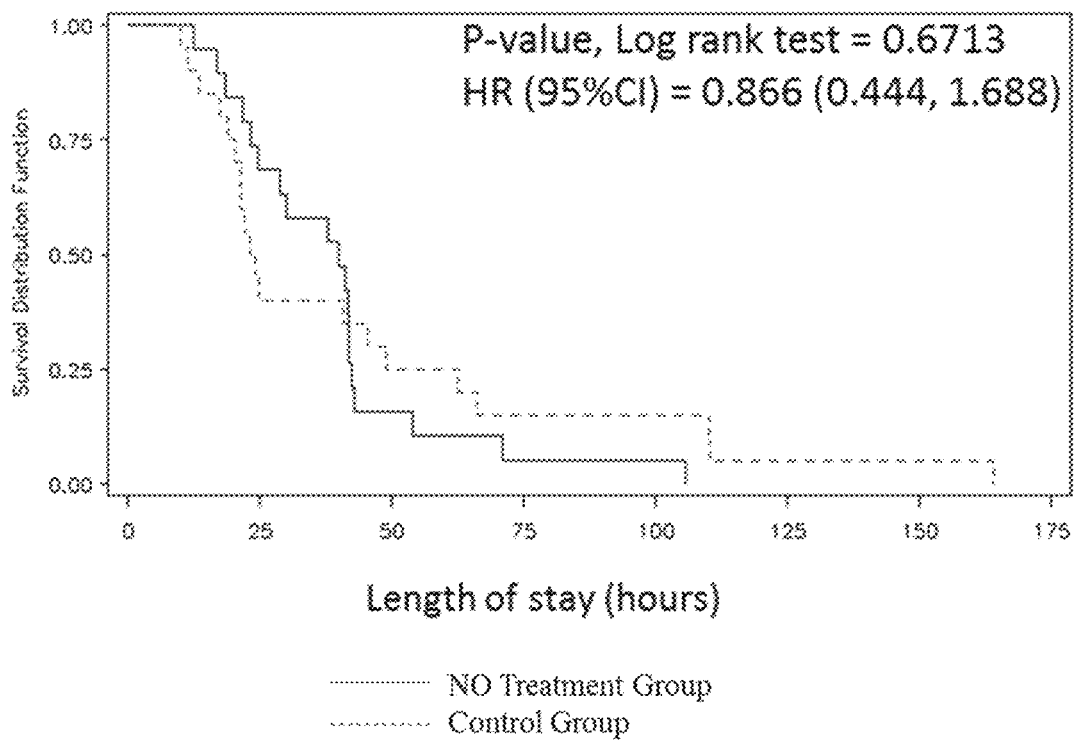
Figure 6:
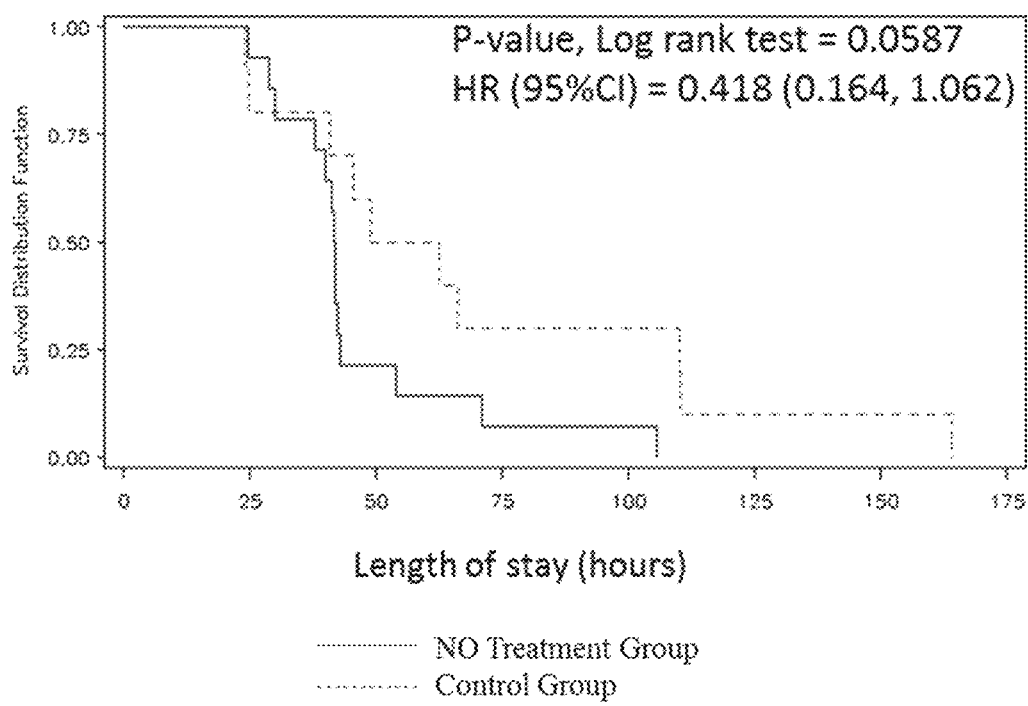

FIG. 6 shows Kaplan-Meier analysis of LOS in infants treated according to some embodiments, according to treatment and subgroup (ITT and PP). Panel A: Time to ready for discharge, ITT (n=43). Panel B: Time to ready for discharge LOS>24 hours subgroup (n=27). Panel C: Time to ready for discharge, PP analyses (n=39). Panel D: Time to ready for discharge, PP for >24 hours (n=24).

Figure 7:
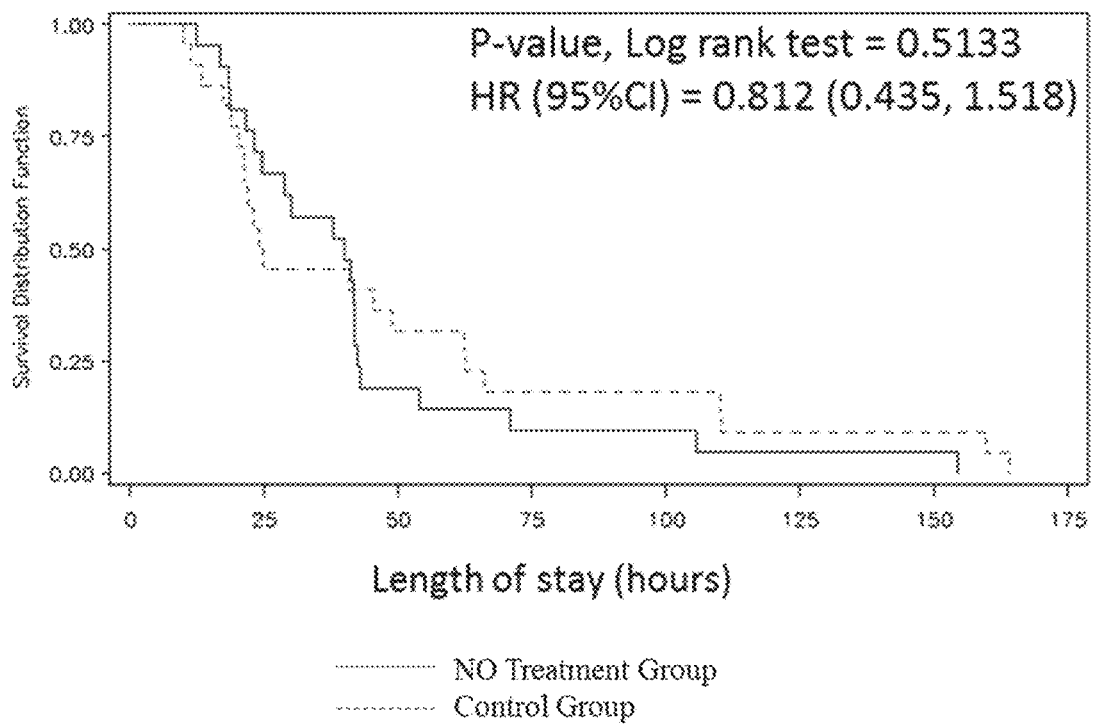
Figure 7:
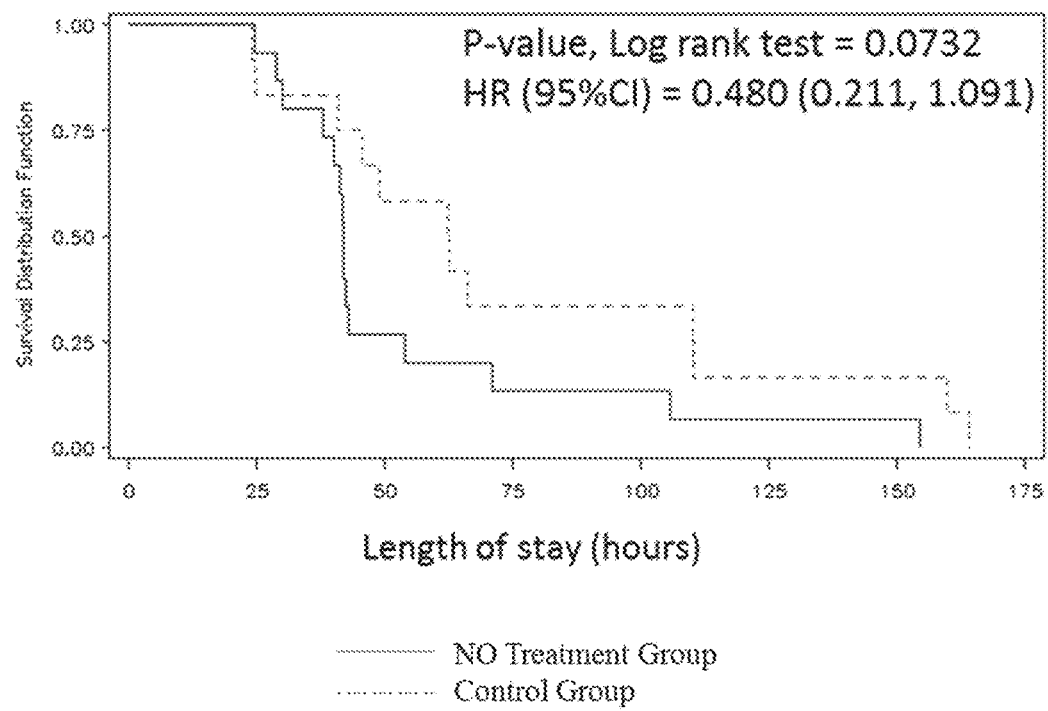
Figure 7:
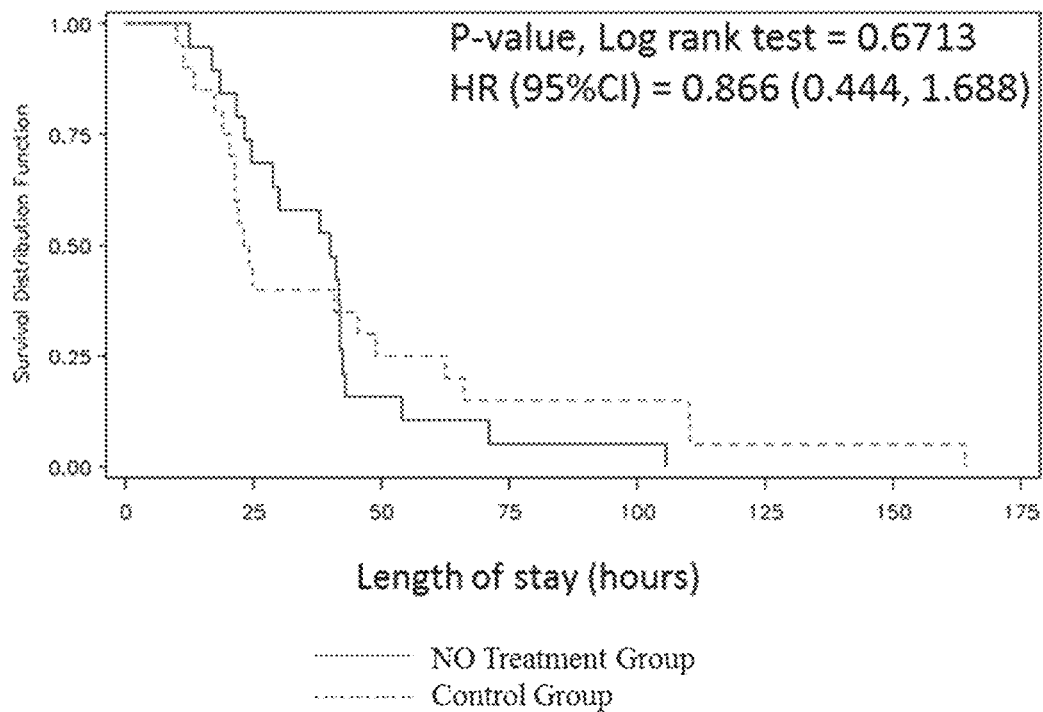
Figure 7:
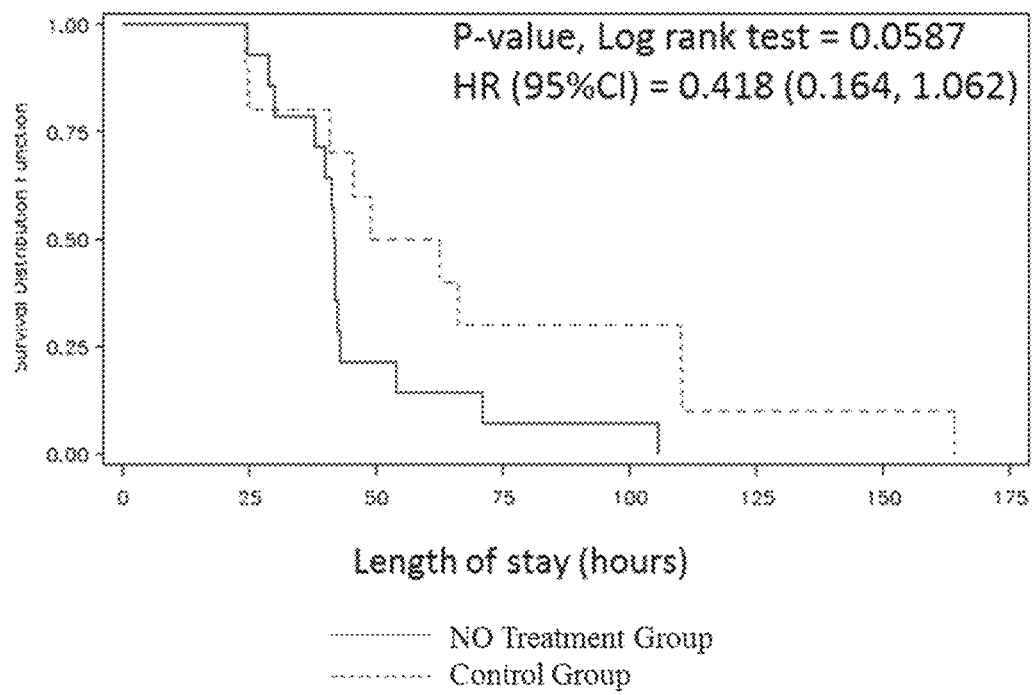

FIG. 7 shows Kaplan-Meier analysis of time to first sustained 92% saturation in infants treated according to some embodiments, according to treatment and subgroup (ITT and PP). Panel A: Time to 1$^{st}$ sustained $O_2$ Saturation, ITT population (n=42). One infant (control group) was excluded for analysis because the infant was admitted with $SpO_2$ of 92%. Panel B: Time to 1$^{st}$ sustained $O_2$ Saturation, ITT for LOS>24 hours (n=24). Panel C: Time to 1$^{st}$ sustained $O_2$ Saturation, PP population (n=38). One infant (control group) was excluded for analysis because the infant was admitted with $SpO_2$ of 92%. Panel D: Time to 1$^{st}$ sustained $O_2$ Saturation, PP for LOS>24 hours (n=24).

Figure 8:
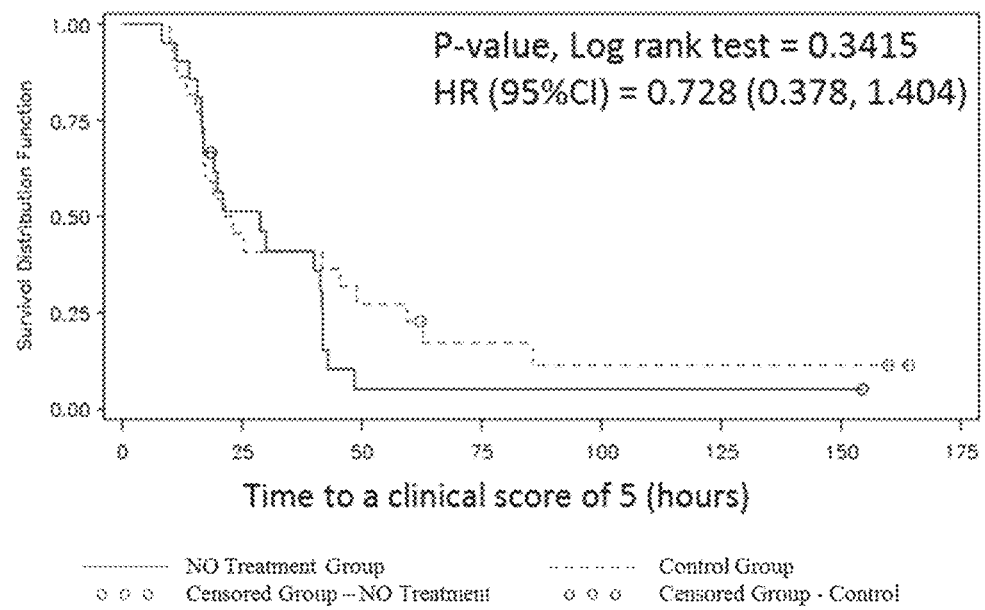
Figure 8:
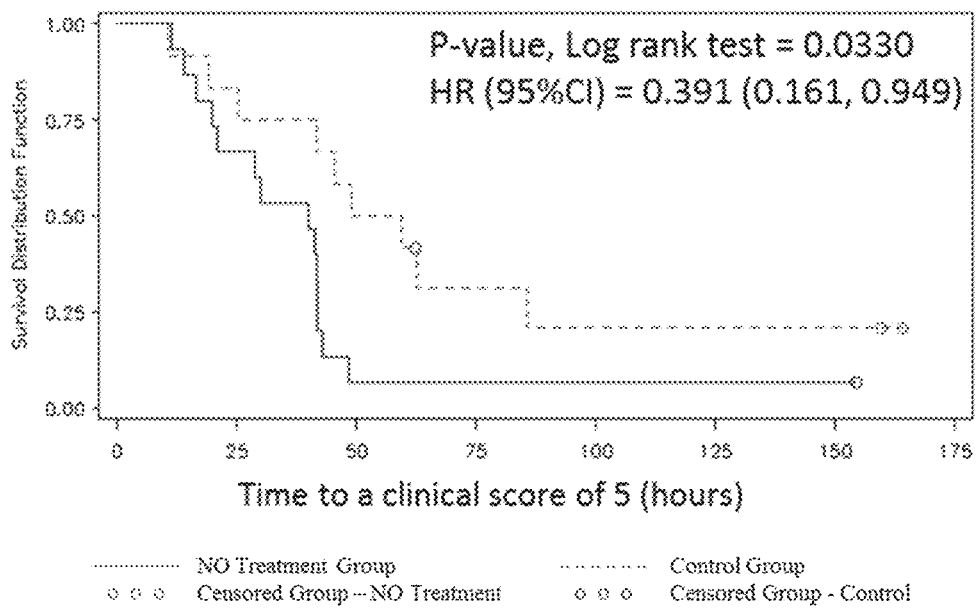
Figure 8:
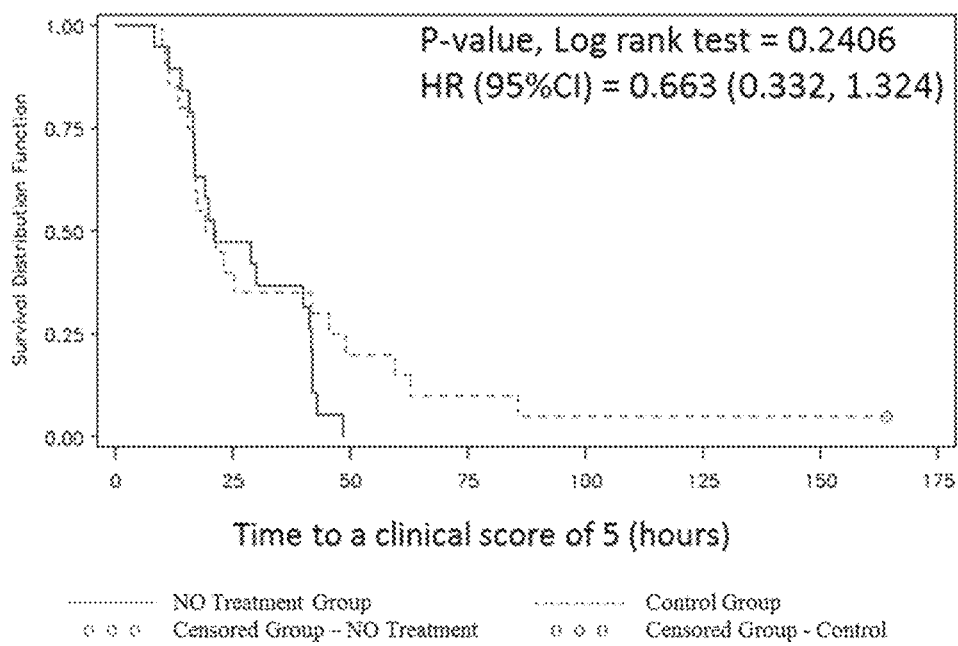
Figure 8:
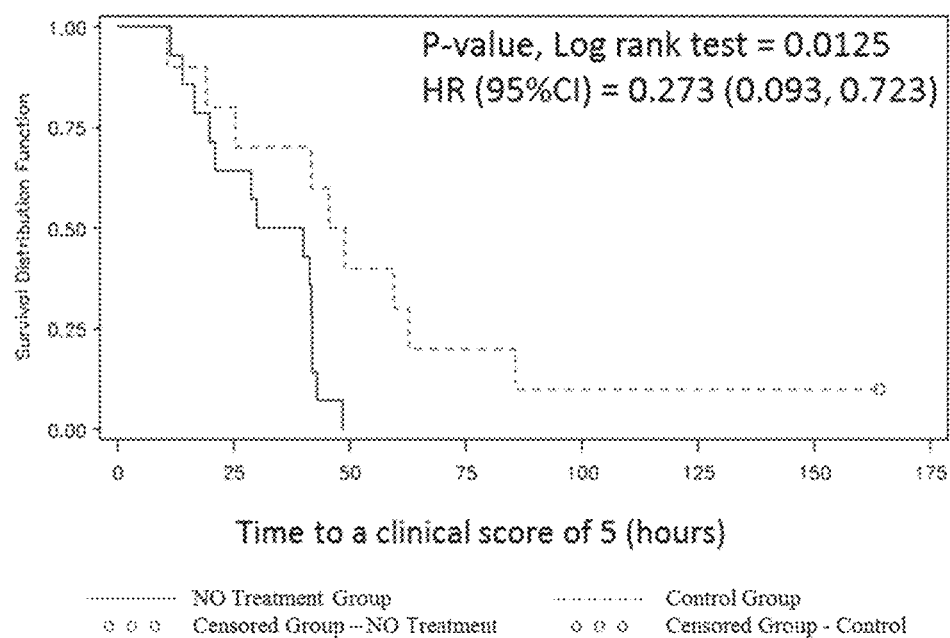

FIG. 8 shows Kaplan-Meier analysis of time to clinical score≤5 in infants treated according to some embodiments, according to treatment and subgroup (ITT and PP). Panel A: Time to achieve clinical score≤5, ITT population (n=43). Panel B: Time to achieve clinical score≤5, ITT for LOS>24 hours, (n=27). Panel C: Time to achieve clinical score≤5, PP population (n=39). Panel D: Time to achieve clinical score≤5, PP for LOS>24 hours (n=24).

Figure 9:
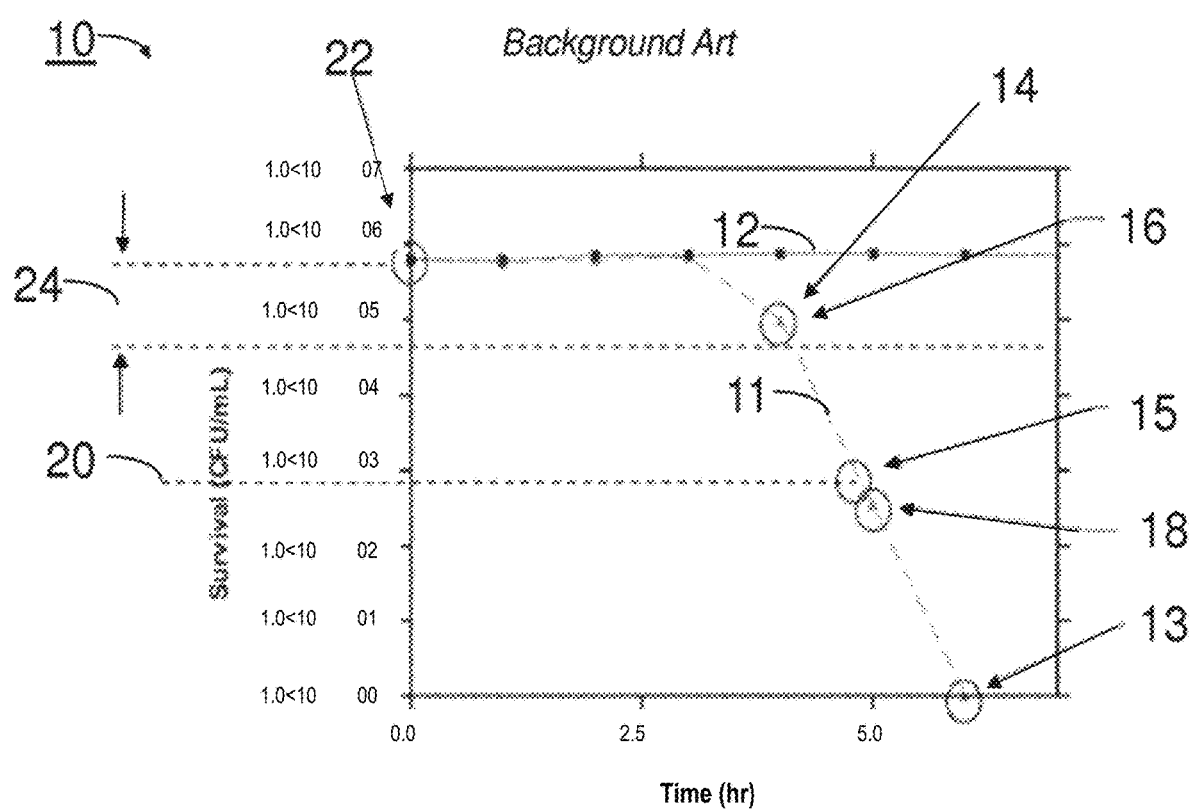

FIG. 9 shows a plot showing the antimicrobial activity of nitric oxide against *Serraia marcescens* as described in the background art, and demonstrating the latent period of antimicrobial activity, attributed to the time required to deplete the chemical defense mechanism of the microorganism.

DESCRIPTION

Treatment of Boronchiolitis: Inflammation is a primary or secondary response of the body to cell damage, infection or the presence of foreign matter. As a primary factor, inflammation is associated with a large number of diseases and disorders that may also cause system deterioration and failure and be the cause of secondary conditions, if goes untreated. Apart of the typical symptoms of inflammation, such as fever, swelling, pain and the likes, inflammation is also diagnosed by monitoring certain endogenous factors or inflammatory biomarkers, the level of which in the body is indicative of the severity and the stage of the inflammation.

Bronchiolitis is defined as an infection of the small airways. It is also the most common manifestation of acute lower respiratory infection (ALRI) in early infancy, and is the leading cause of global child mortality. Viral bronchiolitis is currently the most common reason for pediatric hospital admission in the US, accounting for almost 20% of all-cause infant hospitalizations. Viral etiology is the main cause, and among the respiratory viruses, respiratory syncytial virus (RSV) is believed to be the most important viral pathogen causing ALRI in young children. The disease is common mainly in the first year of life. The clinical signs and symptoms are consistent with hypoxia, difficulty breathing, coryza, poor feeding, cough, wheeze and crepitations on auscultation, and in some cases respiratory failure.

In one embodiment, the present invention administers nitric oxide to an infant, wherein the administration is short durations of high concentrations of nitric oxide, that improves lung function in infants suffering from bronchiolitis, while not causing lung injury or other signs of adverse effects.

Herein-throughout, whenever the term "nitric oxide" is used in the context of inhalation, it is to be understood that nitric oxide is inhaled in the gaseous state.

According to some embodiments of the present invention, there is provided a method of treating bronchiolitis in an infant in need thereof (e.g., an infant afflicted with bronchiolitis, or an infant diagnosed with bronchiolitis). Diagnosis of bronchiolitis can be effected by methods known in the art, including the methods described in the Examples section that follows.

The method as described herein comprises subjecting the infant to intermittent inhalation of a gaseous mixture that comprises nitric oxide, as described in any one of the embodiments pertaining to intermittent inhalation, and any combination thereof.

According to embodiments of the present invention, the method of treating bronchiolitis encompasses any beneficial therapeutic effect exhibited in a bronchiolitis patient, including, for example, amelioration of a symptom of bronchiolitis (e.g., improvement of a pulmonary function), amelioration of a medical condition associated with bronchiolitis (e.g., reduction of a microbial infection associated with bronchiolitis, reduction of the load of a pathogenic microorganism which is associated with bronchiolitis, reduction of inflammation), and reduction in the length of hospitalization of the infant.

In some embodiments, a method of treating bronchiolitis as described herein is regarded as a method of treating an infant suffering from bronchiolitis, and encompasses a method of ameliorating a symptom of bronchiolitis (e.g., improvement of a pulmonary function), amelioration of a medical condition associated with bronchiolitis (e.g., reduction of a microbial infection associated with bronchiolitis, reduction of the load of a pathogenic microorganism which is associated with bronchiolitis, reduction of inflammation), and reduction in the length of hospitalization of a patient.

In terms of following the efficacy of the treatment of bronchiolitis in an infant, it is generally accepted that pulmonary function is one of the most simple and direct marker for alleviating the symptoms of bronchiolitis, and hence that improvement of a pulmonary function in an infant represents a beneficial treatment of an infant suffering from bronchiolitis.

Without being bound by any particular theory, it is assumed that nitric oxide, delivered in an exogenous gaseous form, easily enters the pulmonary system and acts by pulmonary vasodilatation, reducing pathogenic microbial load, reducing inflammation, and alleviating other clinical symptoms.

In some embodiments, the method as described herein, in any one of the embodiments thereof, and in any combination thereof, is effected by improving one or more physiological parameters in an infant suffering from bronchiolitis which worsen by a medical condition associated with bronchiolitis.

An improvement of any of these parameters is indicative of the beneficial effect of the treatment by intermittent inhalation of nitric oxide, according to any one of the embodiments described herein.

According to some embodiments of the present invention, the method is effected by improving at least one pulmonary function (spirometric parameter), such as, but not limited to, Forced Expiratory Volume in 1 second ($FEV_1$), Forced Vital Capacity (FVC), $FEV_1$/FVC ratio or $FEV_1$% and Forced Expiratory Flow (FEF).

The spirometric parameter Forced Vital Capacity (FVC) is the volume of air measured in liters, which can forcibly be blown out after full inspiration, and constitutes the most basic maneuver in spirometry tests.

The spirometric parameter Forced Expiratory Volume in the 1st second ($FEV_1$) is the volume of air that can forcibly be blown out in one second, after full inspiration. Average values for $FEV_1$ depend mainly on sex and age, whereas values falling between 80% and 120% of the average value are considered normal. Predicted normal values for $FEV_1$ can be calculated on-site and depend on age, sex, height, weight and ethnicity as well as the research study that they are based on.

The spirometric parameter $FEV_1$/FVC ratio ($FEV_1$%) is the ratio of $FEV_1$ to FVC, which should be approximately 75-80%. The predicted $FEV_1$% is defined as $FEV_1$% of the patient divided by the average $FEV_1$% in the population appropriate for that patient.

The spirometric parameter Forced Expiratory Flow (FEF) is the flow (or speed) of air coming out of the lung during the middle portion of a forced expiration. It can be given at discrete times, generally defined by what fraction remains of the forced vital capacity (FVC), namely 25% of FVC ($FEF_{25}$), 50% of FVC ($FEF_{50}$) or 75% of FVC ($FEF_{75}$). It can also be given as a mean of the flow during an interval, also generally delimited by when specific fractions remain of FVC, usually 25-75% ($FEF_{25-75}$). Measured values ranging from 50-60% up to 130% of the average are considered normal, while predicted normal values for FEF can be calculated on-site and depend on age, sex, height, weight and ethnicity as well as the research study that they are based on. Recent research suggests that $FEF_{25-75}$% or $FEF_{25-50}$% may be a more sensitive parameter than $FEV_1$ in the detection of obstructive small airway disease. However, in the absence of concomitant changes in the standard markers, discrepancies in mid-range expiratory flow may not be specific enough to be useful, and current practice guidelines recommend continuing to use $FEV_1$, VC, and $FEV_1$/VC as indicators of obstructive disease.

It is noted that in some embodiments, other spirometric parameters, as these are defined and described herein below, may be used to follow the progression and efficacy of bronchiolitis treatment by intermittent inhalation of 160 ppm nitric oxide, and/or to follow safety parameters of the treatment.

According to some embodiments, $FEV_1$ is monitored as an on-site parameter, as defined hereinafter, which is indicative of the beneficial effect of the intermittent inhalation of nitric oxide, as provided herewith. In general, an increase in the $FEV_1$ level is regarded as a desired effect in infants suffering from bronchiolitis, wherein an increase of at least 3 percent in the $FEV_1$ baseline level of the patient (before commencing the treatment) is regarded as a notable improvement. In some embodiments, the method is effected such that $FEV_1$ level is increased by at least 3, 5, 10, 15 or 20 percent during and/or after the intermittent inhalation (e.g., during and/or after the entire time period intermittent inhalation of nitric oxide is effected) of nitric oxide, as described herein.

According to embodiments of the present invention, the method is effected so as to reduce the load of the pathogenic microorganism in the infant by at least one log unit during the intermittent inhalation treatment.

The term "log unit" as used herein to describe a change in the load of a pathogenic microorganism, also known as "log reduction" or "log increase", is a mathematical term used to show the relative number of live microbes eliminated from a system by carrying out the method of intermittent inhalation of nitric oxide, as presented herein. For example, a 5 log units reduction means lowering the number of microorganisms by 100,000-fold, that is, if a sample has 100,000 pathogenic microbes on it, a 5-log reduction would reduce the number of microorganisms to one. Hence, a 1 log unit reduction means the number of pathogenic microbes is 10 times smaller, a 2 log reduction means the number of pathogens is 100 times smaller, a 3 log reduction means the number of pathogens is 1000 times smaller, a 4 log reduction means the number of pathogens is 10,000 times smaller and so forth.

Bronchiolitisis is typically associated with a state of inflammation in at least one bodily site, e.g. the lungs, or an acute, chronic, local or systemic inflammation, cause by one or more medical conditions, including but not limited to pathogenic infections. Inflammation in an infant suffering from bronchiolitis can also be regarded as a secondary condition to bronchiolitis (a medical condition associated with bronchiolitis). According to some embodiments of the present invention, the method is effected by reducing the level of inflammation associated with bronchiolitis.

Reduction in inflammation associated with bronchiolitis is typically regarded as a beneficial effect of the treatment of bronchiolitis. Similarly, a reduction of a level of an inflammatory biomarker associated with bronchiolitis can be regarded as an indication of efficacy of the method of treating an infant suffering from bronchiolitis as presented herein.

In the context of some embodiments of the present invention, inflammatory or inflammation biomarkers associated with bronchiolitis include, without limitation, serum/blood levels of C-reactive protein (CRP), cytokines such as interleukins IL-6 and IL-1β, alpha-1-antitrypsin (AAT), haptoglobin, transferrin, various immunoglobulins, granzyme B (GzmB), chemokine C—C motif ligand 18 (CCL18/PARC), surfactant protein D (SP-D), lipopolysaccharide (LPS)-binding protein, and soluble cluster of differentiation 14 (sCD14).

The term "cytokine", as used in the context of embodiments of the present invention, include chemokines, interferons, interleukins, lymphokines and tumor necrosis factor.

Following is a brief description of four non-limiting exemplary inflammatory biomarkers associated with bronchiolitis.

Tumor Necrosis Factor alpha (TNFa) signals to the body to bring the neutrophil white blood cells to the site of infection or injury. TNFα is known as a cytokine, or a cell-signaling protein. TNFα acts like a "first responder" at an accident by signaling to the body where the most damage is so that the immune system can respond effectively, which is to send neutrophils.

Nuclear Factor kappa B (NFkB) is a transcription factor protein complex that acts as a switch for certain genes. When NFkB is allowed to enter the nucleus, which it does through the aid of TNFα, it turns on the genes which allow cells to proliferate, mature, and avoid destruction through apoptosis (programmed cell death). This allows white blood cells to replicate and effect their activity in cleaning up the infected or injured area. NFkB is similar to the priority setting on a communications line by opening all channels available for the quickest response.

Interleukin-6 (IL-6) is a cytokine that dictates the neutrophils to destroy themselves and draws monocytes, another type of white blood cell, to the infected or injured area instead. The monocytes create macrophages which clean up the debris and pathogens through phagocytosis, the process by which macrophages degrade dead cells and other particles whole.

C-Reactive Protein (CRP) is a "pattern recognition receptor" protein, which means it marks recognized debris for removal, that is produced by the liver in response to IL-6 levels and binds to the surface of dead and dying cells, and also to certain forms of bacteria. CRP acts as a form of signal for the macrophages to ingest something through phagocytosis, and thus helps in the ultimate clearing of debris during inflammation.

According to some embodiments, monitoring the level of an inflammatory biomarker associated with bronchiolitis is useful in determining the course and effect of the treatment of inflammation associated with bronchiolitis. In some embodiments, the level of a biomarker associated with bronchiolitis in the serum extracted from the infant, based on a baseline of the serum level in the infant before commencement of the treatment, is reduced by at least 3, 5, 10, 15, 20, 30, 35, 40, 50 or at least 60 percent during the treatment.

In some embodiment, the biomarker associated with bronchiolitis is CRP, and the serum level of CRP is reduced during the intermittent inhalation treatment by at least 3, 5, 10, 15, 20, 30, 35, 40, 50 or at least 60 percent, compared to the baseline level in the infant before commencement of the treatment.

In some embodiment, the biomarker associated with bronchiolitis is a cytokine, such as, but not limited to, TNFα, IL-1β, IL-6, IL-8, IL-10 and/or IL-12p70, and the serum level of the cytokine(s) is reduced by at least 3, 5, 10, 15, 20, 30, 35, 40, 50 or at least 60 percent, compared to the baseline level in the infant before commencement of the treatment. In some embodiments, the cytokines used as inflammatory biomarkers in the method presented herein are IL-6 and IL-β.

According to some embodiments of the present invention, there is provided a method of reducing a load of a pathogenic microorganism in an infant by subjecting the infant to intermittent inhalation of a gas mixture comprising nitric oxide at a concentration of at least 160 ppm.

In some embodiments, the pathogenic microorganism causes a microbial infection associated with bronchiolitis, as described herein. According to some embodiments, the pathogenic microorganism is selected from the group consisting of *P. alcaligenes*, non-mucoid and mucoid *Pseudomonas aeruginosa*, *A. fumigates*, *Staphylococcus aureus*, *Haemophilus influenza*, *Burkholderia cepacia complex*, *Klebsiella pneumonia*, *Escherichia coli*, methicillin-resistant *Staphylococcus aureus* (MRSA), methicillin-sensitive *Staphylococcus aureus* (MSSA), *Stenotrophomonas maltophilia*, *Achromobacter* spp., *Achromobacter xylosoxidans* and non-tuberculous mycobacteria (NTM) species.

According to some embodiments, the pathogenic microorganism is selected from the group consisting of *P. alcaligenes*, methicillin-sensitive *Staphylococcus aureus* (MSSA), *Achromobacter* spp., *A. fumigates*, non-mucoid *P. aeruginosa* and mucoid *P. aeruginosa*.

As discussed hereinabove, in some embodiments, the load of the pathogenic microorganism is reduced by the presently claimed method by at least 1 log units during the intermittent inhalation.

According to some embodiments of the present invention, there is provided a method of reducing a level of an inflammatory biomarker associated with bronchiolitis in an infant by subjecting the infant to a treatment by intermittent inhalation of a gas mixture comprising nitric oxide at a concentration of at least 160 ppm.

According to some embodiments, the inflammatory biomarker associated with bronchiolitis, and/or a change in its normal physiological level, is associated with cystic fibrosis and/or with complications and other medical conditions associated with bronchiolitis. Reducing a level of an inflammatory biomarker associated with bronchiolitis in an infant suffering from bronchiolitis is indicative of treating inflammation (as a secondary medical condition).

According to some embodiments, the inflammatory biomarker associated with bronchiolitis, which is targeted for reduction by the presently claimed method is selected from the group consisting of C-reactive protein (CRP), a cytokine, alpha-1-antitrypsin (AAT), haptoglobin, transferrin, an immunoglobulin, granzyme B (GzmB), chemokine C—C motif ligand 18 (CCL18/PARC), surfactant protein D (SP-D), lipopolysaccharide (LPS)-binding protein and soluble cluster of differentiation 14 (sCD14).

In some embodiments of this aspect of the present invention, the inflammatory biomarker associated with bronchiolitis is C-reactive protein (CRP). A rate of reduction as a result of the intermittent inhalation is at least 3, 5, 10, 15, 20, 30, 35, 40, 50 or at least 60 percent, compared to a baseline level of the biomarker in the patient.

In some embodiments of this aspect of the present invention, the inflammatory biomarker associated with bronchiolitis is a cytokine is selected from the group consisting of TNFα, IL-1β, IL-6, IL-8, IL-10 and IL-12p70. In some embodiments, the inflammatory biomarkers are IL-6 and IL-1β. A rate of reduction in the level of a cytokine as a result of the treatment is at least 3, 5, 10, 15, 20, 30, 35, 40, 50 or at least 60 percent, compared to a baseline level of the biomarker in the patient.

Intermittent Inhalation:

As presented hereinabove, any of the methods provided herewith comprise subjecting the infant to intermittent inhalation of a gas mixture comprising nitric oxide at a concentration of at least 160 ppm.

The term "intermittent" is used herein and in the art as an antonym of "continuous", and means starting and ceasing an action and/or performing an action in intervals.

By "intermittent inhalation" it is meant that an infant breathes a mixture of gases that contains an indicated concentration of nitric oxide intermittently; hence while the volume of the inhaled mixture of gases may not change significantly during the intermittent inhalation, the chemical composition of the mixture changes according to a predetermined regimen, as described herein below. The infant therefore inhales a gas mixture comprising nitric oxide at a concentration of at least 160 ppm for predetermined periods of time, and between these periods of time the infant inhales a gaseous mixture that is essentially devoid of nitric oxide (e.g., ambient air or another nitric oxide-free mixture).

Herein and throughout, "a nitric oxide-containing gaseous mixture" or "a gas mixture comprising nitric oxide" is used to describe a gaseous mixture that contains at least 160 ppm nitric oxide. The nitric oxide-containing mixture can comprise 160 ppm, 170 ppm, 180 ppm, 190 ppm, 200 ppm and even higher concentrations of nitric oxide. Other gaseous mixtures mentioned herein include less than 160 ppm nitric oxide or are being essentially devoid of nitric oxide, as defined herein.

By "essentially devoid of nitric oxide" it is meant no more than 50 ppm, no more than 40 ppm, no more than 30 ppm, no more than 20 ppm, no more than 10 ppm, no more than 5 ppm, no more than 1 ppm and no more than ppb, including absolutely no nitric oxide.

According to some embodiments of the present invention, the intermittent inhalation includes one or more cycles, each cycle comprising continuous inhalation of a gaseous mixture containing nitric oxide at the specified high concentration (e.g., at least 160 ppm) for a first time period, followed by inhalation of a gaseous mixture essentially devoid of nitric oxide for a second time period. According to some embodiments of the present invention, during the second period of time the infant may inhale ambient air or a controlled mixture of gases, which is essentially devoid of nitric oxide, as defined herein.

In some embodiments, the first time period spans from 10 minutes to 45 minutes, or from 20 to 45 minutes, or from 20 to 40 minutes, and according to some embodiments, spans about 30 minutes.

According to some embodiments of the present invention, the second time period ranges from 3 hours to 5 hours, or from 3 to 4 hours, and according to some embodiments the second time period spans about 3.5 hours.

According to some embodiments of the present invention, this inhalation regimen is repeated 1-6 times over 24 hours, depending on the duration of the first and second time periods.

In some embodiments, a cycle of intermittent delivery of nitric oxide, e.g., 160 ppm for 30 minutes followed by 3.5 hours of breathing no nitric oxide, is repeated from 1 to 6 times a day. According to some embodiments, the cycles are repeated 5 times a day. Alternatively the cycles are repeated 3 times a day.

According to some embodiments of the present invention, the regimen of 1-5 cycles per day is carried out for 1 to 21 days, or from 2 to 14 days, or from 3 to 10 days. According to some embodiments of the present invention, the intermittent inhalation is effected during a time period of 2 weeks. However, longer time periods of intermittent nitric oxide administration as described herein, are also contemplated.

Safety:

As discussed hereinabove, intermittent inhalation of 160 ppm of nitric oxide has been shown to be safe in human subjects of all ages. Safety has been demonstrated by monitoring one or more physiological parameters in the infant and while minding that no substantial adverse change is effected in the monitored parameters, as a safety measure of the method presented herein. According to any one of the embodiments of the present invention, the intermittent inhalation is effected while monitoring one or more physiological parameters in the infant.

In some embodiments, the methods disclosed herein are effected while monitoring various parameters relevant for maintaining the desired dosage and regimen, relevant to the safety of the procedure and relevant for efficacy of the treatment.

According to any one of the embodiments of the present invention, the method is effected while monitoring one or more physiological parameters in the infant and while minding that no substantial adverse change is effected in the monitored safety parameters, as a safety measure of the method presented herein.

In some embodiments, the method is carried out while maintaining safety measured which include non-invasive monitoring of bodily fluid chemistry, such as perfusion index (PI), respiration rate (RRa), oxyhemoglobin saturation ($SpO_2$/$SaO_2$/DO), total hemoglobin (SpHb), carboxyhemoglobin (SpCO), methemoglobin (SpMet), oxygen content (SpOC), and pleth variability index (PVI), as these physiological parameters are known in the art. Typically, these on-site physiological parameters are monitored by pulse oximetry.

Other parameters, also monitored as a safety measure on the presently disclosed method, according to some embodiments thereof, are off-site physiological parameters which are typically determined by collecting bodily samples using non-invasive (e.g., urine, feces or sputum samples) and invasive (e.g., blood or biopsy) method.

For example, off-site physiological parameters which are typically measured by invasive methods may include serum nitrite/nitrate ($NO_2^-$/$NO_3^-$), blood methemoglobin, a complete blood cells count (CBC), blood chemistry/biochemistry (electrolytes, renal and liver function tests etc.) and coagulation tests.

Off-site physiological parameters which are typically measured by non-invasive methods may include urine nitrite/nitrate ($NO_2^-$/$NO_3^-$), pregnancy tests in urine, and bacterial and fungal load in sputum, urine or feces.

In some embodiments, the method is carried out while maintaining safety measures which include controlling the mixture of inhaled gases and monitoring the exhaled gases, which is effected by standard means for monitoring and controlling, on-site, the contents and/or flow of the mixture to which the infant is subjected to, or that which is delivered through a delivery interface, and/or while monitoring on-site exhaled gases and controlling the intake by feedback in real-time. In some embodiments, the method is effected while monitoring the concentration of nitric oxide, $O_2$, $CO_2$ and $NO_2$ in the gaseous mixture to which the infant is exposed to, or exhales.

In some embodiments, the concentration of nitric oxide in the nitric oxide-containing gaseous mixture is controlled so as not to deviate from a predetermined concentration by more than 10%. For example, the method is carried out while the concentration of nitric oxide, set to 160 ppm, does not exceed substantially the margins of 144 ppm to 176 ppm.

Similarly, the $NO_2$ content in a nitric oxide-containing gaseous mixture is controlled such that the concentration of $NO_2$ is maintained lower than 5 ppm.

Further, oxygen level in the nitric oxide-containing gaseous mixture is controlled such that the concentration of $O_2$ in the mixture ranges from about 20% to about 25%.

Alternatively or in addition, the oxygen level in the nitric oxide-containing gaseous mixture is controlled such that the fraction of inspired oxygen ($FiO_2$) ranges from about 20% to about 100%.

The phrase "fraction of inspired oxygen" or "$FiO_2$", as used herein, refers to the fraction or percentage of oxygen in a given gas sample. For example, ambient air at sea level includes 20.9% oxygen, which is equivalent to $FiO_2$ of 0.21. Oxygen-enriched air has a higher $FiO_2$ than 0.21, up to 1.00, which means 100% oxygen. In the context of embodiments of the present invention, $FiO_2$ is kept under 1 (less than 100% oxygen).

According to some embodiments, fraction of inspired oxygen ($FiO_2$) in the nitric oxide-containing gaseous mixture is 0.20. In an alternate embodiment, the $FiO_2$ in the nitric oxide-containing gaseous mixture is 0.25. In an alternate embodiment, the $FiO_2$ in the nitric oxide-containing gaseous mixture is 0.3. In an alternate embodiment, the $FiO_2$ in the nitric oxide-containing gaseous mixture is 0.35. In an alternate embodiment, the $FiO_2$ in the nitric oxide-containing gaseous mixture is 0.4. In an alternate embodiment, the $FiO_2$ in the nitric oxide-containing gaseous mixture is 0.45. In an alternate embodiment, the $FiO_2$ in the nitric oxide-containing gaseous mixture is 0.5. In an alternate embodiment, the $FiO_2$ in the nitric oxide-containing gaseous mixture is 0.55. In an alternate embodiment, the $FiO_2$ in the nitric oxide-containing gaseous mixture is 0.6. In an alternate embodiment, the $FiO_2$ in the nitric oxide-containing gaseous mixture is 0.65. In an alternate embodiment, the $FiO_2$ in the nitric oxide-containing gaseous mixture is 0.7. In an alternate embodiment, the $FiO_2$ in the nitric oxide-containing gaseous mixture is 0.75. In an alternate embodiment, the $FiO_2$ in the nitric oxide-containing gaseous mixture is 0.8. In an alternate embodiment, the $FiO_2$ in the nitric oxide-containing gaseous mixture is 0.85. In an alternate embodiment, the $FiO_2$ in the nitric oxide-containing gaseous mixture is 0.9. In an alternate embodiment, the $FiO_2$ in the nitric oxide-containing gaseous mixture is 0.95.

In some embodiments, the nitric oxide-containing gaseous mixture is formed by combining a stock supply of nitric oxide with air, which dilutes the stock supply of nitric oxide to the desired concentration. In some embodiments, the stock supply of nitric oxide is combined with air and oxygen to keep the $FiO_2$ above 0.20. The ratio of nitric oxide, air and/or oxygen can be varied to achieve the desired nitric oxide concentration and $FiO_2$.

The phrase "end tidal $CO_2$" or "$ETCO_2$", as used herein, refers to the partial pressure or maximal concentration of carbon dioxide ($CO_2$) at the end of an exhaled breath, which is expressed as a percentage of $CO_2$ or the pressure unit mmHg. Normal values for humans range from 5% to 6% $CO_2$, which is equivalent to 35-45 mmHg. Since $CO_2$ diffuses out of the lungs into the exhaled air, $ETCO_2$ values reflect cardiac output (CO) and pulmonary blood flow as the gas is transported by the venous system to the right side of the heart and then pumped to the lungs by the right ventricles. A device called capnometer measures the partial pressure or maximal concentration of $CO_2$ at the end of exhalation. In the context of embodiments of the present invention, a capnometer is used and $ETCO_2$ levels are monitored so as to afford a warning feedback when $ETCO_2$ is more than 60 mmHg.

Levels of respiratory NO, $NO_2$ and $O_2$ concentration levels (both inhaled and exhaled; inspiratory and expiratory gases) are typically monitored continuously by sampling from a mouthpiece sample port located in an inhalation mask NO, $NO_2$ and $O_2$ equipped with an electrochemical analyzer. In the context of embodiments of the present invention, safety considerations requires the absolute minimization of the number of occasions in which $NO_2$ levels exceed 5 ppm, nitric oxide concentration variations exceeding 10%, and $FiO_2/O_2$ levels drop below 20% during nitric oxide administration.

It is noted that a sharp elevation of inflammatory biomarkers may be associated with a phenomenon called "cytokine storm", which has been observed in infants undergoing nitric oxide inhalation treatment. Hence, monitoring inflammatory biomarkers while performing the method as described herein has an additional role in safety considerations pertaining to the method, according to embodiments of the present invention, wherein no significant increase in inflammatory markers is an indication of safety.

In some embodiments, monitoring the one or more physiological parameters is effected by noninvasive measures and/or mild invasive measures.

In some embodiments, monitoring the physiological parameter(s) in the infant is effected by on-site measurement and analysis techniques based on samples collected sporadically, continuously or periodically from the infant on-site in real-time at the infant's bed-side, and/or off-site measurement and analysis techniques based on samples collected sporadically or periodically from the infant which are sent for processing in a off-site which provides the results and analysis at a later point in time.

In the context of some embodiments of the present invention, the phrase "on-site measurement and analysis techniques" or "on-site techniques", refers to monitoring techniques that inform the practitioner of a given physiological parameter of the infant in real-time, without the need to send the sample or raw data to an off-site facility for analysis. On-site techniques are often noninvasive, however, some rely on sampling from an invasive medical device such as a respiratory tubus, a drainer tube, an intravenous catheter or a subcutaneous port or any other implantable probe. Thus, the phrase "on-site parameters", as used herein, refers to physiological parameters which are obtainable by online techniques.

Other than the trivial advantage of real-time on-site determination of physiological parameters, expressed mostly in the ability of a practitioner to respond immediately and manually to any critical change thereof, the data resulting from real-time online determination of physiological parameters can be fed into the machinery and be used for real-time feedback controlling of the machinery. In the context of embodiments of the present invention, the term "real-time" also relates to systems that update information and respond thereto substantially at the same rate they receive the information. Such real-time feedback can be used to adhere to the treatment regimen and/or act immediately and automatically in response to any critical deviations from acceptable parameters as a safety measure.

Hence, according to embodiments of the present invention, the term "on-site parameter" refers to physiological and/or mechanical and/or chemical datum which is obtainable and can be put to use or consideration at or near the infant's site (e.g., bed-side) in a relatively short period of time, namely that the time period spanning the steps of sampling, testing, processing and displaying/using the datum is relatively short. An "on-site parameter" can be obtainable, for example, in less than 30 minutes, less than 10 minutes, less than 5 minutes, less than 1 minute, less than 0.5 minutes, less than 20 seconds, less than 10 seconds, less than 5 seconds, or less than 1 second from sampling to use. For example, the time period required to obtain on-site parameters by a technique known as pulse oximetry is almost instantaneous; once the device is in place and set up, data concerning, e.g., oxygen saturation in the periphery of an infant, are available in less than 1 second from sampling to use.

In the context of some embodiments of the present invention, the phrase "off-site measurement and analysis techniques" or "off-site techniques", refers to techniques that provide information regarding a given physiological parameter of the infant after sending a sample or raw data to an offline, and typically off-site facility, and receiving the analysis offline, sometimes hours or days after the sample had been obtained. Off-site techniques are oftentimes based on samples collected by mild invasive techniques, such as blood extraction for monitoring inflammatory cytokine plasma level, and invasive techniques, such as biopsy, catheters or drainer tubus, however, some off-site techniques rely on noninvasive sampling such as urine and stool chemistry offline and off-site analyses. The phrase "off-site parameters", as used herein, refers to physiological parameters which are obtainable by off-site laboratory techniques.

Hence, according to embodiments of the present invention, the term "off-site parameter" refers to physiological and/or mechanical and/or chemical datum which is obtain and can be put to use or consideration in a relatively long period of time, namely that the time period spanning the steps of sampling, testing, processing and displaying/using the datum is long compared to on-site parameters. Thus, an "off-site parameter" is obtainable in more than 1 day, more than 12 hours, more than 1 hour, more than 30 minutes, more than 10 minutes, or more than 5 minutes from sampling to use.

An "off-site parameter" is typically obtainable upon subjecting a sample to chemical, biological, mechanical or other procedures, which are typically performed in a laboratory and hence are not performed "on-site", namely by or near the infant's site.

Noninvasive measures for monitoring various physiological parameters include, without limitation, sputum, urine and feces sampling, pulse oximetry, nonintubated respiratory analysis and/or capnometry. Invasive measures for monitoring various physiological parameters include, without limitation, blood extraction, continuous blood gas and metabolite analysis, and in some embodiments intubated respiratory analysis and transcutaneous monitoring measures. Intense invasive measures include biopsy and other surgical procedures.

The term "pulse oximetry" refers to a noninvasive and on-site technology that measures respiration-related physiological parameters by following light absorption characteristics of hemoglobin through the skin (finger, ear lobe etc.), and on the spectroscopic differences observed in oxygenated and deoxygenated species of hemoglobin, as well as hemoglobin species bound to other molecules, such as carbon monoxide (CO), and methemoglobin wherein the iron in the heme group is in the $Fe^{3+}$ (ferric) state. Physiological parameters that can be determined by pulse oximetry include, for example, $SpO_2$, SpMet and SpCO.

The phrase "nonintubated respiratory analysis", as used herein, refers to a group of noninvasive and on-site technologies, such as spirometry and capnography, which provide measurements of the physiological pulmonary mechanics and respiratory gaseous chemistry by sampling the inhaled/exhaled airflow or by directing infant's breath to a detector, all without entering the infant's respiratory tract or other orifices nor penetrating the skin at any stage.

The term "spirometry" as used herein, refers to the battery of measurements of respiration-related parameters and pulmonary functions by means of a noninvasive and on-site spirometer. Following are exemplary spirometry parameters which may be used in the context of some embodiments of the present invention:

The spirometric parameter Tidal volume (TV) is the amount of air inhaled and exhaled normally at rest, wherein normal values are based on person's ideal body weight.

The spirometric parameter Total Lung Capacity (TLC) is the maximum volume of air present in the lungs.

The spirometric parameter Vital Capacity (VC) is the maximum amount of air that can expel from the lungs after maximal inhalation, and is equal to the sum of inspiratory reserve volume, tidal volume, and expiratory reserve volume.

The spirometric parameter Slow Vital Capacity (SVC) is the amount of air that is inhaled as deeply as possible and then exhaled completely, which measures how deeply an infant can breathe.

The spirometric parameter Forced Vital Capacity (FVC) is the volume of air measured in liters, which can forcibly be blown out after full inspiration, and constitutes the most basic maneuver in spirometry tests.

The spirometric parameter Forced Expiratory Volume in the 1st second ($FEV_1$) is the volume of air that can forcibly be blown out in one second, after full inspiration. Average values for $FEV_1$ depend mainly on sex and age, whereas values falling between 80% and 120% of the average value are considered normal. Predicted normal values for $FEV_1$ can be calculated on-site and depend on age, sex, height, weight and ethnicity as well as the research study that they are based on.

The spirometric parameter $FEV_1$/FVC ratio ($FEV_1$%) is the ratio of $FEV_1$ to FVC, which in adults should be approximately 75-80%. The predicted FEV1% is defined as $FEV_1$% of the patient divided by the average $FEV_1$% in the appropriate population for that person.

The spirometric parameter Forced Expiratory Flow (FEF) is the flow (or speed) of air coming out of the lung during the middle portion of a forced expiration. It can be given at discrete times, generally defined by what fraction remains of the forced vital capacity (FVC), namely 25% of FVC ($FEF_{25}$), 50% of FVC ($FEF_{50}$) or 75% of FVC ($FEF_{75}$). It can also be given as a mean of the flow during an interval, also generally delimited by when specific fractions remain of FVC, usually 25-75% ($FEF_{25-75}$%). Measured values ranging from 50-60% up to 130% of the average are considered normal, while predicted normal values for FEF can be calculated on-site and depend on age, sex, height, weight and ethnicity as well as the research study that they are based on. Recent research suggests that $FEF_{25-75}$% or $FEF_{25-50}$% may be a more sensitive parameter than $FEV_1$ in the detection of obstructive small airway disease. However, in the absence of concomitant changes in the standard markers, discrepancies in mid-range expiratory flow may not be specific enough to be useful, and current practice guidelines recommend continuing to use $FEV_1$, VC, and $FEV_1$/VC as indicators of obstructive disease.

The spirometric parameter Negative Inspiratory Force (NIF) is the greatest force that the chest muscles can exert to take in a breath, wherein values indicate the state of the breathing muscles.

The spirometric parameter MMEF or MEF refers to maximal (mid-)expiratory flow and is the peak of expiratory flow as taken from the flow-volume curve and measured in liters per second. MMEF is related to peak expiratory flow (PEF), which is generally measured by a peak flow meter and given in liters per minute.

The spirometric parameter Peak Expiratory Flow (PEF) refers to the maximal flow (or speed) achieved during the maximally forced expiration initiated at full inspiration, measured in liters per minute.

The spirometric parameter diffusing capacity of carbon monoxide ($D_LCO$) refers to the carbon monoxide uptake from a single inspiration in a standard time (usually 10 sec). On-site calculators are available to correct $D_LCO$ for hemoglobin levels, anemia, pulmonary hemorrhage and altitude and/or atmospheric pressure where the measurement was taken.

The spirometric parameter Maximum Voluntary Ventilation (MVV) is a measure of the maximum amount of air that can be inhaled and exhaled within one minute. Typically this parameter is determined over a 15 second time period before being extrapolated to a value for one minute expressed as liters/minute. Average values for males and females are 140-180 and 80-120 liters per minute respectively.

The spirometric parameter static lung compliance (Cst) refers to the change in lung volume for any given applied pressure. Static lung compliance is perhaps the most sensitive parameter for the detection of abnormal pulmonary mechanics. Cst is considered normal if it is 60% to 140% of the average value of a commensurable population.

The spirometric parameter Forced Expiratory Time (FET) measures the length of the expiration in seconds.

The spirometric parameter Slow Vital Capacity (SVC) is the maximum volume of air that can be exhaled slowly after slow maximum inhalation.

Static intrinsic positive end-expiratory pressure (static PEEPi) is measured as a plateau airway opening pressure during airway occlusion.

The spirometric parameter Maximum Inspiratory Pressure (MIP) is the value representing the highest level of negative pressure a person can generate on their own during an inhalation, which is expresented by centimeters of water pressure ($cmH_2O$) and measured with a manometer and serves as n indicator of diaphragm strength and an independent diagnostic parameter.

The term "capnography" refers to a technology for monitoring the concentration or partial pressure of carbon dioxide ($CO_2$) in the respiratory gases. End-tidal $CO_2$, or $ETCO_2$, is the parameter that can be determined by capnography.

Gas detection technology is integrated into many medical and other industrial devices and allows the quantitative determination of the chemical composition of a gaseous sample which flows or otherwise captured therein. In the context of embodiments of the present invention, such chemical determination of gases is part of the on-site, noninvasive battery of tests, controlled and monitored activity of the methods presented herein. Gas detectors, as well as gas mixers and regulators, are used to determine and control parameters such as fraction of inspired oxygen level ($FiO_2$) and the concentration of nitric oxide in the inhaled gas mixture.

According to some embodiments of the present invention, the measurement of vital signs, such as heart rate, blood pressure, respiratory rate and a body temperature, is regarded as part of a battery of on-site and noninvasive measurements.

The phrase "integrated pulmonary index", or IPI, refers to a patient's pulmonary index which uses information on inhaled/exhaled gases from capnography and on gases dissolved in the blood from pulse oximetry to provide a single value that describes the patient's respiratory status. IPI, which is obtained by on-site and noninvasive techniques, integrates four major physiological parameters provided by a patient monitor (end-tidal $CO_2$ and respiratory rate as measured by capnography, and pulse rate and blood oxygenation $SpO_2$ as measured by pulse oximetry), using this information along with an algorithm to produce the IPI score. IPI provides a simple indication in real time (on-site) of the patient's overall ventilatory status as an integer (score) ranging from 1 to 10. IPI score does not replace current patient respiratory parameters, but used to assess the patient's respiratory status quickly so as to determine the need for additional clinical assessment or intervention.

According to some of the embodiments described herein, the monitored physiological or chemical parameters include one or more of the following parameters:
  Perfusion Index (PI);
  Respiration Rate (RRa);
  Oxyhemoglobin Saturation ($SpO_2$);
  Total Hemoglobin (SpHb);
  Carboxyhemoglobin (SpCO);
  Methemoglobin (SpMet);
  Oxygen Content (SpOC); and
  Pleth Variability Index (PVI),
    and/or at least one off-site parameter selected from the group consisting of: serum nitrite/nitrate ($NO_2^-/NO_3^-$);
    serum or urine nitrite/nitrate ($NO_2^-/NO_3^-$) and blood methemoglobin.

According to some of the embodiments described herein, the monitored physiological or chemical parameters include one or more of the following parameters:
  Perfusion Index (PI);
  Respiration Rate (RRa);
  Oxyhemoglobin Saturation ($SpO_2$);
  Total Hemoglobin (SpHb);
  Carboxyhemoglobin (SpCO);
  Methemoglobin (SpMet);
  Oxygen Content (SpOC); and
  Pleth Variability Index (PVI),
    and/or at least one off-site parameter selected from the group consisting of: serum nitrite/nitrate ($NO_2^-/NO_3^-$); and
  skin salinity.

According to some of the embodiments described herein, the method is conducted while monitoring at least one of the following on-site parameters in the gas mixture inhaled by the infant:
  End Tidal $CO_2$ ($ETCO_2$);
  Nitrogen dioxide ($NO_2$),
  Nitric oxide (NO); and
  Fraction of inspired oxygen ($FiO_2$).

According to some of the embodiments described herein, the monitored physiological or chemical parameters further include one or more of the following parameters:
  a urine level of nitrogen dioxide (urine nitrite level) (an off-line parameter);
  a vital sign selected from the group consisting of a heart rate, a blood pressure, a respiratory rate and a body temperature (an on-line parameter);
  a hematological marker (an off-line parameter), such as, but not limited to, a hemoglobin level, a hematocrit ratio, a red blood cell count, a white blood cell count, a white blood cell differential and a platelet count;
  a coagulation parameter (an off-line parameter) such as, but not limited to, a prothrombin time (PT), a prothrombin ratio (PR) and an international normalized ratio (INR);
  a serum creatinine level (an off-line parameter);
  a liver function marker (an off-line parameter) selected from the group consisting of a aspartate aminotransferase (AST) level, a serum glutamic oxaloacetic transaminase (SGOT) level, an alkaline phosphatase level, and a gamma-glutamyl transferase (GGT) level;
  a vascular endothelial activation factor (an off-line parameter) selected from the group consisting of Ang-1, Ang-2 and Ang-2/Ang-1 ratio.

It is noted that a sharp elevation of inflammatory biomarkers may be associated with a phenomenon called "cytokine storm", which has been observed in infants undergoing nitric oxide inhalation treatment. Hence, monitoring inflammatory biomarkers while performing the method as described herein has an additional role in safety considerations pertaining to the method, according to embodiments of the present invention, wherein no significant increase in inflammatory markers is an indication of safety.

According to some embodiments of the present invention, the method as disclosed herein is such that no substantial change is observed in at least one of the monitored physiological parameters or a level of biomarkers pertaining to the safety and efficacy of the treatment presented hereinabove.

In the context of the present embodiments, a change in a parameter or a level of a biomarker is considered substantial when a value of an observation (measurement, test result, reading, calculated result and the likes) or a group of observations falls notably away from a normal level, for example falls about twice the upper limit of a normal level.

A "normal" level of a parameter or a level of a biomarker is referred to herein as baseline values or simply "baseline". In the context of the present embodiments, the term "baseline" is defined as a range of values which have been determined statistically from a large number of observations and/or measurements which have been collected over years of medical practice with respect to the general human population, a specific sub-set thereof (cohort) or in some cases with respect to a specific person. A baseline is a parameter/biomarker-specific value which is generally and medically accepted in the art as normal for an infant under certain physical conditions. These baseline or "normal" values, and means of determining these normal values, are known in the art. Alternatively, a baseline value may be determined from or in a specific infant before effecting the method described herein using well known and accepted methods, procedures and technical means. A baseline is therefore associated with a range of tolerated values, or tolerance, which have been determined in conjunction with the measurement of a parameter/biomarker. In other words, a baseline is a range of acceptable values which limit the range of observations which are considered as "normal". The width of the baseline, or the difference between the upper and lower limits thereof are referred to as the "baseline range", the difference from the center of the range is referred to herein as the "acceptable deviation unit" or ADU. For example, a baseline of 4-to-8 has a baseline range of 4 and an acceptable deviation unit of 2.

In the context of the present embodiments, a significant change in an observation pertaining to a given parameter/biomarker is one that falls more than 2 acceptable deviation unit (2 ADU) from a predetermined acceptable baseline. For example, an observation of 10, pertaining to a baseline of 4-to-8 (characterized by a baseline range of 4, and an acceptable deviation unit of 2), falls one acceptable deviation unit, or 1 AUD from baseline. Alternatively, a change is regarded substantial when it is more than 1.5 ADU, more than 1 ADU or more than 0.5 ADU.

In the context of the present embodiments, a "statistically significant observation" or a "statistically significant deviation from a baseline" is such that it is unlikely to have occurred as a result of a random factor, error or chance.

It is noted that in some parameters/biomarkers or groups of parameters/biomarkers, the significance of a change thereof may be context-dependent, biological system-dependent, medical case-dependent, infant-dependent, and even measuring machinery-dependent, namely a particular parameter/biomarker may require or dictate stricter or looser criteria to determine if a reading thereof should be regarded as significant. It is noted herein that in specific cases some parameters/biomarkers may not be measurable due to patient condition, age or other reasons. In such cases the method is effected while monitoring the other parameters/biomarkers.

A deviation from a baseline is therefore defined as a statistically significant change in the value of the parameter/biomarker as measured during and/or following a full term or a part term of administration the regimen described herein, compared to the corresponding baseline of the parameter/biomarker. It is noted herein that observations of some parameters/biomarkers may fluctuate for several reasons, and a determination of a significant change therein should take such events into consideration and correct the appropriate baseline accordingly.

Monitoring methemoglobin and serum nitrite levels has been accepted in the art as a required for monitoring the safety of nitric oxide inhalation in an infant. Yet, to date, no clear indication that methemoglobin and serum nitrite levels remain substantially unchanged upon nitric oxide inhalation by an infant.

According to some embodiments of the present invention, the method comprises monitoring and/or improving at least one of the parameters/biomarkers described hereinabove.

According to some embodiments, the monitored parameter is methemoglobin level.

As methemoglobin levels can be measured using noninvasive measures, the parameter of percent saturation at the periphery of methemoglobin (SpMet) is used to monitor the stability, safety and effectiveness of the method presented herein. Hence, according to some embodiments of the present invention, the followed parameter is SpMet and during and following the administration, the SpMet level does not exceed 5%, and preferably does not exceed 1%. As demonstrated in the Examples section that follows, a SpMet level of infants undergoing the method described herein does not exceed 1%.

According to some embodiments, the monitored parameter is serum nitrate/nitrite level.

High nitrite and nitrate levels in a infant's serum are associated with nitric oxide toxicity and therefore serum nitrite/nitrate levels are used to detect adverse effects of the method presented herein. According to some embodiments of the present invention, the tested parameter is serum nitrite/nitrate, which is monitored during and following the treatment and the acceptable level of serum nitrite is less than 2.5 micromole/liter and serum nitrate is less than 25 micromole/liter.

According to some of the embodiments described herein, the method is effected while monitoring at least one, at least two, or all on-site parameters which include perfusion index (PI), respiration rate (RRa), oxyhemoglobin saturation ($SpO_2$/$SaO_2$/DO), total hemoglobin (SpHb), carboxyhemoglobin (SpCO), methemoglobin (SpMet), oxygen content (SpOC), and pleth variability index (PVI), and/or monitoring at least one or all off-site parameters which include serum nitrite/nitrate level.

According to some of the embodiments described herein, the method is effected while monitoring at least one, at least two, or all on-site parameters in the gas mixture inhaled by the infant, which include end tidal $CO_2$ ($ETCO_2$), nitrogen dioxide ($NO_2$), nitric oxide (NO) and fraction of inspired oxygen ($FiO_2$).

According to some of the embodiments described herein, the method is effected while monitoring at least one, at least two, or all on-site and/or off-site safety parameters pertaining to nitric oxide inhalation, e.g., methemoglobin formation, and while monitoring at least one, at least two, or all on-site and/or off-site efficacy parameters.

According to some of the embodiments described herein, the method is effected while monitoring at least one, at least two, or all on-site and/or off-site safety parameters pertaining to nitric oxide inhalation, e.g., methemoglobin formation, and while monitoring at least one, at least two, or all on-site and/or off-site efficacy parameters pertaining to CF symptoms, which include, pulmonary functions and/or inflammatory biomarkers.

According to some of the embodiments described herein, the method is effected while monitoring at least one, at least two, or all on-site and/or off-site safety parameters pertaining to nitric oxide inhalation, e.g., methemoglobin formation, and while monitoring at least one, at least two, or all on-site and/or off-site efficacy parameters pertaining to bronchiolitis symptoms, which include, pulmonary functions and/or inflammatory biomarkers.

According to some of the embodiments described herein, the method is effected while monitoring at least one, at least two, or all on-site pulmonary function parameters (spirometric parameters), such as forced expiratory volume ($FEV_1$), maximum mid-expiratory flow (MMEF), diffusing capacity of the lung for carbon monoxide ($D_LCO$), forced vital capacity (FVC), total lung capacity (TLC) and residual volume (RV).

For example, the method according to some embodiments is effected while monitoring SpMet as an on-site parameter. Alternatively, the method is effected while monitoring SpMet and $ETCO_2$ as on-site parameters. Alternatively, the method is effected while monitoring SpMet, $ETCO_2$ and $SpO_2$ as on-site parameters.

Alternatively, the method according to some embodiments is effected while monitoring SpMet as one on-site parameter, and one off-site parameter, such as plasma or urine levels of $NO_2^-/NO_3^-$. Alternatively, the method is effected while monitoring SpMet and $SpO_2$ as on-site parameters, and serum nitrite/nitrate level as one off-site parameter. Alternatively, the method is effected while monitoring SpMet as one on-site parameter, and inflammatory biomarkers in the plasma (for efficacy) and serum nitrite/nitrate level as off-site parameters. Alternatively, the method is effected while monitoring $SpO_2$ as one on-site parameter, and bacterial load and serum nitrite/nitrate level as off-site parameters. Alternatively, the method is effected while monitoring $SpO_2$ as one on-site parameter, and inflammatory biomarkers in the plasma and pulmonary function parameters such as $FEV_1$.

Further alternatively, the method is effected while monitoring SpMet, $FEV_1$ and $SpO_2$ as on-site parameters, and inflammatory biomarkers in the plasma and serum nitrite/nitrate level as off-site parameters.

According to some of the embodiments described herein, the method is effected while monitoring at least one, at least two, or all on-site parameters which include SpMet, $SpO_2$ and $FEV_1$, and/or monitoring at least one or all off-site parameters which include serum nitrite/nitrate level and inflammatory biomarkers in the plasma, and further monitoring one or more and in any combination of:
 a urine $NO_2$ level (an off-site parameter);
 a vital sign (an on-site parameter);
 a pulmonary function (an on-site parameter);
 a hematological marker (an off-site parameter);
 a coagulation parameter (an off-site parameter);
 a serum creatinine level (an off-site parameter);
 a renal function marker (an off-site parameter);
 a liver function marker (an off-site parameter);
 a vascular endothelial activation factor (an off-site parameter).

According to some of the embodiments described herein, the method is effected while monitoring at least one, at least two, or all on-site chemical parameters in the inhaled gas mixture, such as $FiO_2$ and $NO_2$.

It is noted herein that for any of the abovementioned embodiments, that the method is effected while no substantial change is observed in any one or more than one or all of the monitored parameters described herein.

According to some embodiments of the present invention, the method is effected while monitoring urine nitrite levels, such that the urine nitrite level is substantially unchanged during and subsequent to carrying out the method as presented herein. It is noted herein that urine nitrite levels may fluctuate for several known reasons, and a determination of a significant change therein should take such events into consideration and correct the appropriate baseline accordingly.

According to some embodiments of the present invention, hematological markers, such as the hemoglobin level, the hematocrit ratio, the red blood cell count, the white blood cell count, the white blood cell differential and the platelet count, are substantially unchanged during and subsequent to carrying out the method as presented herein.

According to some embodiments of the present invention, vascular endothelial activation factors, such as Ang-1, Ang-2 and Ang-2/Ang-1 ratio, as well as the serum creatinine level and various liver function markers, such as the aspartate aminotransferase (AST) level, the serum glutamic oxaloacetic transaminase (SGOT) level, the alkaline phosphatase level, and the gamma-glutamyl transferase (GGT) level, are substantially unchanged during and subsequent to carrying out the method as presented herein.

Oxygenation of the infant can be assessed by measuring the infant's saturation of peripheral oxygen ($SpO_2$). This parameter is an estimation of the oxygen saturation level, and it is typically measured using noninvasive measures, such as a pulse oximeter device. Hence, according to some embodiments of the present invention, the followed parameter during and following the administration is $SpO_2$, and the level of $SpO_2$ is higher than about 89%.

According to some embodiments of the present invention, various vital signs, such as the heart rate, the blood pressure, the respiratory rate and the body temperature; and various coagulation parameters, such as the prothrombin time (PT), the prothrombin ratio (PR) and the international normalized ratio (INR), are substantially unchanged during and subsequent to carrying out the method as presented herein. It is noted that these parameters are regarded as an indication that the general health of the infant is not deteriorating as a result of the medical condition and/or the treatment.

According to some embodiments, the aforementioned general health indicators show an improvement during and subsequent to carrying out the method as presented herein, indicating that the treatment is beneficial to the infant.

Thus, according to some embodiments of the present invention, the method as disclosed herein is effected such that general health indicators as described herein are at least remained unchanged or are improved.

Modes of Administration and Inhalation Devices:

The infant can be subjected to the inhalation by active or passive means.

By "active means" it is meant that the gaseous mixture is administered or delivered to the respiratory tract of the infant. This can effected, for example, by means of an inhalation device having a delivery interface adapted for human respiratory organs. For example, the delivery interface can be placed intermittently on the infant's respiratory organs, whereby when it is removed, the infant breaths ambient air or any other gaseous mixture that is devoid of nitric oxide, as defined herein.

By "passive means" it is meant that the infant inhales a gaseous mixture containing the indicated dose of nitric oxide without devices for delivering the gaseous mixture to the respiratory tract.

For example, the infant can be subjected to 160 ppm or more nitric oxide in an intermittent regimen by entering and exiting an atmospherically controlled enclosure filled with the nitric oxide-containing mixture of gases discussed herein, or by filling and evacuating an atmospherically controlled enclosure which is in contact with a infant's respiratory tract.

According to some embodiments of the present invention, in any of the methods of treatment presented herein, the nitric oxide administration can be effected by an inhalation device which includes, without limitation, a stationary inhalation device, a portable inhaler, a metered-dose inhaler and an intubated inhaler.

An inhaler, according to some embodiments of the present invention, can generate spirometry data and adjust the treatment accordingly over time as provided, for example, in U.S. Pat. No. 5,724,986 and WO 2005/046426. The inhaler can modulate the subject's inhalation waveform to target specific lung sites. According to some embodiments of the present invention, a portable inhaler can deliver both rescue and maintenance doses of nitric oxide at the infant's selection or automatically according to a specified regimen.

According to some embodiments of the present invention, an exemplary inhalation device may include a delivery interface adaptable for inhalation by a an infant.

According to some embodiments of the present invention, the delivery interface includes a mask or a mouthpiece for delivery of the mixture of gases containing nitric oxide to a respiratory organ of the infant.

According to some embodiments of the present invention, the inhalation device further includes a nitric oxide analyzer positioned in proximity to the delivery interface for measuring the concentration of nitric oxide, oxygen and nitrogen dioxide flowing to the delivery interface, wherein the analyzer is in communication with the controller.

According to some embodiments of the present invention, subjecting the infant to the method described herein is carried out by use of an inhalation device which can be any device which can deliver the mixture of gases containing nitric oxide to a respiratory organ of the infant. An inhalation device, according to some embodiments of the present invention, includes, without limitation, a stationary inhalation device comprising tanks, gauges, tubing, a mask, controllers, values and the likes; a portable inhaler (inclusive of the aforementioned components), a metered-dose inhaler, a an atmospherically controlled enclosure, a respiration machine/system and an intubated inhalation/respiration machine/system. An atmospherically controlled enclosure includes, without limitation, a head enclosure (bubble), a full body enclosure or a room, wherein the atmosphere filling the enclosure can be controlled by flow, by a continuous or intermittent content exchange or any other form of controlling the gaseous mixture content thereof.

According to some embodiments of the invention, the intermittent inhalation is effected by intermittently subjecting the infant to a gaseous mixture (the inhalant) by breathing cycle-coordinated pulse delivery, which contains nitric oxide at the indicated concentration (a nitric oxide-containing gaseous mixture). This mode of inhalation is referred to herein as intermittent breathing cycle-coordinated pulse delivery inhalation.

According to an alternative aspect of some embodiments of the present invention, there is provided a method of treating bronchiolitis in an infant which includes subjecting the infant to intermittent inhalation of an inhalant, whereas the intermittent inhalation includes at least one cycle of a breathing cycle-coordinated pulse delivery inhalation of the inhalant for a first time period, followed by inhalation of essentially no nitric oxide for a second time period, wherein the breathing cycle-coordinated pulse delivery inhalation is configured to deliver about 80 ppm-hour of nitric oxide during at least one cycle.

In the context of embodiments of the present invention, the term "nitric oxide-load" ("NO-load") refers to a certain cumulative amount of nitric oxide to which a subject, or a pathogen, is exposed to during inhalation treatment (e.g., the presently claimed treatment), which is estimated in terms of ppm-hour, namely the average concentration of nitric oxide in the inhalant multiplied by the overall time of exposure. The nitric oxide-load can be estimated per cycle of the treatment (NO-load per cycle), or per a time unit, such as a day (daily NO-load).

According to some embodiments of the present invention, the intermittent delivery of nitric oxide to the infant is conducted such that the subject inhales nitric oxide at an nitric oxide-load that ranges from 600 ppm-hour to 2000 ppm-hour daily, wherein the intermittent delivery is effected such that the daily nitric oxide-load is inhaled in more than one session of uninterrupted administration.

According to some embodiments of the present invention, the intermittent delivery is effected such that the daily nitric oxide-load is inhaled in one or more sessions of intermittent breathing cycle-coordinated pulse delivery inhalation, while the nitric oxide-load per cycle of each cycle is at least about 80 ppm-hour. Such nitric oxide-load per cycle can be obtained, for example, by configuring the pulse(s) to deliver, during one cycle, an inhalant having 160 ppm of nitric oxide for 30 minutes (the first time period). It is noted that other concentrations and other first time periods, which afford a nitric oxide-load of at least 80 ppm-hour per cycle, are also contemplated and encompassed by embodiment of the present invention.

By "intermittent breathing cycle-coordinated pulse delivery inhalation" it is meant that the infant is subjected to a gaseous mixture that contains the indicated concentration of nitric oxide intermittently, and thus inhales such a nitric oxide-containing gaseous mixture by breathing cycle-coordinated pulse delivery two or more times with intervals between each inhalation. The infant therefore inhales the nitric oxide-containing gaseous mixture, then stops inhaling a nitric oxide-containing gaseous mixture by breathing cycle-coordinated pulse delivery and inhales instead a gaseous mixture that does not contain the indicated concentration of nitric oxide (e.g., air), then inhales again the nitric oxide-containing gaseous mixture by breathing cycle-coordinated pulse delivery, and so on and so forth.

In some embodiments of this aspect of the present invention, "a nitric oxide-containing gaseous mixture" is used to describe a gaseous mixture that contains at least 160 ppm nitric oxide. The nitric oxide-containing mixture can comprise 160 ppm, 170 ppm, 180 ppm, 190 ppm, 200 ppm and even higher concentrations of nitric oxide. Other gaseous mixtures mentioned herein include less than 160 ppm nitric oxide or are being essentially devoid of nitric oxide, as defined herein.

In some embodiments "a nitric oxide-containing gaseous mixture" describes a gaseous mixture that delivers nitric oxide at 80 ppm-hour.

By "essentially devoid of nitric oxide" it is meant no more than 50 ppm, no more than 40 ppm, no more than 30 ppm, no more than 20 ppm, no more than 10 ppm, no more than 5 ppm, no more than 1 ppm and no more than ppb, including absolutely no nitric oxide.

According to some embodiments of the present invention, the intermittent breathing cycle-coordinated pulse delivery inhalation includes one or more cycles, each cycle comprising breathing cycle-coordinated pulse delivery inhalation of a gaseous mixture containing nitric oxide at the specified concentration (e.g., at least 160 ppm) for a first time period, which is also referred to herein as the nitric oxide-load per cycle, followed by inhalation of a gaseous mixture containing no nitric oxide for a second time period. According to some embodiments of the present invention, during the second period of time the infant may inhale ambient air or a controlled mixture of gases which is essentially devoid of nitric oxide, as defined herein.

In some embodiments, the first time period spans from 10 to 45 minutes, or from 20 to 45 minutes, or from 20 to 40 minutes, and according to some embodiments, spans about 30 minutes.

According to some embodiments of the present invention, the second time period ranges from 3 to 5 hours, or from 3 to 4 hours, and according to some embodiments the second time period spans about 3.5 hours.

According to some embodiments of the present invention, this inhalation regimen is repeated 1-6 times over 24 hours, depending on the duration of the first and second time periods.

In some embodiments, a cycle of intermittent breathing cycle-coordinated pulse delivery of nitric oxide, e.g., 160 ppm for 30 minutes followed by 3.5 hours of breathing no nitric oxide, is repeated from 1 to 6 times a day. According to some embodiments, the cycles are repeated 5 times a day.

In some embodiments, a cycle of intermittent breathing cycle-coordinated pulse delivery of nitric oxide, e.g., at nitric oxide-load of 80 ppm-hour per cycle, followed by 3.5 hours of breathing no nitric oxide, is repeated from 1 to 6 times a day. According to some embodiments, the cycles are repeated 5 times a day.

According to some embodiments of the present invention, the regimen of 1-5 cycles of intermittent breathing cycle-coordinated pulse delivery of nitric oxide per day is carried out for 1 to 7 days, or from 2 to 7 days, or from 3 to 7 days, or for 1, 2, 3, 4 or 5 successive weeks. According to some embodiments of the present invention, the intermittent breathing cycle-coordinated pulse delivery inhalation is effected during a time period of 14 days. However, longer time periods of intermittent nitric oxide administration as described herein, are also contemplated.

According to embodiments of the present invention, the nitric oxide-containing gaseous mixture, which the infant inhales during the first time period, is generated in-situ in an inhalation device which is configured to respond to the infant's breathing cycle such that nitric oxide is mixed into the inhalant in one or more pulses when the infant breaths in at a high rate, namely at the inhalation period of the breathing cycle. This mode of administration of nitric oxide by inhalation is referred to herein as "breathing cycle-coordinated pulse delivery inhalation".

In the context of embodiments of the present invention, the term "pulse" refers to a mode of administering nitric oxide, which is introduced into the inhalant in interrupted and concentrated doses during a predetermined period of time, referred to herein as the "pulse delivery period", wherein each pulse, effected during the pulse delivery period, spans a predetermined period of time, referred to herein as the "pulse-on period", and interrupted by a "pulse-off period".

According to embodiments of the present invention, the pulse delivery period starts during the inhalation period, after a period of time which is referred to herein as the "pulse delay period". According to some embodiments of the present invention, the pulse delivery period is typically shorter than the inhalation period, and the time between the end of the pulse delivery period and the end of the inhalation period is referred to herein as the "pulse cessation period".

According to some embodiments of the present invention, the inhalation device for delivering the breathing cycle-coordinated pulse delivery inhalation of gashouse nitric oxide is configured to detect the various phases of the breathing cycle, namely the onset of the inhalation and the exhalation periods, and can therefore coordinate the pulses with the breathing cycle such that the pulse delay period is coordinated to start as soon as the rate of intake increases at the onset of the inhalation period, and the pulse cessation period is coordinated to start with as soon as the rate of intake decreases close to the end of the inhalation period.

In some embodiments, the length of the various time periods in the breathing cycle-coordinated pulse delivery inhalation scheme is determined and/or calculated relative to the duration of the breathing cycle, namely in percent of the total duration of the breathing cycle, or parts thereof. For example, the duration of the inhalation period is determined by sensing the flow rate of the inhalant, and the pulse delay period is automatically set to 20% of the inhalation period. Consequently, the pulse delivery period can be set to 60% of the inhalation period, and the pulse cessation period is the remaining 20% of the inhalation period. The number of pulses, namely the pulse-on and pulse-off periods, can be set similarly according to the duration of the pulse delivery period. For example, the number of pulses can be set to one, namely a pulse that spans the entire duration of the pulse delivery period. This example may be suitable for an infant experiencing shortness of breath or any difficulty in respiration. Alternatively, in cases where the infant is breathing normally, the pulse-on period is set to 200-300 milliseconds (ms), and the pulse-off period is set to 100 ms, while the number of pulses is automatically set by the duration of pulse delivery period which is derived from the measured inhalation period.

In some embodiments, the pulse delay period ranges from 0 ms to 2500 ms. Alternatively, in some embodiments, the pulse delay period ranges from 0% to 80% of the inhalation period.

In some embodiments, the pulse cessation period ranges from 0 ms to 2500 ms. Alternatively, in some embodiments, the pulse cessation period ranges from 80% to 0% of the inhalation period.

In some embodiments, each the pulse-on periods individually ranges from 100 ms to 5000 ms. Alternatively, each the pulse-on periods individually ranges from 10% to 100% of the inhalation period.

In some embodiments, each the pulse-off period individually ranges from 0 ms to 2500 ms. Alternatively, each the pulse-off periods individually ranges from 0% to 200% of the pulse-on period.

In some embodiments, the method is based on a single pulse per inhalation period. In some embodiments, the single pulse is effected such that the pulse delivery period starts essentially as the inhalation period starts (pulse delay period is essentially zero), and ends essentially as the inhalation period ends (pulse cessation period is essentially zero). In other embodiments the method is effected by using a single pulse that starts after the inhalation period starts, and ends before the inhalation ends.

In some embodiments, the coordination of pulse delivery is set to deliver more than one pulse in succession during the pulse delivery period, until the device senses a decrease in the rate of intake close to the end of the inhalation period. In such embodiments, the device is set to interrupt each pulse-on period with a pulse-off period. In some embodiments, the device is set to deliver a predetermined number of pulses that ranges from 1 to 2, from 1 to 3, from 1 to 4, from 1 to 5, from 1 to 6, from 1 to 7, from 1 to 8, from 1 to 9, from 1 to 10, or from 1 to any number of pulses that can take place within the pulse delivery period as determined by any given breathing cycle. It is further noted that each of the pulses may span a different pulse-on period and be interrupted by a pulse-off period of different lengths.

The concentration of nitric oxide in the nitric oxide-containing gaseous mixture is controlled by the concentration of nitric oxide is introduced into the inhalant, the output by which nitric oxide is introduced into the inhalant, the duration of the pulse-on period and the number of pulses introduced into the inhalant during the pulse delivery period. According to some embodiments of the present invention, during the pulse delivery period the inhalant is essentially a nitric oxide-containing gaseous mixture which contains at least 160 ppm nitric oxide, or nitric oxide-load of 80 ppm-hour per cycle, while during the pulse delay period and the pulse cessation period the inhalant is essentially devoid of nitric oxide.

According to some embodiments, the method is effected by using more than one pulse, wherein the inhalant, which is produced by each of the pulses, delivers to the patient a different concentration of nitric oxide. For example, the method may be carried out by administering to the infant, during the pulse delivery period, three pulses, such that the inhalant that stems from the first pulse is characterized by an nitric oxide concentration of 160 ppm, the inhalant that stems from the second pulse is characterized by an nitric oxide concentration of 80 ppm, and the inhalant that stems from the first pulse is characterized by an nitric oxide concentration of 100 ppm. Hence, at least one pulse effects a concentration of at least 160 ppm. In other examples, some of the pulses may deliver an inhalant characterized by an nitric oxide concentration of more than 160 ppm.

Alternatively, the number of pulses, the concentration of nitric oxide in each of the pulses, and the duration of the first time period during which pulses are generated, are configured to deliver an nitric oxide-load per cycle of 80 ppm-hour.

As presented hereinabove, breathing cycle-coordinated pulse delivery inhalation allows the introduction of high concentrations of nitric oxide essentially during the periods of time in which the infant inhales at the highest in-breathing rate, thereby minimizing exposure of parts of the respiratory tract to high concentrations of nitric oxide. For example, since nitric oxide is introduced in pulses after the beginning of the inhalation period and before the end of the inhalation period, parts of the upper respiratory tract, the trachea and the some of the respiratory tree in the lungs which are not rich with alveolor capillaries, are only briefly exposed to high concentrations of nitric oxide due to the rate of inhalant intake, while the alveoli are exposed to this high concentrations of nitric oxide for a longer period of time.

According to some embodiments of the present invention, subjecting the infant to the method described herein is carried out by use of an inhalation device which can be any device which can deliver the mixture of gases containing nitric oxide, including but not limited to breathing cycle-coordinated pulse delivery to a respiratory organ of the subject. An inhalation device, according to some embodiments of the present invention, includes, without limitation, a stationary inhalation device comprising tanks, gauges, tubing, a mask, controllers, values and the likes; a portable inhaler (inclusive of the aforementioned components), a metered-dose inhaler, a respiration machine/system and an intubated inhalation/respiration machine/system.

Exemplary inhalation devices which may be suitable for the execution of any embodiment of any of the methods described herein, are provided, for example, by U.S. Provisional Patent Application Nos. 61/876,346 and 61/969,201, and U.S. Pat. Nos. 6,164,276 and 6,109,260, the contents of which are hereby incorporated by reference. Commercial inhalation devices which may be suitable for the execution of any of the methods described herein, include the INOpulse® DS-C developed by Ikaria Australia Pty Ltd, or the Ohmeda INOpulse Delivery System by Datex-Ohmeda.

An inhaler, according to some embodiments of the present invention, can generate spirometry data and adjust the treatment accordingly over time as provided, for example, in U.S. Pat. No. 5,724,986 and WO 2005/046426, the contents of which are hereby incorporated by reference. The inhaler can modulate the subject's inhalation waveform to target specific lung sites. According to some embodiments of the present invention, a portable inhaler can deliver both rescue and maintenance doses of nitric oxide at subject's selection or automatically according to a specified regimen.

According to some embodiments of the present invention, an exemplary inhalation device may include a delivery interface adaptable for inhalation by an infant. According to some embodiments of the present invention, the delivery interface includes a mask or a mouthpiece for delivery of the mixture of gases containing nitric oxide to a respiratory organ of the infant.

According to some embodiments of the present invention, the inhalation device further includes a nitric oxide analyzer positioned in proximity to the delivery interface for measuring the concentration of nitric oxide, oxygen and nitrogen dioxide flowing to the delivery interface, wherein the analyzer is in communication with the controller.

It is expected that other methods for treating an inflammatory disease or disorder by intermittent inhalation of nitric oxide at 160 ppm or more will be developed and the scope of the term treating an inflammatory disease or disorder by intermittent inhalation of nitric oxide is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

Potentiation of Antimicrobial Agents: In some embodiments, the present invention provides methods for potentiating antimicrobial agents (such as, for example, antibiotics and anti-fungal agents) which are used in the treatment of medical conditions and diseases associated with a pathogenic microorganism (such as, for example, bacterium or fungus); the methods include exposing the pathogenic microorganism cells to NO, thereby rendering these cells more sensitive to the antimicrobial agents. Without being bound by any particular theory, the methods as disclosed herein utilize the exposure of pathogenic microorganism cells to NO such that the pathogenic microorganism is rendered more sensitive towards antimicrobial agents and/or less capable of resisting antimicrobial agents, by depleting their innate defense mechanism against antimicrobial agents.

In some embodiments, the method for potentiating antimicrobial agents presented herein includes depletion of thiols in target cells by exposure of the target cells to nitric oxide. This method of exposure to NO enables the use of broad spectrum antibiotics and antimicrobial agents not only against drug sensitive pathogens, but also against drug resistant (MDR or XDR) microbial strains that have accumulated mutations in proteins previously targeted by specific drugs. This method of exposure to NO also broadens the effectiveness of antibiotics and antimicrobial agents against pathogens which have not been identified as susceptible to these agents prior to exposure to NO, namely rendering narrow-acting antimicrobial agents into broad-spectrum antimicrobial agents.

In some embodiments, the method presented herein is also useful for preventing, reducing and/or eliminating the formation or persistence of microbial biofilm by exposure of the biofilm to nitric oxide in combination with an antimicrobial or anti-biofilm formation agent (ABF agent). This method of exposure to NO increases the efficacy of antibiotics, antimicrobial and ABF agents to reduce and/or eliminate microbial biofilms which would be little or not affected thereby without the exposure to NO. Hence, herein and throughout, the description pertaining to treatment of a medical condition associated with a pathogenic microorganism is meant to encompass treatment against the formation of a microbial biofilm. For example, the method presented herein can be used effectively to treat tuberculosis, which is caused by *Mycobacterium tuberculosis* (Mtb) that has acquired point mutations that make Mtb resistant over the years to first line antibiotics. Furthermore, since these bacteria are intrinsically resistant to many readily available antimicrobial agents that are already used effectively against other bacterial infections, the method presented herein can weaken Mtb intrinsic resistance by depleting its intrinsic MSH levels, thereby revealing the potential for using these readily available antimicrobial agents against new MDR and XDR TB strains.

The present invention, in some embodiments thereof, relates to medicinal antimicrobial treatments, and more specifically, but not exclusively, to methods of potentiating antimicrobial agents and/or sensitizing or re-sensitizing antimicrobial-resistant microorganisms to an antimicrobial treatment, to thereby treat a variety of conditions associated with pathogenic microorganisms, as well as potentiate antimicrobial agents to prevent the formation or eradicate microbial biofilms.

The use of the currently practiced antimicrobial agents and therapies is severely limited, mainly by the development of resistance against these antimicrobial agents. The present inventors have surprisingly uncovered that nitric oxide exhibits antimicrobial sensitizing and/or re-sensitizing activity and is further characterized advantageously as an effective potentiator of antimicrobial agents even when used in concentrations lower than effective bactericidal levels, namely at concentrations and exposure times in which nitric oxide does not eradicate microorganisms. This potentiation by nitric oxide enables, for example, eradicating microorganisms with an antimicrobial agent at concentrations below those that typically eradicate the microorganisms by the antimicrobial agent without potentiation with nitric oxide and/or at exposure time shorter than those which typically eradicate the microorganisms by the antimicrobial agent without potentiation with nitric oxide.

It is known in the art that microbial resistance to an antimicrobial agent typically develops in a population of subjects treated with the antimicrobial agent, when a number of generations of the target microorganism infecting the population are exposed to the antimicrobial agent. During that exposure, the resistant cells survive (become resistant, wherein resistance has developed) may infect other subjects. Treatment of these subjects, which have been infected with the resistant microorganism with the same antimicrobial agent, is no longer effective. It is noted than in some cases resistance may also develop in one subject during a treatment with an antimicrobial agent, typically the treatment is prolonged and/or base sub-optimal doses of the agent. According to some embodiments of the present invention, the combination treatment using nitric oxide and an antimicrobial agent, as presented herein, enables treatment against microorganisms with that antimicrobial agent even when the microorganisms have already developed resistance towards that same antimicrobial agent. The presently provided methods also prevent selective pressure for resistant microorganisms.

The use of the currently practiced antimicrobial agents is also severely limited in fighting microbial biofilms, mainly due to the protection conferred to the microbial cells by the coat of extra-cellular polysaccharide secretion. Exposure of microbial biofilm to nitric oxide, in combination to exposure of the biofilm to an antimicrobial agent, can be utilized against the microbial biofilm compared to the anti-biofilm efficacy of the antimicrobial agent when used without nitric oxide.

Nitric oxide was found highly effective when administered together with an antibiotic, in eradicating resistant bacteria, and was shown capable of re-sensitizing bacteria which became resistant to an antibiotic, such that when the same antibiotic is used, it effectively eradicates the bacteria. Nitric oxide may also be used for preventing the emergence of resistance, when used in combination with an antibiotic, in microorganisms that are expected to develop resistance to the antibiotic, by preventing selective pressure for resistant microorganisms.

Nitric oxide is therefore highly useful in treating conditions associated with resistant bacteria and in reducing or eradicating microbial biofilms, by (i) being effective when administered in combination with an antimicrobial treatment that would otherwise not be effective; (ii) being effective in preventing an emergence of resistance to an antimicrobial agent, when administered in combination with the antimicrobial agent; and (iii) being effective in resensitizing a microorganism to an antimicrobial agent, upon uncovering emergence of resistance to the antimicrobial agent used.

Nitric oxide is also highly useful in reducing or eradicating microbial biofilms when administered or applied in combination with an anti-biofilm treatment that would otherwise not be effective. Hence, m the context of embodiments of the present invention, the term "antimicrobial agent" is meant to encompass anti-biofilm formation agents, or used synonymously with the term "anti-biofilm formation agent".

Therefore the present invention provides methods for rendering microorganisms more sensitive to antimicrobial agents that have not been effective or lost their effectiveness thereagainst; the method is effected by exposing the microorganisms to nitric oxide. Without being bound by any particular theory, it is assumed that exposing microorganisms to NO according to embodiments of the method presented herein weakens the first line of defense of microorganisms against xenobiotics including, free radicals, toxins, antibiotics and other antimicrobial agents. This line of microorganisms' defense is based on the presence of low molecular weight thiols in the target cells, thus the beneficial effect of the method presented herein is afforded by reducing and depleting the level of these thiols by nitric oxide, thereby 30 rendering the target cells more sensitive to a wider range of antimicrobial agents.

The Method:

In general, embodiments of the present invention employ the antimicrobial potentiating activity of nitric oxide, as it is described hereinabove in the context of depleting the defense mechanisms of microbe. The phrase "antimicrobial potentiating activity", as used herein in the context of embodiments of the present invention, defines a characteristic of the method which relates to three entities, namely (i) nitric oxide, (ii) an antimicrobial agent, and (iii) a microorganism which is either known to be insensitive (unsusceptible, resistant) to the antimicrobial agent, or became or may become resistant to the antimicrobial agent in the sense that the microorganism was susceptible to the antimicrobial agent but is no longer sensitive to the antimicrobial agent as a result of development of resistance to the antimicrobial agent in that strain of microorganism. Thus, in the context of embodiments of the present invention, the existence on an antimicrobial potentiating activity allows nitric oxide to act in synergy, and/or endow potency to, and/or potentiate and/or re-potentiate an antimicrobial agent against a microorganism by, sensitizing or re-sensitizing the microorganism to the antimicrobial agent.

It is noted herein that in the context of the method, as well as all other aspects of the invention presented herein, an microbial resistance to any given antimicrobial agent can be innate or acquired, namely the microorganism may be innately insensitive to the antimicrobial agent by virtue of its chemical and biological nature, or become insensitive to the antimicrobial agent as a result of exposure of previous generations of the microorganism to the antimicrobial agent. For example, antimicrobial resistance may emerge against an antimicrobial agent in a population of subjects having a medical condition as a result of treating the population with that antimicrobial agent. A subject that has been infected with these resistant microorganism can be treated with the same antimicrobial agent by carrying out the method presented herein, namely by administering a potentiating, sensitizing or re-sensitizing effective amount of nitric oxide in combination with a therapeutically effective amount of that antimicrobial agent. The method presented herein is effective in such cases regardless of the mechanism by which the microorganism acquired the resistance towards the antimicrobial agent.

Thus, according to an aspect of embodiments of the present invention, there is provided a method of treating a subject having a medical condition associated with a pathogenic microorganism, which is effected by:

Step (i)—administering to the subject a potentiating effective amount of nitric oxide or a nitric oxide releasing compound; and Step (ii)—administering to the subject a therapeutically effective amount of the antimicrobial agent.

In some antimicrobial treatments, the resistance of the target microorganism is oftentimes uncovered after finding that the antimicrobial agent, which is typically effective thereagainst, is no longer effective. Hence, according to another aspect of embodiments of the present invention, there is provided a method of treating a subject having a medical condition associated with a pathogenic microorganism in which an antimicrobial resistance has been uncovered following treating said subject with said antimicrobial agent, the method is effected by:

Step (i)—administering to the subject, following a treatment with said antimicrobial agent and uncovering said antimicrobial resistance, a re-sensitizing effective amount of nitric oxide; and Step (ii)—administering to the subject a therapeutically effective amount of the antimicrobial agent.

According to embodiments pertaining to this aspect of the invention, the antimicrobial agent is no nitric oxide and the re-sensitizing effective amount of nitric oxide is lower than the therapeutically effective amount of nitric oxide with respect to the microorganism.

By "potentiating", it is meant that a microorganism that was not sensitive or mildly sensitive (unsusceptible) to an antimicrobial agent (i.e., narrow spectrum antibiotics), becomes sensitive (susceptible) to that antimicrobial agent. In such cases it can be said that the method presented herein renders some antimicrobial agents effective against some microorganism species which were insensitive to the antimicrobial agent when used traditionally, namely when used without effecting Step (i) of the method as presented herein.

By "re-sensitizing" or "re-potentiating", it is meant that a microorganism that normally is sensitive (susceptible) to a treatment with antimicrobial agent, is found resistant to such a treatment for any reason, is turned to be sensitive (susceptible) again to such a treatment.

As used herein, the phrase "therapeutically effective amount" describes an amount of an active agent being administered, which is required to substantially reduce or essentially eradicate a microorganism in a subject, thereby relieve to some extent one or more of the symptoms of the condition being caused by the microorganism, by being administered at an amount that is harmful to the target microorganism, namely a bactericidal level or otherwise a level that substantially inhibits the growth of the microorganism in the subject, or in some embodiments essentially eradicates the microorganism in the subject. In the context of the present embodiments, the phrase "therapeutically effective amount" describes the amount of an antimicrobial agent being administered and/or re-administered in combination with nitric oxide, which is typically lower than the amount required to achieve similar results without the combination with nitric oxide. As used herein, a "therapeutically effective amount" also encompasses the duration of exposure of microorganism to a given antimicrobial agent.

As used herein, the phrase "potentiating effective amount" describes an amount of nitric oxide which is sufficient to confer antimicrobial potentiating activity, thereby potentiate an antimicrobial agent towards a microorganism, or sensitize a microorganism towards an antimicrobial agent. A potentiating effective amount of nitric oxide is defined as insufficient to eradicate a microorganism (kill at least 50%, 70%, 80% or 100% of the microorganism) in a subject.

As used herein, the phrase "re-sensitizing effective amount" describes an amount of nitric oxide which is sufficient to reverse a resistance which has emerged in a microorganism against an antimicrobial agent. A re-sensitizing effective amount of nitric oxide is defined as insufficient to eradicate a microorganism (kill at least 50%, 70%, 80% or 100% of the microorganism) in a subject. In some embodiments, the phrase "re-sensitizing effective amount" describes an amount of nitric oxide which is sufficient to reverse, or prevent the emergence of resistance in the pathogenic microorganism causing a medical condition.

It should be noted herein that while nitric oxide may exhibit microbicidal activity per-se, the potentiating or re-sensitizing effective amount of nitric oxide, according to embodiments of the present invention, is substantially different than the microbicidal amount (the therapeutically effective amount) of nitric oxide in the sense that a potentiating or re-sensitizing effective amount of nitric oxide is not expected to be sufficient to cause destruction or disruption to the life-cycle of the target microorganism(s) when used exclusively, without the presence of another antimicrobial agent. In other words, in the context of embodiments of the present invention, the potentiating, sensitizing or re-sensitizing effective amount of nitric oxide is lower than the therapeutically effective amount of nitric oxide.

According to some embodiments of the present invention, nitric oxide may exhibit an antimicrobial therapeutic activity with respect to the pathogenic microorganism. A potentiating or re-sensitizing effective amount of nitric oxide is typically lower than the therapeutically effective amount of nitric oxide when used as an antimicrobial agent against the microorganism causing the condition to be treated.

Thus, according to some embodiments of the present invention, the potentiating or resensitizing effective amount of nitric oxide is lower than the therapeutically effective amount of nitric oxide with respect to the microorganism to be eradicated if/when nitric oxide is administered by itself per-se.

The efficacy of any antimicrobial agent is oftentimes referred to in terms of minimal inhibitory concentration units, or MIC units. A MIC is the lowest concentration of an antimicrobial agent, typically measured in micro-molar ($\mu$M) or micrograms per milliliter ($\mu$g/ml) units, which can inhibit the growth of a microorganism after a period of incubation, typically 24 hours. MIC values are used as diagnostic criteria to evaluate resistance of microorganisms to an antimicrobial agent, and for monitoring the activity of an antimicrobial agent in question. MICs are determined by standard laboratory methods, as these are described and demonstrated in the Examples section that follows. Standard laboratory methods typically follow a standard guideline of a reference body such as the Clinical and Laboratory Standards Institute (CLSI), British Society for Antimicrobial Chemotherapy (BSAC) or The European Committee on Antimicrobial Susceptibility Testing (EUCAST). In clinical practice, the minimum inhibitory concentrations are used to determine the amount of antimicrobial agent that the subject receives as well as the type of antimicrobial agent to be used.

Thus, in some embodiments, a potentiating or re-sensitizing effective amount of nitric oxide is less than 1 MIC with respect to nitric oxide. In some embodiments, a potentiating or re-sensitizing effective amount of nitric oxide ranges from 1 MIC to 1/10 MIC. In some embodiments, the potentiating or re-sensitizing effective amount of nitric oxide ranges from 1/2 MIC to 1/8 MIC.

Medical Conditions:

In the context of embodiments of the present invention, the phrase "a medical condition associated with a pathogenic microorganism" is meant to encompass any medical condition which is caused, directly or indirectly, by the presence of a microorganism in or on a subject. The phrase "a medical condition associated with a pathogenic microorganism" therefore encompasses conditions associated with prokaryotic organisms, gram-negative bacteria, gram-positive bacteria, eubacteria, archaebacteria, eukaryotic organisms, yeast, fungi, algae, protozoa, and/or other parasites.

Medical conditions associated with a pathogenic microorganism include, according to embodiments of the present invention, infections, infestation, contaminations and transmissions by or of pathogenic microorganism. In general, a disease causing infection is the invasion into the tissues of a host organism by pathogenic microorganisms. The invasion of body tissues by parasitic worms and other higher pathogenic organisms is commonly referred to as infestation.

Invading organisms such as bacteria produce toxins that damage host tissues and interfere with normal metabolism; some toxins are actually enzymes that break down host tissues. Other bacterial substances may inflict their damage by destroying the host's phagocytes, rendering the body more susceptible to infections by other pathogenic microorganisms. Substances produced by many invading organisms cause allergic sensitivity in the host. Infections may be spread via respiratory droplets, direct contact, contaminated food, or vectors, such as insects. They can also be transmitted sexually and from mother to fetus.

Diseases caused by bacterial infections typically include, for non-limiting examples, actinomycosis, anthrax, aspergillosis, bacteremia, bacterial skin diseases, bartonella infections, botulism, brucellosis, burkholderia infections, campylobacter infections, candidiasis, cat-scratch disease, chlamydia infections, cholera, clostridium infections, coccidioidomycosis, cryptococcosis, dermatomycoses, diphtheria, ehrlichiosis, epidemic louse borne typhus, *Escherichia coli* infections, fusobacterium infections, gangrene, general infections, general mycoses, gonorrhea, gram-negative bacterial infections, gram-positive bacterial infections, histoplasmosis, impetigo, klebsiella infections, legionellosis, leprosy, leptospirosis, listeria infections, lyme disease, malaria, maduromycosis, melioidosis, mycobacterium infections, mycoplasma infections, necrotizing fasciitis, nocardia infections, onychomycosis, ornithosis, pneumococcal infections, pneumonia, pseudomonas infections, Q fever, rat-bite fever, relapsing fever, rheumatic fever, rickettsia infections, Rocky-mountain spotted fever, salmonella infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, vibrio infections, yaws, yersinia infections, *Yersinia pestis* plague, zoonoses and zygomycosis.

Examples of microbial infections which are effectively treated with the methods presented herein include, without limitation, typical gram-positive bacterial infections such as staphylococcal infections and streptococcal infections, which are treatable by nitric oxide combined with penicillin or cephalosporings. Typical gram-negative bacterial infections such as klebsiella, *E. coli* and *Pseudomonas* spp infections are treatable by nitric oxide combined with penicillin cephalosporins and quinolones.

Medical conditions associated with fungi (fungal infections) which are treatable by the methods and compositions presented herein include, without limitation, endemic fungal infections, opportunistic fungal infections, histoplasmosis histoplasma associated with capsulatum, coccidioidomycosis associated with *coccidioides immitis*, blastomycosis blastomyces associated with dermatitidis, paracoccidioidomycosis paracoccidioides associated with brasiliensis, candidiasis associated with *candida* spp., aspergillosis associated with *aspergillus* spp., mucormycosis associated with *mucor* spp., infections associated with absidia, infections associated with *rhizopus* spp., and cryptococcosis associated with *Cryptococcus neoformans*.

As stated hereinabove, treating a medical condition by the method presented herein, as well as all other aspects of the invention, is meant to encompass the prevention, reduction or eradication of a microbial biofilm.

Synergism:

According to embodiments of the present invention, the therapeutically effective amount of the antimicrobial agent administered in Step (ii) is notably lower than the effective amount of that antimicrobial agent when administered without performing Step (i), as provided herein. In other words, the efficacy of an antimicrobial agent increases notably as a result of administering nitric oxide to the subject, thereby constituting a synergistic effect of the treatment with nitric oxide. Nitric oxide may already be cleared from the subject's systems or the cells of the pathogenic microorganism, while the effect nitric oxide on the defense mechanisms of the pathogen still lingers, thereby rendering the antimicrobial agent more efficacious thereagainst.

Synergism is also exhibited when using the methods presented herein against biofilm formation.

Modes of Carrying Out the Method

In general, the method is effected by Step (i) in which the cells of the target microbial pathogen inflicting the medical condition in the subject, are exposed to nitric oxide in an amount, and for a period of time, which are sufficient to substantially reduce or deplete low molecular weight thiols in the target cells. The method is further effected by Step (ii) in which an antimicrobial agent is administered to the subject to substantially eradicate the pathogenic microorganism in the subject.

In some of any of the embodiments described herein, the time period during which the subject is treated with NO, namely the duration of Step (i), correlates to the latent period, which is defined as the time period during which low molecular weight thiols in the target pathogenic cells are present in an amount that allows the cells to resist, at least to some extent, the effect of an antimicrobial agent. The duration of the latent period depends on the species/strain of the target pathogenic cells, the amount, distribution and location of the pathogenic cells in the subject, the mode of administration of NO and the effective concentration of the NO which is administered to the subject. For list of latent periods measured in vitro for a variety of bacterial species/strains, as well as the time period at which a 2.5-fold reduction in microbial load ($-2.5 \text{ Log}_{io}$) and the eradication of the microbes (LD100), see Table 4 in the Examples section that follows below.

According to some embodiments, the duration of Step (i) is essentially equal to the duration of the latent period. According to some embodiments, the duration of Step (i) is longer than the latent period by at least 10%, 20%, 50% or at least 100%, and in some embodiments the latent period is longer than the duration of Step (i) by less than 50%, 20% or less than 10%.

According to some embodiments, Step (i) is effected prior to Step (ii), which follows subsequently, thereby allowing the latent period to substantially elapse before introducing the antimicrobial agent to the subject. In some embodiments, the delivery and distribution of nitric oxide to the target cells in the subject is such that Step (ii) is effected after an intermission between Step (i) and Step (ii) so as to allow the latent period to elapse.

According to some embodiments, Step (i) is effected concurrently with Step (ii), thereby allowing the antimicrobial agent to be delivered and distributed in the subject while the latent period elapses. In some embodiments, the delivery and distribution of the antimicrobial agent is such that Step (ii) is effected prior to Step (i), thereby allowing the antimicrobial agent to reach the target cells at the end of the latent period.

The methods presented herein are effected by administering to a subject NO in the form of gaseous NO (gNO) in a carrier gas, or in the form of a nitric oxide (NO) donating/releasing compound, as the term is defined herein.

Use of Nitric Oxide by Inhalation:

Since NO is a gas, it may be administered directly by inhalation. The mode of administration of gNO, which is suitable in the context of the present embodiments, includes topical administration by exposure of the subject (whole body or parts thereof) to an NO-containing gas mixture, and systemic administration by inhalation of the NO-containing gas mixture.

In the context of embodiments of the present invention, the concentration of NO in the NO-containing gas mixture ranges from 80 ppm to 5000 ppm, mostly depending on the more of administration, however, other ranges of concentrations are contemplated according to embodiments of the present invention. For example, the concentration of NO in the NO-containing gas mixture is at least about 80 ppm, 90 ppm, 100 ppm, 120 ppm, 140 ppm, 160 ppm, 180 ppm, 200 ppm, 240 ppm, 280 ppm, 320 ppm, 400 ppm, 500 ppm or 1000 ppm.

It is noted that NO is administered while considering toxicity of NO when administered by inhalation. For example, safety of the subject may be achieved by administering NO by inhalation while monitoring the levels of $NO_2$ in the inhalant and blood methemoglobin (SpMET) levels, keeping the $NO_2$ level below, e.g., 5 ppm and preferably 2.5 ppm, and the SpMET level does not exceed 5%, and preferably does not exceed 1%.

According to some embodiments of the present invention in which the NO-containing gas mixture is meant for inhalation by the subject, the term "NO-containing gas mixture" refers to a gaseous mixture of NO, oxygen and air or nitrogen, which is characterized by a predetermined, controlled and consistent concentration of NO and 0 2 mixed together in a carrier gas (i.e., air or nitrogen).

According to some embodiments of the present invention, Step (i) may be carried out in one or more cycles, wherein each cycle is characterized by continuous inhalation of the NO-containing gas mixture at the specified NO concentration (e.g., from about 80 to about 200 ppm NO, or at least about 160 ppm) for a first time period, followed by inhalation of air or a gaseous mixture containing no gNO for a second time period. According to some embodiments of the present invention, during the second period of time the subject may inhale ambient air or a controlled mixture of gases which is essentially devoid of NO, referred to herein as an carrier mixture.

In some embodiments, the first time period spans from 10 to 45 minutes, or from 20 to 45 minutes, or from 20 to 40 minutes, and according to some embodiments, spans about 30 minutes.

According to some embodiments of the present invention, the second time period ranges from 3 to 5 hours, or from 3 to 4 hours, and according to some embodiments the second time period spans about 3.5 hours.

According to some embodiments of the present invention in which the NO-containing gas mixture is meant for topical administration to the subject which does not include inhaling the mixture, the term "NO-containing gas mixture" refers to a gaseous mixture of NO and a carrier gas, which is characterized by a predetermined, controlled and consistent concentration of NO.

Use of NO-Releasing Compounds:

In cases where administration of the NO by inhalation of gNO is less effective, as may by in cases nitric oxide does not reach the target organ and/or biological system, and as may be cases associated with both biochemical and medical complications, including, for example, methemoglobinemia and direct pulmonary injury, nitric oxide administration is carried out using a nitric oxide precursor or an NO-releasing compound, as defined herein. Thus, according to embodiments of the present invention, in Step (i) NO is delivered and generated in situ by means of a prodrug. NO prodrugs are known as NO-donors, which produce NO spontaneously under physiological conditions, and/or metabolized by enzymatic mechanisms so as to generate or release active NO. Hence, according to embodiments of the present invention, NO-donors, which are also referred to interchangeably, herein and in the art, as NO prodrugs or NO-releasing compounds, are pharmacologically active substances that spontaneously release, or are metabolized to, NO or its redox congeners. In some embodiments, the NO-releasing compound produces nitric oxide spontaneously under physiological conditions.

The mode of administration of nitric oxide precursor in the form of an NO-releasing compound, which is suitable in the context of the present embodiments, includes topical administration and systemic administration, and include, without limitation, oral administration, rectal administration, intravenous administration, topical administration (including ophtalmically, vaginally, rectally, intranasally), intranasal administration, intradermal administration, transdermal administration, subcutaneous administration, intramuscular administration, intraperitoneal administration, administration by inhalation or administration by intrathecal catheter.

As used herein, the terms "nitric oxide (NO) donating/releasing compound" or "NO-releasing compound" refer to an organic or inorganic compound capable of releasing nitric oxide. In some embodiments, the NO-releasing compound is a small molecule, generally described as molecule with a molecular weight of less than 600 g/mol.

Some classes such as the organic nitrates have been used for decades therapeutically as NO-releasing compounds. Some non-limiting examples of organic NO-releasing compounds include organic esters of nitric acid (nitrate esters), such as, for example, nitroglycerin, ethylene glycol dinitrate, isopropyl nitrate, glyceryl 1-mononitrate, glyceryl 1,2-dinitrate, glyceryl 1,3-dinitrate, nitroglycerine, butane-1,2,4-triol trinitrate, erythrityl tetranitrate, pentaerythrityl tetranitrate and isosorbide mononitrate, which can, in turn, comprise isosorbide 2-mononitrate, isosorbide 5-mononitrate and isosorbide dinitrate.

Diazeniumdiolates, also known as "NONOates" (1-substituted diazen-1-ium-1,2-diolates, e.g., DETA NONOate), constitute another class of NO-releasing compounds which contain the —[N(O)NO]— functional group. NO-releasing compounds that bear the diazeniumdiolate group have been disclosed as NO-releasing agents in, e.g., U.S. Pat. Nos. 4,954,526, 5,039,705, 5,155,137 and 5,208,233, all of which are incorporated herein by reference. An advantage to these NO-releasing compounds is their wide range of half-lives depending upon the structure of the amine bearing the diazeniumdiolate group.

C-based diazeniumdiolate molecules which release NO have been disclosed in, e.g., U.S. Pat. Nos. 6,232,336, 6,511,991 and 6,673,338, all of which are incorporated herein by reference.

Non-diazeniumdiolate forms of NO-releasing compounds including S-nitroso compounds, have also been described in, e.g., U.S. Pat. Nos. 5,536,723 and 5,574,068, and C-nitroso compounds in, e.g., U.S. Pat. No. 6,359,182, all of which are incorporated herein by reference.

NO-releasing compounds, according to embodiments of the present invention include NO-releasing imidates, methanetrisdiazeniumdiolate, and a bisdiazeniumdiolate derived from 1,4-benzoquinone dioxime, as well as NO-releasing imidates and thioimidates of the following as disclosed in U.S. Pat. No. 6,673,338, which is incorporated herein by reference.

Other NO-releasing compounds, which are suitable in the context of embodiments of the present invention, are disclosed, for example, in EP 1004294 and U.S. Pat. Nos. 7,569,559, 7,763,283, 7,829,553, 8,093,343, 8,101,589 and 8,101,658, all of which are incorporated herein by reference.

According to some embodiments the potentiating or re-sensitizing effective amount of the NO-releasing compound (s) ranges from about 0.01 mg/kg body (mg of the NO-releasing compound per 1 kg of the subject's body weight) to about 50 mg/kg body weight.

Pathogenic Microorganism:

Herein throughout, the phrase "pathogenic microorganism" is used to describe any microorganism which can cause a disease or disorder in a higher organism, such as mammals in general and a human in particular. The pathogenic microorganism may belong to any family of organisms such as, but not limited to prokaryotic organisms, gram-negative bacteria, gram-positive bacteria, eubacterium, archaebacterium, eukaryotic organisms, yeast, fungi, algae, protozoa, and other parasites. Non-limiting examples of pathogenic microorganism are *Plasmodium falciparum* and related malaria-causing protozoan parasites, *Acanthamoeba* and other free-living amoebae, *Aeromonas hydrophila, Anisakis* and related worms, and further include, but not limited to *Serracia* sp., *Enterobacter* sp., *Acinetobacter* sp *Acinetobacter baumanii, Ascaris lumbricoides, Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica, certain strains of Escherichia coli, Eustrongylides, Giardia lamblia, Klebsiella pneumoniae, Listeria monocytogenes, Nanophyetus, Mycobacterium smegmatis, Mycobacterium tuberculosis, Mycobacterium avium intracellularae, Plesiomonas shigelloides, Proteus mirabilis, Pseudomonas aeruginosa, Salmonella, Serratia odorifera, Shigella, Staphylococcus aureus, Stenotrophomonas maltophilia, Streptococcus, Trichuris trichiura, Vibrio cholerae, Vibrio parahaemolyticus, Vibrio vulnifzcus* and other *vibrios, Yersinia enterocolitica, Yersinia pseudotuberculosis* and *Yersinia kristensenii*.

Accordingly, a condition associated with a pathogenic microorganism describes an infectious condition that results from the presence of the microorganism in a subject. The infectious condition can be, for example, a bacterial infection, a fungal infection, a protozoal infection, and the like.

Treating a condition associated with a pathogenic microorganism describes means for preventing, reducing, ameliorating or abolishing symptoms of the infectious condition. The treatment is effected typically by inhibiting the growth and/or eradicating the pathogenic microorganism.

Antimicrobial Agent:

The phrase "antimicrobial agent", as used herein encompasses all antimicrobial agents while excluding nitric oxide as an antimicrobial agent per-se. According to the definition of microorganism presented hereinabove, the phrase "antimicrobial agent" encompasses antibiotic agents (also referred to herein as antibiotic) as well as anti-fungal, anti-protozoan, anti-parasitic agents and like.

According to some embodiments, the antimicrobial agent is an antibiotic agent. In general, but without being bound to any particular theory, the mechanism of the antimicrobial activity of an antimicrobial agent, according to the embodiments of the present invention, is different that the mechanism of the activity of the polymers, according to the embodiments of the present invention.

It is noted herein that the phrase "antimicrobial agent" is meant to encompass any combination of antimicrobial agents, and further noted that in the context of embodiments of the present invention, nitric oxide is excluded from the scope of the phrase "antimicrobial agent".

An example of a known combination of several antimicrobial agents, which is regarded in the context of embodiments of the present invention as "an antimicrobial agent", is the combination of penicillin or cephalosporin with an addition of aminoglycoside such as gentamicin.

Non-limiting examples of antimicrobial agents that are suitable for use in this context of the present invention include, without limitation, mandelic acid, 2,4-dichlorobenzenemethanol, 4-[bis(ethylthio)methyl]-2-methoxyphenol, 4-epi-tetracycline, 4-hexylresorcinol, 5,12-dihydro-5,7,12, 14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammoniumsulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, avermycin, azanidazole, azidamfenicol, azidocillin, azithromycin, azlocillin, aztreonam, bacampicillin, bacitracin, bacitracin zmc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefmenoxime, cefinetazole, cefinetazole sodium, cefininox, cefminox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibrompropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin magnesium, flucloxacillin sodium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin cla, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin AS, leucomycin A6, leucomycin A7, leucomycin A8, leucomycin A9, levofloxacin, lincomycin, lincomycin hydrochloride, linezolid, liranaftate, 1-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin c, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin a, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, omidazole, orthophenylphenol, oxacillin, oxacillinsodium, oxiconazole, oxiconazole nitrate, oxoferin, oxolinic acid, oxychlorosene, oxytetracycline, oxytetracycline calcium, oxytetracycline hydrochloride, pampenem, paromomycm, paromomycm sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium-tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin Bl, polynoxylin, povidone-iodine, propamidin, propenidazole, propicillin, propicillin potassium, propionic acid, prothionamide, protiofate, pyrazinamide, pyrimethamine, pyridomycin, pyrithi on, pyrrolnitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin b, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarbamide, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfi somidine, sulfisoxazole, sulfisoxazole acetyl, sulfonamides, sultamicillin, sultamicillin tosilate, tacrolimus, talampicillin 15 hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, 20 thiomersal, thiram, thymol, tibezonium iodide, ticarcillin, ticarcillin-clavulanic acid mixture, ticarcillin disodium, ticarcillin monosodium, tilbroquinol, tilmicosin, tinidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibomol and zinc undecylenate.

Antifungal drugs, which are usefully used in any other the aspects of the present inventions, include without limitation, polyenes, amphotericin B, liposomal amphotericin, nystatin, and pimaricin; azoles, fluconazole, itraconazole, ketoconazole, itraconazole, voriconazole, posaconazole; achinocandins, such as anidulafungin, caspofungin and micafungin;

allylamines and morpholines, such as naftifine and terbinafine and amorolfine; antimetabolites such as 5-fluorocytosine.

In some embodiments, the antimicrobial agent is an antibiotic. Exemplary antibiotics include, but are not limited to oxacillin, piperacillin, penicillin G, ciprofloxacin, erythromycin, tetracycline, gentamicin vancomycin and methicillin. These antibiotics are known to be associated with emergence of resistance thereto.

Pharmaceutical Composition:

In any of the methods described herein, nitric oxide, as gaseous NO or in the form of a NO-releasing compound, and/or the antimicrobial agent can be administered as a part of a pharmaceutical composition, which further comprises a pharmaceutical acceptable carrier, as described herein.

In embodiments where Step (i) and Step (ii) of the method presented hereinabove are not effected concomitantly, the pharmaceutical composition comprises two or more parts, wherein at least one part comprises nitric oxide and another part comprises the antimicrobial agent.

In embodiments wherein NO is inhaled or otherwise used as a gas, and the antimicrobial agent is administered as a solid, a liquid, a paste an ointment or a suspension/emulsion, the pharmaceutical composition comprises at least one gaseous part for nitric oxide and another nongaseous part for the antimicrobial agent. The carrier in the part comprising nitric oxide can be selected according to the mode of administration (inhalation or topical administration).

In embodiments wherein NO is administered as an NO-releasing compound, nitric oxide and/or the antimicrobial agent can be administered via any administration route, including, but not limited to, orally, by inhalation, or parenterally, for example, by intravenous drip or intraperitoneal, subcutaneous, intramuscular or intravenous injection, or topically. The carrier for any part of the composition is selected suitable to the selected route of administration.

According to another aspect of the present invention, there is provided a use of an antimicrobial agent in the manufacture of a medicament, which further comprises nitric oxide, for treating a medical condition associated with a pathogenic microorganism, as described for the method of treatment presented hereinabove. Alternatively, there is provided a use of nitric oxide in the manufacture of a medicament, which further comprises an antimicrobial agent, for treating a medical condition associated with a pathogenic microorganism, as described for the method of treatment presented hereinabove.

According to embodiments of the invention, the antimicrobial agent and/or its amount is selected such that when a potentiating or a re-sensitizing effective amount of nitric oxide is used, the therapeutically effective amount of the antimicrobial agent being substantially lower than a therapeutically effective amount of antimicrobial agent when used without nitric oxide. As in some other aspects presented herein, and according to some embodiments, nitric oxide can be used in combination with the antimicrobial agent, which can then be administered concomitant with or subsequent to administering nitric oxide.

Hence, according to another aspect of embodiments of the invention, there is provided a pharmaceutical composition which comprises, as active ingredients, a sensitizing or resensitizing effective amount of nitric oxide, a therapeutically effective amount of an antimicrobial agent and a pharmaceutically acceptable carrier. According to some embodiments, the composition is packaged in a packaging material and identified in print, in or on the packaging material, for use in the treatment of a medical condition associated with a pathogenic microorganism. According to other embodiments, the composition is packaged in a packaging material and identified in print, in or on the packaging material, for use in the treatment of a medical condition associated with a resistant pathogenic microorganism, as described hereinabove.

As used herein the phrase "pharmaceutical composition" or the term "medicament" refer to a preparation of nitric oxide and one or more antimicrobial agents as described herein, with other chemical components such as pharmaceutically acceptable and suitable carriers and excipients. The purpose of a pharmaceutical composition is to facilitate administration of nitric oxide and/or the antimicrobial agent to a subject.

Hereinafter, the term "pharmaceutically acceptable carrier" refers to a carrier or a diluent that does not cause significant irritation to an organism and does not abrogate the biological activity and properties of the administered compound. Examples, without limitations, of nongaseous carriers include air, nitrogen, agron and other carrier gases which are substantially inert towards nitric oxide and/or the antimicrobial agent if administered as an inhaled powder, vapors or a gas. Examples of non-gaseous carriers include, without limitations, propylene glycol, saline, emulsions and mixtures of organic solvents with water.

Herein the term "excipient" refers to an inert substance added to a pharmaceutical composition to further facilitate administration of a compound. Examples, without limitation, of 5 excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, PA, latest edition, which is incorporated herein by reference.

Any part of the pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Any part of a pharmaceutical composition for use in accordance with embodiments of the invention may be formulated in conventional manner using one or more pharmaceutically acceptable carriers comprising excipients and auxiliaries, which facilitate processing of any form of nitric oxide and any form of the antimicrobial agents into preparations which can be used pharmaceutically. Proper formulation is dependent upon the route of administration chosen.

Toxicity and therapeutic efficacy of the antimicrobial agents and potentiating or re-sensitizing efficacy of nitric oxide described herein can be determined by standard pharmaceutical procedures in experimental animals, e.g., by determining the MIC, $EC_{50}$, the $IC_{50}$, $LD_{50}$ (lethal dose causing death in 50% of the tested animals) and/or the $LD_{100}$ for a any combination of antimicrobial agent(s) and nitric oxide. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1). In general, the dosage is related to the efficacy of the active ingredient which, in the context of embodiments of the invention, is related to its minimal inhibitory concentration (MIC) and the particular pharmacokinetics and pharmacology thereof for absorption, distribution, metabolism, excretion and toxicity (ADMETox) parameters. For antimicrobial agents, a therapeutically effective amount is oftentimes about ten-fold the MIC of the antimicrobial agent. The potentiating or re-sensitizing effective amount of nitric oxide is lower than one MIC unit pertaining to nitric oxide and any given microorganism, and the therapeutically effective amount of any given antimicrobial agent used in combination with nitric oxide as described herein, may be equal or lower than one MIC unit pertaining to the antimicrobial agent and any given microorganism.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for 30 administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising any form of nitric oxide, either alone or in combination with an antimicrobial agent, formulated in a compatible pharmaceutical carrier may also be prepared, placed in an appropriate container, and labeled for treatment of an indicated condition, as is detailed herein.

A Pharmaceutical Kit:

As presented hereinabove, nitric oxide is directed at uses in combination with antimicrobial agents, and as further presented, the two active components may be administered concomitantly or sequentially as separate compositions. Hence, there is an advantage in providing the health-care provider or the self-administering subject a kit which will include all the required compositions in one package.

When in the form of a gas, a pharmaceutical kit includes a container or canister containing gNO in a carrier gas, which is configured for inhalation or topical application.

Thus, according to yet another aspect of the present invention, there is provided a pharmaceutical kit which includes inside a packaging material nitric oxide in any form as described herein and an antimicrobial agent being individually packaged. The kit can then be labeled according to its intended use and include instructions to carry out its intended use, such as for treating a medical condition associated with a pathogenic microorganism, or for treating a medical condition associated with a resistant pathogenic microorganism as described hereinabove, and/or for re-sensitizing a resistant pathogenic microorganism to an antimicrobial agent subsequent to the development of resistance towards the antimicrobial agent.

According to embodiments of this aspect, the kit comprises a therapeutically effective amount of the antimicrobial agent, which is otherwise ineffective against the specified microorganism for any reason when used without nitric oxide.

A Unit Dosage Form:

As described hereinabove, nitric oxide has unique features that enable it to be used as a potentiating and/or re-sensitizing agent which allow the use of the antimicrobial agent in dosages that are lower than the dosages commonly practiced without nitric oxide.

Hence, according to another aspect of embodiments of the invention, there is provided a pharmaceutical composition unit dosage form of an antimicrobial agent, which includes a therapeutically effective amount of an antimicrobial agent, which is intended for use in combination with nitric oxide.

Also provided is a pharmaceutical composition unit dosage form of nitric oxide, which includes a potentiating or re-sensitizing effective amount of nitric oxide in any form as described herein. When in the form of a gas, unit dosage form of NO can be provided in a container or canister configured for inhalation or topical application.

The term "unit dosage form", as used herein, describes physically discrete units, each unit containing a predetermined quantity of one or more active ingredient(s) calculated to produce the desired potentiating or re-sensitizing effect, in association with at least one antimicrobial agent, and other pharmaceutically acceptable carriers, diluents, excipients, and combination thereof.

The single unit dosage forms described herein can be formulated for any mode of administration as described herein.

According to embodiments of this aspect, pharmaceutical composition unit dosage form of an antimicrobial agent includes a therapeutically effective amount of the antimicrobial agent, which is otherwise insufficient for any reason against the specified microorganism when used without nitric oxide.

In some embodiments pertaining to all aspects of the present invention, nitric oxide isused in an amount that is lower than its MIC. In some embodiments, the amount of nitric oxide in a unit dosage form ranges from about 1 MIC units to about 1/10 MIC units, as described herein, of nitric oxide. In some embodiments, the unit dosage form comprises an amount of the antimicrobial agent that is 0.5-20 MIC units of the antimicrobial agent, or 1/2 MIC unit, 2/3 MIC unit, 3/4 MIC unit, 1 MIC unit, 2 MIC units, 5 MIC units, 10 MIC units, and more.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

Various embodiments and aspects of the present invention as delineated hereinabove and as claimed in the claims section below find experimental support in the following examples.

EXAMPLES

Example 1

Bronchiolitis Treatment by Nitric Oxide Inhalation

The study was conducted at the Soroka University Medical Center in southern Israel, and was approved by the Institutional and National Human Ethics Committee. A detailed study overview is attached as an online supplement. This study is registered with clinical trial number NCT01768884.

Figure 1:
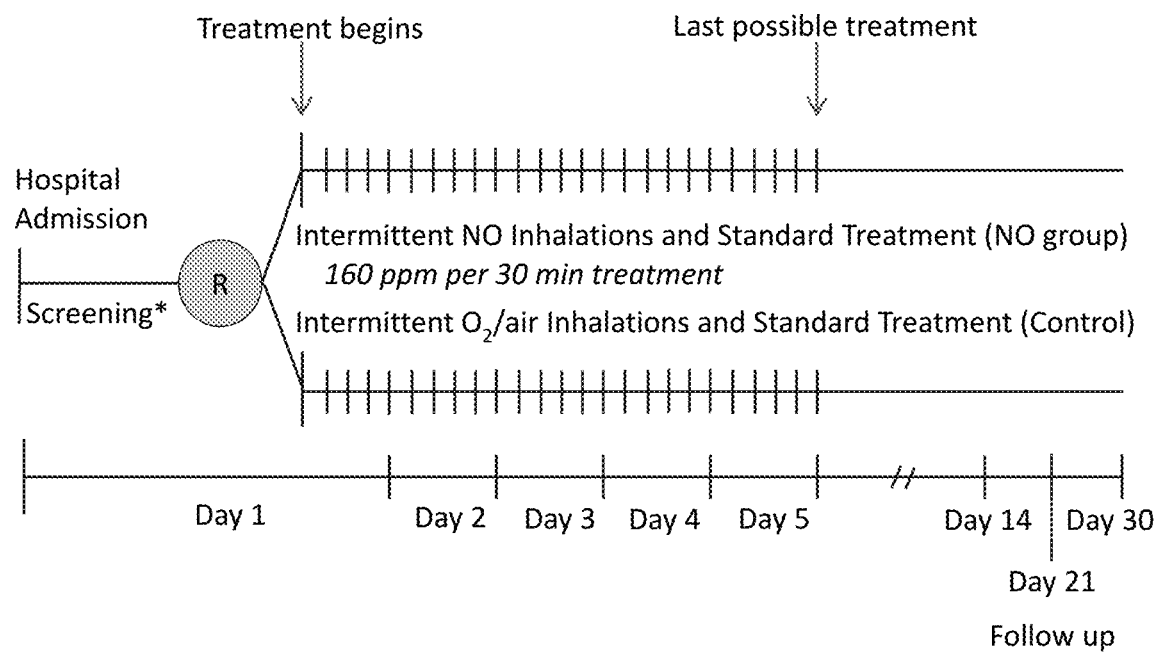
FIG. 1 shows the study design according to some embodiments.

The study was a randomized, prospective, single center, double blind study of 2-11 month old hospitalized infants with acute bronchiolitis (FIG. 1). Inclusion and exclusion criteria are summarized in Table 1.

Subjects were screened within 4 hours of admission and randomized (1:1) to receive intermittent inhalations of 160 ppm NO along with standard treatment (NO group) or intermittent inhalations of $O_2$/air mixture and standard treatment (control group), for a maximum of 25 inhalations.

Standard Supportive Treatment: This treatment included humidified oxygen, nasal suction when needed and hydration (oral, intra-venous or nasogastric tube fluids). The use of other concomitant medications was allowed, according to the ward's common practice.

Nitric Oxide Treatment: Subjects spontaneously inspired 160 ppm NO in fixed flow mode via a facemask. Nitric Oxide (Maxima, Israel) of 800 ppm (0.08%) NO balanced with 99.999% purity Nitrogen ($N_2$), was titrated into the $O_2$/air inspiratory delivery line. Inhaled NO, $NO_2$ and $O_2$ concentrations in the patient breathing circuit were continuously monitored using dedicated gas analyzers. (AeroNox, International medical, USA).

Outcome Measurements:

Primary Outcome: Safety measures, included % MetHb and NO2 production associated with NO treatment, bleeding episodes and any other adverse event (AE). Study threshold for $NO_2$ and MetHb was set at 5 ppm and 5%, respectively.

The primary outcome was safety and tolerability of intermittent inhalations of 160 ppm NO, given to infants 2 to 11 months with acute bronchiolitis. Safety measures included % MetHb associated with NO treatment (safety threshold was determined as >5% for MetHb and >5 ppm for $NO_2$), as well as any other AEs. Tolerability measures included the proportions of subjects who prematurely discontinued the study for any reason, and the proportion of subjects who prematurely discontinued the treatment due to severe SAEs.

Secondary Outcome: Efficacy parameters: LOS calculated in hours, starting from first inhalation until: 1) Oxygen saturation ($SpO_2$) ≥92% in room-air; 2) Clinical score≤5 (15, 16) and; 3) blinded physician decision of "ready for discharge".

The secondary outcome were efficacy measures, including LOS, time to achieve ≥92% $SaO_2$, and time to achieve a clinical score of ≤5. LOS in hours was defined as the time between first treatment until the time the infant was "ready for discharge", defined as 1. Room air saturation of ≥92%; 2. Clinical severity symptom score (Table E1) of ≤5; 3. A clinical decision made by a blinded pediatrician.

A severity symptom score, was used to determine the severity of each infant (Table E1). The score was comprised of four components: Respiratory rate, use of accessory muscles, wheezes and crackles on auscultation, and % room-air oxygen saturation ($SpO_2$). Each component is given 0 to 3 points, with a total possible score of 12. Infants with a score of <6 were determined as mild and were not included in the study, while infants with a score of >10 were determined as very severe and were also excluded.

Study Overview:

The research staff was divided into "blinded" and "unblinded" groups. The unblinded staff administered the inhalations to the infants and monitored % MetHb, % SpO2 (co-oximeter, RAD57/RAD 87, Masimo Corporation, USA), fractional inhaled $O_2$ ($FiO_2$), NO, $NO_2$ levels. The blinded group included the primary investigator and all other staff directly involved with patient care. Safety threshold for $NO_2$ and MetHb was set at 5 ppm and 5%, respectively. It should be emphasized that both treatments, $NO/O_2$ (NO treatment) as well as $O_2$/air mixture (control) were given via the same device, therefore, parents were also blinded to the treatment arm.

Each patient was given 5 inhalations a day of NO (treatment group) or oxygen (control group), along with the standard supportive treatment, for a maximum of 25 inhalations (based on phase I safety data). Each participant was examined and evaluated using the severity symptom score by a blinded pediatricians every morning (9 am and 3 pm). When the room-air $SpO_2$ reached 92%, and the score was ≤5, and the patient was assessed as "ready for discharge", the treatment was discontinued.

Initial evaluation included disease severity determination via clinical score (Table E1). (For more detailed description of the Clinical score, see on-line supplement). Subjects were examined and evaluated using the score twice daily. Follow-up was performed on days 14th, 21th and 30th from day of admission (see more detailed study oversight in on-line supplement).

Statistical Analysis:

The data were managed and analyzed by independent statisticians group using the SAS® version 9.1 (SAS Institute, Cary, North Carolina). The Paired T-Test was applied for testing the changes from baseline for quantitative variables; the two-sample T-test/Non-parametric Wilcoxon Rank Sum test or median tests were used for analyzing differences between the study groups in quantitative parameters; The Chi-square test was applied for testing the differences in frequency of categorical variables between the study groups; Kaplan-Meier survival function curves were applied for testing the difference between the study groups for the efficacy endpoints: The Cox model was applied for comparative analysis of Kaplan-Meier curves and hazard ratio estimation.

Post-hoc subgroup analyses of subjects with a LOS≤24 hours and >24 hours were also conducted for the key post-hoc secondary endpoints, for the following reasons: based on preclinical studies, the anti-microbial treatment effect of NO is expected to take approximately 2.5 hours of exposure (i.e., 24 hours treatment). A third of the subjects were discharged after <24 hours in hospital. A longer LOS is expected to correlate with a higher disease severity, and therefore any treatment effect should be more evident in the subgroup LOS>24 hours.

LOS was calculated in hours from the first inhalation treatment to "ready for discharge" defined as physician decision to discharge. The "ready for discharge" time was taken from the last clinical score where applicable, and from a subject's medical chart in special circumstances (i.e., for subjects who did not reach a clinical score of ≤5 during the study and for subjects who remained in the hospital for suspected bronchiolitis-related incidents).

Time to achieve room-air $SpO_2$ of ≥92% (improvement in oxygenation) leading to discharge was calculated from first treatment to the first time of room-air $SpO_2$ of ≥92% sustained until discharge. Time to clinical score of ≤5 was calculated from the first inhalation to the first time the subject reached a clinical score of ≤5.

All measured variables and derived parameters were tabulated by descriptive statistics. Categorical variables were presented in summary tables including sample size, absolute and relative frequencies, by study group and overall.

Continuous variables were summarized in tables including sample size, arithmetic mean, SD, standard error, median, minimum and maximum by study group.

The following statistical tests were used in the analysis of the data presented in this study: 1. The Paired T-Test was applied for testing the statistical significance of the changes from baseline for quantitative variables within each study group; 2. The two-sample T-test or Non-parametric Wilcoxon Rank Sum test or median tests were used as appropriate for analyzing differences between the study groups in quantitative parameters; 3. The Chi-square test was applied for testing the statistical significance of the differences in frequency of categorical variables between the study groups; 4. Survival analysis using a Kaplan-Meier survival function curve was applied for testing the statistical significance of the difference between the study groups in the following endpoints: LOS, from first inhalation to ready to discharge, time to achieve 92% saturation leading to discharge, and time to achieve clinical score≤5. The Cox model was applied for comparative analysis of Kaplan-Meier curves. The hazards ratio was estimated via the Cox's regression model.

All tests applied were two-tailed, and a P-value of 5% or less was considered statistically significant. The data was analyzed using the SAS® version 9.1 (SAS Institute, Cary North Carolina).

Post-hoc subgroup analyses of subjects with a LOS≤24 hours and >24 hours were also conducted for the key post-hoc secondary endpoints. These post-hoc analyses were conducted for the following reasons: based on preclinical studies, the anti-viral/anti-microbial treatment effect of NO is expected to take at least 2.5 hours of exposure (i.e., 24 hours treatment). Approximately ⅓ of subjects were discharged after <24 hours in hospital. Subjects with LOS<24 hours were considered as having "very mild disease" and their improvement was likely not related to any treatment. A longer LOS is expected to correlate with a higher disease severity, and therefore any treatment effect should be more evident in the subgroup LOS>24 hours.

The planned sample size was 40 subjects, 20 in each study group. Considering an expected dropout rate of approximately 10%, 44 subjects were planned for recruitment in order to have a sample size of 40 patients who completed the study.

Results:
Study Subjects:5

Figure 2:
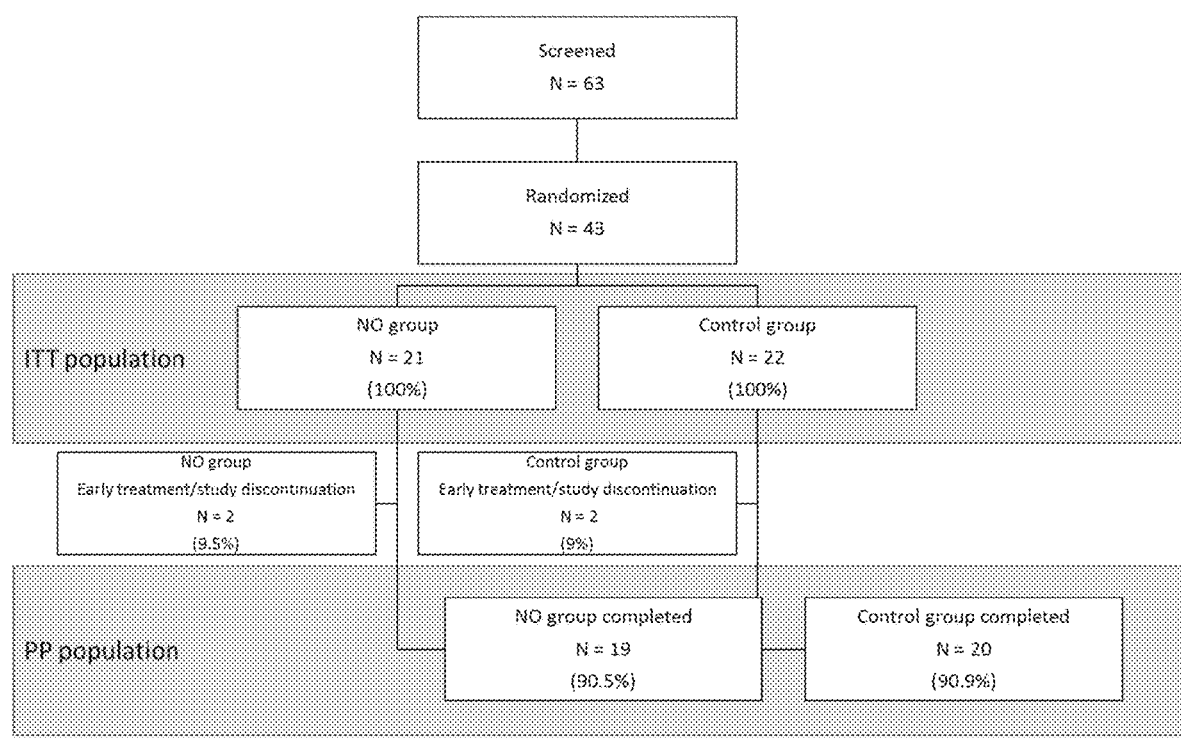
FIG. 2 shows the disposition of the infants treated according to some embodiments. N=number of infants; ITT=intent-to-treat subgroup; PP=per protocol subgroup.

A total of 63 infants were screened (FIG. 2): 20 parents declined consent, and thus 43 subjects were randomized: 21 in the NO group and 22 in the control group ($O_2$/air), and included in the "intention to treat" groups (ITT). The "per protocol" (PP) groups included 19 (90.5%) subjects in the NO group and 20 (90.9%) in the control group.

Demographics and Baseline Characteristics:5

Treatment groups were well-matched for demographic and baseline characteristics (gender, ethnicity, age, weight at screening, gestational age at birth, and MetHb values at screening) (Table 2). The mean (±Standard Deviation [SD]) age was 4.8±2.3 and 5.6±2.8 months in the NO and the control groups, respectively. The respective mean baseline MetHb values were 0.7±0.4% and 0.7±0.30%; mean clinical score was 7.9±1.1 and 8.1±1.3. All studied infants in both groups had a moderate severity of bronchiolitis by score.

In both treatment groups, the majority of subjects were positive for RSV (71.4% and 63.6% in the NO and control groups, respectively). Other detected viruses included corona virus (4 patients per group), adenovirus (2 patients in the control group), metapneumovirus (2 patients in the NO group, 1 in the control), and influenza A (6 patients in the control). Demographics and baseline characteristics were also similar for subgroups with a LOS>24 hours and <24 hours (Table E2).

A total of 156 NO inhalations were administered, and 198 02/air mixture given to the control group. The mean number of inhalations was lower in the NO group (7.4±3.2, maximum 16) compared to the control (9.0±6.5, maximum 25).

Concomitant Medications:

All subjects in both treatment groups had >1 concomitant medication, and the treatment groups were well balanced with regard to overall frequency and type of concomitant medications. The most frequent concomitant medication types were: beta-agonists, paracetamol, atropine-like, hypertonic saline, systemic steroid, and antibiotics (Table E3).

Safety Evaluation:

AEs were reported in 23 (53.5%) subjects, 10 (47.6%) subjects in the NO with 22 AEs, and 13 (59.1%) in the control group with 22 AEs. (Table 3, E4).

Solicited AEs potentially related to NO treatment, were MetHb >5%, NO2 elevation >5 ppm, and bleeding (17). AEs considered possibly or probably related to inhalation treatment were reported in 5 (23.8%) and 2 (9.1%) subjects in the NO and the control groups, respectively. Serious AEs (SAES) were reported in 4 (19.0%) and in 4 (18.2%) subjects in the NO and the control groups respectively. There was no treatment-related SAE in the NO group, compared to one subject in the control group. There were no bleeding episodes or deaths during the study.

Figure 3:
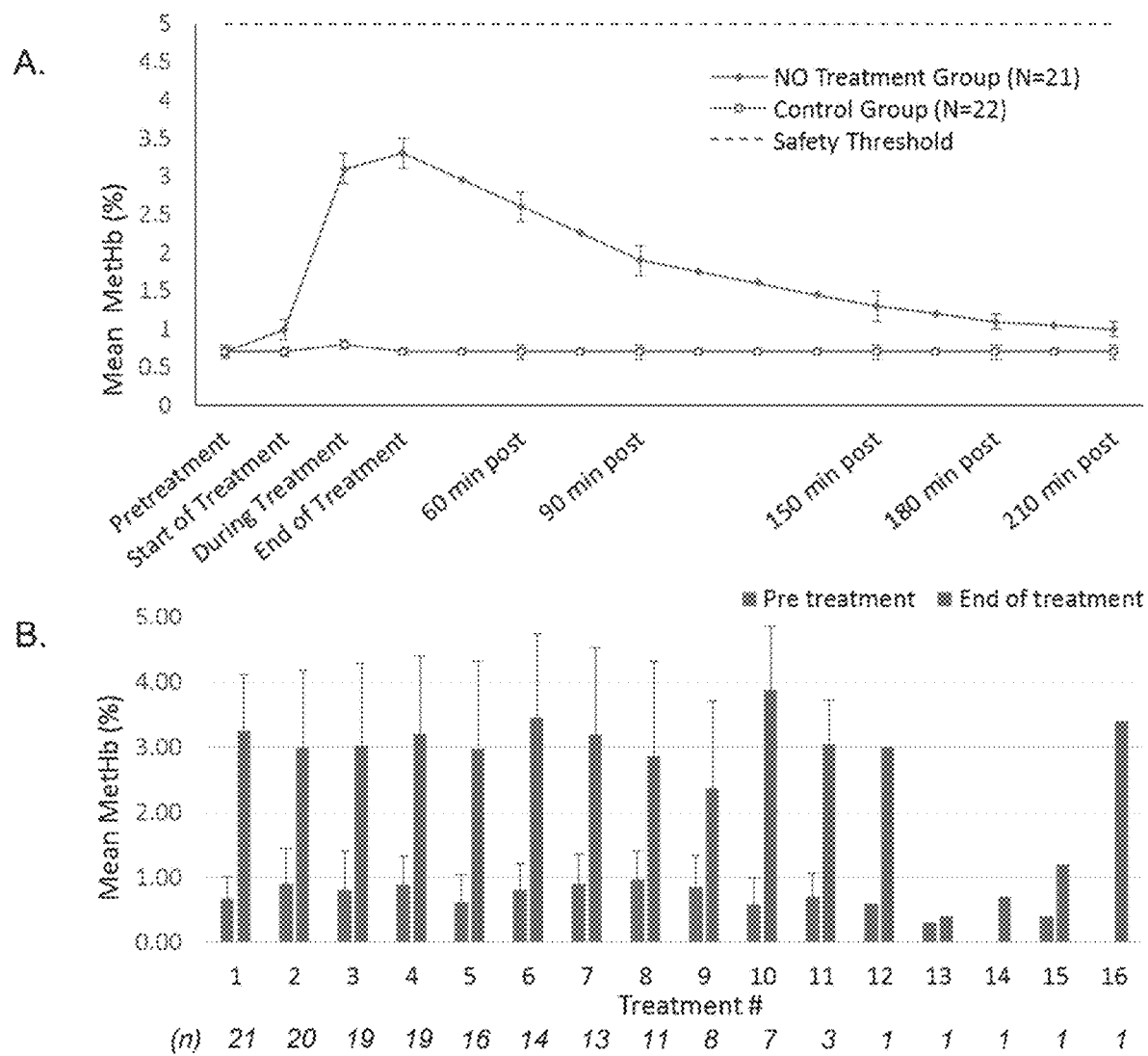
FIG. 3 shows methemoglobin levels in infants treated according to some embodiments. Panel A: Mean (±SE)

Primary Safety Endpoints—MetHb Percentage Associated with Inhaled NO:

In the NO group, 6 (28.5%) subjects had MetHb measurement >5% during the study treatment period, and in 3 of these subjects values >5% were observed more than once >5% (maximum value was 5.6% in two subjects). MetHb values increased in each NO inhalation, with peak values at end of inhalation (mean 3.3±0.9%), then gradually declined, approaching pre-treatment levels (FIG. 3a). Comparing pre- and end of inhalation MetHb levels, there was no cumulative effect of MetHb levels over the treatment period (FIG. 3b).

One subject in the NO group experienced once an increased NO level>5 ppm (5.5 ppm). The mean peak NO2 at the end of the first inhalation in 21 infants was 1.55 (SD=0.55) ppm, which is well below the 5 ppm safety threshold (FIG. 4).

Tolerability: Four subjects, 2 (9.5%) in the NO and 2 (9.1%) in the control group discontinued the study/study treatment. Two subjects (one from each group) discontinued treatment because of parental withdrawal of consent or parental non-compliance; the third (NO group) discontinued the study due to a second AE of MetHb >5%, and the fourth (control) discontinued treatment due to an SAE of respiratory failure and was transferred to the pediatric intensive care unit.

Secondary Outcomes—Efficacy Evaluation:

Length of stay (LOS): There were 43 subjects in the ITT analysis. The mean±SD LOS was 43.3±32.95 hours for the NO group compared to 50.0±46.2 hours in the control group (P=0.86). When LOS was analyzed including the 16 infants with mild bronchiolitis that were discharged within <24 hours, the median LOS was 40 hours compared to 24.5 hours, in the NO and control groups, respectively (P=0.65). When post-hoc analyses (ITT) were performed based on LOS>24 hours and LOS≤24 hours, the median LOS was significantly shorter in the NO group (41.92 hours) compared to the control group (62.50 hours) (P=0.014) (FIG. 5). Kaplan Meier analyses for ITT and PP for LOS are described in FIG. 6.

Time to First 92% $O_2$ Saturation Sustained to Discharge: Time to first 92% $O_2$ saturation sustained to discharge, for ITT (N=42) was 35.50±33.73 hours in the NO group compared to 45.75±44.43 hours in the control group (P=0.517). Kaplan Meier Analyses of LOS>24 hours for PP, showed a statistically significant difference in favor of the NO group (HR=0.358, 95% CI=0.139, 0.921; P=0.028) (FIG. 7).

Time to Clinical Score of <5: Analysis for ITT (N=43), revealed a shorter but not statistically significant mean time to reach clinical score of ≤5 in the NO group: 32.83±30.61 hours compared to 43.10±43.91 hours in the control group (P=0.621). However, based on Kaplan-Meier analysis of subjects with LOS>24 hours, a statistically significant difference was seen in favor of the NO group (HR=0.391, 95% CI: 0.161, 0.949; log rank P-value=0.033) (FIGS. 8A&B). Kaplan-Meier analysis for PP also showed a statistically significant difference in favor of the NO group for subjects with LOS>24 hours, (HR=0.273, 95% CI: 0.093, 0.799; log rank P-value=0.013) (FIGS. 8C&D).

Discussion

The primary outcome of this study of 43 infants, 2-11 months-old, with bronchiolitis was safety and tolerability, with encouraging results. Secondary efficacy outcomes were evaluated although the study was not powered for efficacy. We found no statistically significant safety and tolerability differences between NO and control treatment groups (ITT, PP). Post-hoc analysis, in a subgroup of subjects with LOS>24 hours (>2.5 hr NO exposure) demonstrated a statistically significant clinical benefits of NO versus standard treatment with respect to a shorter LOS, shorter time to room-air SpO2≥92%, and shorter time to clinical score≤5.

NO plays a critical role in various biological functions, including the vasodilatation of smooth muscles, neurotransmission, anti-inflammatory effects, regulation of wound healing and immune responses to infection such as microbicidal action directed toward various organisms. NO also acts as an antiviral agent, including inhibition of Herpes Simplex virus type 1. Several mechanisms and pathways are considered in the ability of NO to eliminate viral infection: inhibition of viral proteinases and ribonucleotide reductase, RNA entry into host cells, transcription factors needed for viral infection and viral protein accumulation, and viral replication during the first steps of viral replication cycle, viral release from infected cells, and modulation of the host response to infection.

NO is approved for the treatment of term and near-term neonates in a dose of 20 ppm, maintained for up to 14 days continuous delivery. Doses of up to 80 ppm were used during clinical trials (FDA Approval of NDA 20-86 INOmax nitric oxide gas 1999).

Safety issues of inhaled NO treatment include MetHb accumulation, $NO_2$ formation, and bleeding. Inhaled nitric oxide can combine with hemoglobin to form nitrosylhemoglobin, which is rapidly oxidized to methemoglobin (metHb). Cyanosis does not appear until metHb levels are 15-20%, and clinical symptoms of hypoxia do not generally become significant at levels below about 30% of hemoglobin. In the neonatal study Methb levels of 5 to 10% were managed by reducing the concentration of NO by half until the level fell below 5%. Furthermore, the corresponding rise in MetHg percentage during the study confirmed that there was sufficient NO in the respiratory tract to be absorbed into the blood stream and metabolized.

In the neonatal study, inhaled NO was discontinued when $NO_2$ exceeded 7 ppm. At higher doses, the major toxicologic effect of $NO_2$ is pulmonary edema (Centers for Disease Control, 1988). Nevertheless, in previous studies, at NO doses less than 80 ppm, there were neither significant elevations in measured $NO_2$ levels nor clinical evidence of $NO_2$ toxicity. Similarly, in the present study, 30 minutes of inhaled 160 ppm NO five time a day, was neither associated with significant elevations in $NO_2$ nor clinical evidence of toxicity.

The intermittent dosing strategy was selected to minimize the potential for adverse effects while maximizing the antiviral and anti-bacterial effectiveness of NO as well as the added treatment benefits of anti-inflammatory and vasodilator properties, further promoting airway clearance. The present study findings that there was no accumulation of MetHb, no events of significant $NO_2$ elevations, and no bleeding episodes support the rational of intermittent 160 ppm inhalation therapy in humans. The dose and time requirements of NO, as an antibacterial agent, were determined and shown effective in both planktonic suspensions and biofilms. Treating influenza virions or infected cell with intermittent (30 minutes every 4 hours) 160 ppm exogenous gaseous NO reduced not just viral replication, but also its infectivity in a Madin-Darby Canine Kidney (MDCK) cell model of infection. Inhalation of 160 ppm NO for 30 minutes, 5 times daily, for 5 consecutive days, is safe and well tolerated in healthy individuals.

Secondary outcomes related to efficacy were evaluated, although the study was not powered for efficacy. Based on previous in vitro and animal studies, indicating that at least 2.5 hours of NO exposure was needed before an antimicrobial effect was seen, a post-hoc analysis was conducted, comparing NO treatment to the control in a subgroup of infants who remained hospitalized for >24 hours (>5 treatments of 30 min). In this subgroup the differences in efficacy were statistically significant in favor of the NO group: shorter LOS (ITT), shorter time to score≤5 (ITT) and time to SpO2≥92%

Mean hospital stay in infants with bronchiolitis is short, therefore it is difficult to show significant reductions in outcomes such as viral load. We chose as the main efficacy outcome LOS in hours. This outcome was used in a few recent studies (11, 23, 24). LOS depends on two important outcome measures, namely the rate of clinical improvement and the need for oxygen treatment. Severity scoring systems have a high power to detect clinical differences between groups, especially when placebo is used (11) The modified Tal score (15) has been shown to be internally consistent and with good interrater reliability(16). We have recently conducted an internal validation study of the modified Tal score, with highly significant intra class correlation coefficient among 17 pediatricians with different levels of experience, scoring 50 infants twice a day during their hospitalization (unpublished data).

No specific treatment has yet been approved for RSV-bronchiolitis. Recently, several selective RSV antiviral compounds have been identified in preclinical studies (25). Currently, only supportive treatments such as oxygen, fluids and nasopharyngeal suction are recommended (12). Our preliminary results, therefore, suggest that NO inhalations may provide a reasonable tool for the improvement of RSV outcome. The therapeutic potential of NO inhalation hinted at in the current study needs to be further studied with a larger double blind placebo-controlled trial powered to look at both safety/tolerability and multiple efficacy endpoints.

In conclusion, in this study of hospitalized infants with acute bronchiolitis, the safety and tolerability of intermittent inhalation treatment of 160 ppm NO were comparable to those in the standard-supportive treatment. Secondary exploratory analyses, of a subgroup of subjects with LOS>24 hours, showed a statistically significant treatment benefit in terms of decreased LOS and time to achieve 92% saturation, and accelerated clinical improvement of NO versus standard supportive treatment. Although our study sample was small, our efficacy results are encouraging and support the anti-viral potential of intermittent 160 ppm NO inhalations in LRTI. Larger scale trials are needed to corroborate the beneficial effect of inhaled NO in viral bronchiolitis.

Example 2

Potentiation of Antimicrobial Agents: Background Art

To determine the effect of 200 ppm gNO on microorganisms, a series of experiments tested the response of the bacteria at clinically infective concentrations of ($10^5$) $10E^5$ CFU/ml that were isolated from patients suffering from a medical condition associated with these bacteria, to exposure to 200 ppm gNO [Chris C. Miller, PhD thesis, University of British Columbia, Canada, 2004]. Each study was performed at least once with a minimum of two samples for each time point. In all of the experiments, the control (exposure air) had 100% or more survival rate during the study interval when compared to the original inoculums. The reduction in CFU/ml for each gNO-exposed organism was between a 4-6 $Log_{io}$ units, indicating 15 a significant bactericidal effect of 200 ppm gNO.

The survival curve for each bacteria in terms of CFU/ml was plotted as a function of time. Each graph plotted the bacteria's survival curve for 200 ppm gNO and the control (exposure air).

Briefly, $5 \times 10^5$ cells of an exemplary bacterium, *Serratia marcescens*, were suspended iN 2 ml saline solution in a test tube and exposed to a flow of 1 liter/minute of 200 ppm gNO in nitrogen. Survival rate was measured by determining the numbers of bacterial cells remaining in the culture every hour by viable counts and serial dilutions, and the results are summarized in FIG. 9. FIG. 9 presents plot, showing the antimicrobial activity of nitric oxide against *Serraia marcescens*, as described in the presentation of background art hereinabove, and demonstrating the latent period of antimicrobial activity, attributed to the time required to deplete the chemical defense mechanism of the microorganism, wherein curve 11 is the number of cells as a function of time of exposure to 200 ppm NO, curve 12 is the control text (exposure of bacteria to air), point 13 signifies the lethal dose that killed 100% of the bacteria (LD100); point 14 signifies the latency period defined as stable or less than 1 log decrease in bacterial population (LP1), point 15 marks the $-2.5$ $Log_{10}$ level and point 16 marks the end of the latency period; point 18 marks the point of no return where even if the exposure to NO is ceased, the bacteria will continue to die, a phenomenon which coincides with point 20 which marks the level of 50% decrease in colony Forming Units ($CFU_{50}$), whereas point 22 signifies $CFU_{100}$ level and point 24 signifies 1 Log10 unit.

Similar data was collected and plotted for *S. aureus* (ATCC 25923), *P. aeruginosa* (ATCC 27853), MRSA and clinical strains of *S. aureus, S. marcescens, Klebsiella pneumonia* species, *S. maltophilia, Enterobacter aerogenes* species, *Acinetobacter baumannii*, Group *B Streptococci* and *E. coli*. Other microorganisms tested were *Candida albicans, Mycobacterium smegmatis* and multi-drug resistant strain of *Pseudomonas aeruginosa*, and the results are summarized in Table 4 below.

Table 4 presents latent periods measured in vitro for a variety of bacterial species/strains, as well as the time period at which a 2.5-fold reduction in microbial load ($-2.5$ $Log_{10}$) and the eradication of the microbes ($LD_{100}$) has been observed.

Example 3

High Throughput Synergy Screening

To screen for antimicrobial agents that exhibit a high degree of potentiation by exposure of target cells to nitric oxide, a high throughput synergy screen (HTSS) assay of antimicrobial agents libraries, using the identified disease causing pathogenic microorganism to be treated is carried out. The pathogenic microorganism are grown on agar plates in the presence or absence of a sub-inhibitory concentration (sub-MIC levels) of nitric oxide or NO-releasing compounds.

While some antimicrobial agents in the library may exhibit antimicrobial activity without the presence of NO, assays are carried out while comparing the zones of inhibition in the presence and absence of nitric oxide. This comparison enables identifying antimicrobial agents that become more active in the presence of nitric oxide. The growth kinetics of the tested pathogenic microorganism is monitored in the presence of a range of nitric oxide concentrations and identifies the minimal inhibitory concentration of the antimicrobial agents.

"Chequerboard Assay", a standard method used to rigorously confirm synergistic activities of antibiotics (Ramon-Garcia S et. al. AAAC, 2011), is employed. This assay is carried out in cultures grown in 96 well plates. A two dimensional array of serial concentrations of the two test compounds (nitric oxide and the identified antimicrobial agent) is then introduced to logarithmically growing cultures. Calculations based on relative MIC concentrations in wells representing various ratios of the two compounds are used to demonstrate that paired combinations of agents exert inhibitory effects that are more than the sum of their effects alone (synergy).

Example 4

Treatment Regimen

Respiratory infection in a human subject, associated with respiratory pathogens, such as bacteria, is treatable using the method presented herein, namely using a combination of suitable antibiotics and nitric oxide (NO).

Two groups of patients are compared: patients with respiratory infections such as pneumonia, which are treated with, e.g., intermittent inhalation of 160 ppm NO, 3 times a day, for about 10 days, in combination with standard antibiotic, compared with a group of patients diagnosed with the same type of pneumonia but are treated with standard antibiotic treatment only.

Patients treated with a combination of NO and standard antibiotic treatment should exhibit a significant improvement in clinical parameters, such as body temperature (more rapidnormalization), oxygen consumption, respiratory rate and lung functions, compared to the patients treated with standard antibiotic treatment only.

Patients treated with a combination of NO and standard antibiotic treatment should exhibit a significant improvement in overall clinical score, based on tested parameters, compared to the patients treated with standard antibiotic treatment only.

In addition the respiratory bacterial flora should be changes following the indicated treatment with reduction in the population of pathogenic bacteria.

Patients treated with a combination of NO and standard antibiotic treatment should experience reduction of length of hospitalization in terms of days, fewer events of deterioration of the patients necessitating intensive care admission due to respiratory failure, and/or a reduction in the use of antibiotics in general.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE 1

| Inclusion and Exclusion Criteria |
|---|
| Inclusion Criteria |
| 1. Subjects (Male or female) 2-11 months old<br>2. Diagnosed as bronchiolitis<br>3. Clinical score >6 and ≤10<br>4. Parents/legal guardian signed informed consent |
| Exclusion Criteria |
| 1. Subjects diagnosed with concomitant diseases such as pneumonia, urinary tract infection or otitis media<br>2. Prematurity <36 weeks gestational age.<br>3. Received RSV immunoglobulin prophylaxis<br>4. Subjects diagnosed with, methemoglobinemia, chronic lung disease, immunodeficiency, heart disease<br>5. Use of an investigational drug within 30 days before enrollment and not expected to participate in a new study within 30 days<br>6. History of frequent epistaxis (>1 episode/month)<br>7. Significant hemoptysis within 30 days (≥5 mL of blood in one coughing episode or >30 mL of blood in a 24 hour period)<br>8. Methemoglobin >3% at screening<br>9. Subjects cannot fulfill the study design<br>10. Presence of a condition or abnormality that in the opinion of the investigator would compromise the safety of the subject or the quality of the data.<br>11. Underlying diseases such as genetic disorders (Cystic fibrosis, Down Syndrome) or chronic lung diseases (Bronchopulmonary dysplasia, primary ciliary diskynesia, bronchiolitis obliterans, hypotonia, congenital heart disease) |

TABLE 2

Demography and Baseline Characteristics (ITT, N = 43)

| Demographic Variable | NO Group (N = 21) | Control Group (N = 22) | P-value Chi-square Test* | P-value T-test† | P-value Wilcoxin‡ |
|---|---|---|---|---|---|
| Gender (n (%)) | | | 0.9065 | — | — |
| Male | 13 (61.9%) | 14 (63.6%) | — | — | — |
| Female | 8 (38.1%) | 8 (36.4%) | — | — | — |
| Ethnicity (n (%)) | | | 0.6502 | — | — |
| Jewish | 5 (23.8%) | 4 (18.2%) | — | — | — |
| Bedouin | 16 (76.2%) | 18 (81.8%) | — | — | — |
| Age (months) | | | | | |
| N | 21 | 22 | — | — | — |
| Mean (SD) | 4.8 (2.3) | 5.6 (2.8) | — | 0.3486 | 0.4627 |
| Median | 4.1 | 5.5 | — | — | — |
| Min/max | 2.0/8.7 | 2.0/11.9 | — | — | — |

TABLE 2-continued

Demography and Baseline Characteristics (ITT, N = 43)

| Demographic Variable | NO Group (N = 21) | Control Group (N = 22) | P-value Chi-square Test* | P-value T-test† | P-value Wilcoxin‡ |
|---|---|---|---|---|---|
| Weight at screening (g) | | | | | |
| N | 21 | 22 | — | — | — |
| Mean (SD) | 6.6 (1.6) | 6.8 (1.8) | — | 0.8114 | 0.9807 |
| Median | 6.5 | 6.5 | — | — | — |
| Min/max | 3.6/10.0 | 4.4/11.0 | — | — | — |
| Gestational age at birth (weeks) | | | | | |
| N | 21 | 22 | — | — | — |
| Mean (SD) | 38.9 (1.6) | 39.3 (1.1) | — | 0.2776 | 0.2363 |
| Median | 39.0 | 40.0 | — | — | — |
| Min/max | 36.0/42.0 | 36.0/40.0 | — | — | — |
| MetHb at screening (%) | | | | | |
| N | 21 | 21 | — | — | — |
| Mean (SD) | 0.69 (0.43) | 0.73 (0.30) | — | 0.7106 | — |
| Median | 0.80 | 0.70 | — | — | — |
| Min/max | 0.10/1.40 | 0.20/1.20 | — | — | — |
| Clinical score at screening | | | | | |
| N | 21 | 22 | — | — | — |
| Mean (SD) | 7.86 (1.11) | 8.09 (1.27) | — | 0.5244 | 0.4600 |
| Median | 7.00 | 8.00 | — | — | — |
| Min/Max | 7.00/10.00 | 6.00/8.00 | — | — | — |

*Chi-square test for testing significance of difference in proportions between the study groups.

†T-test (unpaired) for difference in means between the study groups.

‡Non-parametric Wilcoxon-Mann-Whitney Rank sum test for difference in means between the study groups.

Definition of abbreviations: ITT = Intent-to-Treat; Max = Maximum; Min = Minimum; MetHb = Methemoglobin; ND = Not determined; SD = Standard deviation

TABLE 3

Overall Summary of Adverse Events (AE)

| | NO Group (N = 21) n (%) E | Control Group (N = 22) n (%) E | All (N = 43) n (%) E | P-value for frequency of AEs* |
|---|---|---|---|---|
| Any AE | 10 (47.6%) 22 | 13 (59.1%) 22 | 23 (53.5%) 44 | 0.4509 |
| Any severe AE | 1 (4.8%) 1 | 2 (9.1%) 2 | 3 (7.0%) 3 | — |
| Any serious AE | 4 (19.0%) 4 | 4 (18.2%) 5 | 8 (18.6%) 11 | — |
| Any treatment-related AE | 5 (23.8%) 6 | 2 (9.1%) 2 | 7 (16.3%) 8 | 0.1913 |
| Any serious treatment-related AE | 0 (0.0%) 0 | 1 (4.5%) 1 | 1 (2.3%) 1 | — |
| Treatment withdrawal due to AE | 1 (4.8%) 1 | 1 (4.5%) 1 | 2 (4.7%) 2 | 0.9731 |
| Death | 0 (0.0%) 0 | 0 (0.0%) 0 | 0 (0.0%) 0 | — |

*Chi-square test.

Treatment-related was defined as any AE considered by the Investigator to be possibly or probably related to study treatment.

AE = Adverse event; E = Event.

"—" indicates not determined.

TABLE E1

Determination of Clinical Score

| Score | Respiratory Rate (Breaths/Minute) | | Wheezing | $SpO_2$ (Room Air) | Accessory Muscle Use |
| --- | --- | --- | --- | --- | --- |
| | Subject <6 Months | Subject ≥6 Months | | | |
| 0 | 40 | 30 | None* | ≥95% | None |
| 1 | 41-55 | 31-45 | End expiration with stethoscope | 92-94% | + |
| 2 | 56-70 | 46-60 | Inspiration and expiration with stethoscope | 90-91% | ++ |
| 3 | >70 | >60 | Audible without stethoscope | ≤89% | +++ |

*If wheezes not audible due to a minimal air entry, consider score = 3.

Notes:
Clinical score was calculated as the sum of scores given according to each parameter (respiratory rate, wheezing, $SpO_2$ and accessory muscle use). Mild: ≤5; Moderate: 6-10; Severe: 11-12.
Definitions of abbreviations: $SpO_2$ = Oxygen saturation.
References (E1, E2)

TABLE E2

Demographic and Baseline Characteristics of Subjects with a LOS ≤24 Hours and >24 Hours (ITT, N = 43)

| Demographic Variable | LOS ≤24 Hours (N = 16) | | LOS >24 Hours (N = 27) | |
| --- | --- | --- | --- | --- |
| | NO Group (N = 6) | Control Group (N = 10) | NO Group (N = 15) | Control Group (N = 12) |
| Gender (n (%)) | | | | |
| Male | 3 (50.0%) | 8 (80.0%) | 10 (66.7%) | 6 (50.0%) |
| Female | 3 (50.0%) | 2 (20.0%) | 5 (33.3%) | 6 (50.0%) |
| Age (months) | | | | |
| N | 6 | 10 | 15 | 12 |
| Mean (SD) | 5.49 (2.31) | 5.42 (2.66) | 4.57 (2.27) | 5.70 (3.06) |
| Median | 5.45 | 5.14 | 4.11 | 5.86 |
| Min/max | 2.86/8.05 | 1.97/9.95 | 2.04/8.67 | 2.07/11.93 |
| Body temperature at screening(° C.) | | | | |
| N | 6 | 10 | 15 | 12 |
| Mean (SD) | 37.20 (0.52) | 37.64 (0.88) | 37.57 (0.84) | 37.36 (0.91) |
| Median | 37.20 | 37.50 | 37.50 | 37.20 |
| Min/max | 36.30/37.80 | 36.50/39.50 | 36.40/38.80 | 36.40/39.40 |
| Clinical score at screening | | | | |
| N | 6 | 10 | 15 | 12 |
| Mean (SD) | 7.67 (1.21) | 8.30 (1.25) | 7.93 (1.10) | 7.92 (1.31) |
| Median | 7.00 | 8.00 | 7.00 | 8.00 |
| Min/max | 7.00/10.0 | 6.00/10.0 | 7.00/10.0 | 6.00/10.0 |

Definitions of abbreviations: ITT = Intent-to-Treat; Max = Maximum; Min = Minimum; MetHb = Methemoglobin; ND = Not determined; SD = Standard deviation

TABLE E3

Summary of Concomitant Medications (ITT, N = 43)

| Medication Type | NO Group (N = 21) n (%) | Control Group (N = 22) n (%) |
| --- | --- | --- |
| Any concomitant medication | 21 (100.0%) | 22 (100.0%) |
| Adrenaline | 4 (19.0%) | 1 (4.5%) |
| Antibiotics | 6 (28.6%) | 11 (50.0%) |
| Atropine-like | 8 (38.1%) | 3 (13.6%) |
| Beta-agonist | 12 (57.1%) | 16 (72.7%) |
| Dermacombin | 1 (4.8%) | 0 (0.0%) |
| Hypertonic Saline | 4 (19.0%) | 7 (31.8%) |
| Inhaled corticosteroids | 1 (4.8%) | 4 (18.2%) |
| Otrivin | 1 (4.8%) | 0 (0.0%) |
| Otidin | 1 (4.8%) | 1 (4.5%) |
| Paracetamol | 10 (47.6%) | 12 (54.5%) |

TABLE E3-continued

Summary of Concomitant Medications (ITT, N = 43)

| Medication Type | NO Group (N = 21) n (%) | Control Group (N = 22) n (%) |
|---|---|---|
| Systemic steroids | 7 (33.3%) | 9 (40.9%) |
| Tamiflu | 0 (0.0%) | 4 (18.2%) |
| Vitamin D | 16 (76.2%) | 20 (90.9%) |

TABLE E4

Summary of Treatment-Related AEs

| MedDRA SOC Preferred Term | NO Group (N = 21) n (%) Events | Control group (N = 22) n (%) Events |
|---|---|---|
| Any treatment-related AE | 5 (23.8%) 6 | 2 (9.1%) 2 |
| Blood and Lymphatic System Disorders | 4 (19.0%) 5 | 0 (0.0%) 0 |
| Methaemoglobinaemia* | 4 (19.0%) 5 | 0 (0.0%) 0 |
| Investigations† | 1 (4.8%) 1 | 2 (9.1%) 2 |
| NO₂ increase† | 1 (4.8%) 1 | 0 (0.0%) 0 |
| Oxyemoglobin decreased‡ | 1 (4.8%) 1 | 2 (9.0%) 2 |

*Methemoglobin >5%.
†$NO_2$ concentration >5 ppm.
‡Oxyhemoglobin <89%.
Definitions of abbreviations: AE = Adverse event; E; MedDRA = Medical Dictionary for Regulatory Activities; ppm = Particles per million; SOC = System Organ Class.

TABLE 4

| Bacteria | Gram staining | Latent Period (hours) | -2.5 $Log_{10}$ (hours) | $LD_{100}$ (hours) |
|---|---|---|---|---|
| S. aureus (ATCC) | Positive | 3 | 3.3 | 4 |
| P. aeruginosa (ATCC) | Negative | 1 | 2.1 | 3 |
| MRSA | Positive | 3 | 4.2 | 5 |
| Serracia sp. | Negative | 4 | 4.9 | 6 |
| S. aureus (Clinical) | Positive | 3 | 3.7 | 4 |
| Klebsiella sp. #1 | Negative | 3 | 3.5 | 6 |
| Klebsiella sp. #2 | Negative | 2 | 4.1 | 5 |
| Klebsiella sp. #3 | Negative | 3 | 5.1 | 6 |
| S. maltophilia | Negative | 2 | 2.8 | 4 |
| Enterobacter sp. | Negative | 4 | 5.3 | 6 |
| Acinetobacter sp. | Negative | 4 | 5 | 6 |
| E. coli | Negative | 3 | 4.2 | 5 |
| Group B Streptococci | Positive | 1 | 1.5 | 2 |
| Average | N/A | 2.77 | 3.82 | 4.77 |
| SD | N/A | 1.01 | 1.17 | 1.30 |
| Mycobacterium smegmatis | Positive | 7 | 9.2 | 10 |

What is claimed is:

1. A method of treating a subject having a medical condition associated with a pathogenic microorganism, the method comprising:
   (i) administering to said subject a potentiating effective amount of nitric oxide by inhalation; and
   (ii) administering to said subject a therapeutically effective amount of an antimicrobial agent,
   wherein said antimicrobial agent is other than said nitric oxide, and
   wherein said antimicrobial agent is inactive when used alone against said pathogenic microorganism.

2. The method of claim 1, wherein said potentiating effective amount is lower than a therapeutically effective amount of said nitric oxide with respect to said pathogenic microorganism.

3. The method of claim 2, wherein said potentiating effective amount is lower than 1 MIC unit of nitric oxide with respect to said pathogenic microorganism.

4. The method of claim 1, wherein said pathogenic microorganism exhibits a resistance to said antimicrobial agent prior to said administering said potentiating effective amount of nitric oxide.

5. The method of claim 1, wherein (i) is affected prior to (ii).

6. The method of claim 1, wherein (i) is affected concomitantly with (ii).

7. The method of claim 1, wherein (ii) is affected prior to (i).

8. The method of claim 1, wherein the pathogenic microorganism is selected from one or more of gram-negative bacteria, gram-positive bacteria, eubacteria, archaebacteria, eukaryotic organisms, yeast, fungi, algae, protozoa, and other parasites.

9. The method of claim 8, wherein the pathogenic microorganism is selected from one or more of Plasmodium falciparum and related malaria-causing protozoan parasites, Acanthamoeb, Aeromonas hydrophila, Anisakis and related worms, Serracia sp., Enterobacter sp., Acinetobacter sp., Acinetobacter baumanii, Ascaris lumbricoides, Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica, Escherichia coli, Eustrongylides, Giardia lamblia, Klebsiella pneumoniae, Listeria monocytogenes, Nanophyetus, Mycobacterium smegmatis, Mycobacterium tuberculosis, Mycobacterium avium intracellularae, Plesiomonas shigelloides, Proteus mirabilis, Pseudomonas aeruginosa, Salmonella, Serratia odorifera, Shigella, Staphylococcus aureus, Stenotrophomonas maltophilia, Streptococcus, Trichuris trichiura, Vibrio cholerae, Vibrio parahaemolyticus, Vibrio vulnificus, Yersinia enterocolitica, Yersinia pseudotuberculosis and Yersinia kristensenii.

10. The method of claim 1, wherein the pathogenic microorganism is a bacteria, and the medical condition is a bacterial infection selected from one or more of actinomycosis, anthrax, aspergillosis, bacteremia, bacterial skin diseases, bartonella infections, botulism, brucellosis, burkholderia infections, campylobacter infections, candidiasis, cat-scratch disease, chlamydia infections, cholera, clostridium infections, coccidioidomycosis, cryptococcosis, dermatomycoses, diphtheria, ehrlichiosis, epidemic louse borne typhus, Escherichia coli infections, fusobacterium infections, gangrene, general infections, general mycoses, gonorrhea, gram-negative bacterial infections, gram-positive bacterial infections, histoplasmosis, impetigo, klebsiella infections, legionellosis, leprosy, leptospirosis, listeria infections, lyme disease, malaria, maduromycosis, melioidosis, mycobacterium infections, mycoplasma infections, necrotizing fasciitis, nocardia infections, onychomycosis, omithosis, pneumococcal infections, pneumonia, pseudomonas infections, Q fever, rat-bite fever, relapsing fever, rheumatic fever, rickettsia infections, Rocky-mountain spotted fever, salmonella infections, scarlet fever, scrub typhus, sepsis, sexually transmitted bacterial diseases, staphylococcal infections, streptococcal infections, surgical site infection, tetanus, tickborne diseases, tuberculosis, tularemia, typhoid fever, urinary tract infection, vibrio infections, yaws, yersinia infections, Yersinia pestis plague, zoonoses and zygomycosis.

11. The method of claim 1, wherein the pathogenic microorganism is a fungi, and the medical condition is a fungal infection selected from one or more of endemic fungal infections, opportunistic fungal infections, histoplasmosis histoplasma associated with capsulatum, coccidioidomycosis associated with *coccidioides immitis*, blastomycosis *blastomyces* associated with *dermatitidis*, paracoccidioidomycosis *paracoccidioides* associated with *brasiliensis*, candidiasis associated with *candida* spp., aspergillosis associated with *aspergillus* spp., mucormycosis associated with *mucor* spp., infections associated with *absidia*, infections associated with *rhizopus* spp., and cryptococcosis associated with *Cryptococcus neoformans*.

12. The method of claim 1, wherein the antimicrobial is selected from one or more of mandelic acid, 2,4-dichlorobenzenemethanol, 4-[bis(ethylthio)methyl]-2-methoxyphenol, 4-epitetracycline, 4-hexylresorcinol, 5, 12-dihydro-5, 7, 12, 14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammoniumsulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, avermycin, azanidazole, azidamfenicol, azidocillin, azithromycin, azlocillin, aztreonam, bacampicillin, bacitracin, bacitracin zmc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefmenoxime, cefmetazole, cefinetazole sodium, cefminox, cefminox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibrompropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin magnesium, flucloxacillin sodium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin cla, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin AS, leucomycin A6, leucomycin A7, leucomycin A8, leucomycin A9, levofloxacin, lincomycin, lincomycin hydrochloride, linezolid, liranaftate, 1-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin c, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin a, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, omidazole, orthophenylphenol, oxacillin, oxacillinsodium, oxiconazole, oxiconazole nitrate, oxoferin, oxolinic acid, oxychlorosene, oxytetracycline, oxytetracycline calcium, oxytetracycline hydrochloride, pampenem, paromomycm, paromomycm sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium-tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin Bl, polynoxylin, povidone-iodine, propamidin, propenidazole, propicillin, propicillin potassium, propionic acid, prothionamide, protiofate, pyrazinamide, pyrimethamine, pyridomycin, pyrithion, pyrrolnitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin b, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarb ami de, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatol ami de, sulfatriazin, sulfi somi dine, sulfi soxazole, sulfisoxazole acetyl, sulfonamides, sultamicillin, sultamicillin tosilate, tacrolimus, talampicillin 15 hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, 20 thiomersal, thiram, thymol, tibezonium iodide, ticarcillin, ticarcillin-clavulanic acid mixture, ticarcillin disodium, ticarcillin monosodium, tilbroquinol, tilmicosin, tinidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibomol and zinc undecylenate.

13. The method of claim 1 wherein the antimicrobial is selected from one or more of polyenes, amphotericin B, liposomal amphotericin, nystatin, and pimaricin; azoles, fluconazole, itraconazole, ketoconazole, itraconazole, voriconazole, posaconazole, anidulafungin, caspofungin, micafungin, allylamines, naftifine, binafine, amorolfine, 5-fluorocytosine, amoxicillin, amoxicillin sodium, amoxicillin trihydrate, amoxicillin-potassium clavulanate combination, aztreonam, azithromycin, azlocillin, clofazimine, cloxacillin, cloxacillin sodium, dicloxacillin, cefdinir, cefditoren, cefditoren pivoxil, cefepime, cefepime hydrochloride, colistin, colistin sodium methanesulfonate, colistin sulfate, clarithromycin, cefprozil, cefaclor, cefuroxime, cefuroxime axetil, cefuroxime sodium, dicloxacillin sodium, amikacin, amikacin sulfate, flucloxacillin, flucloxacillin magnesium, flucloxacillin sodium, doxycycline, doxycycline hydrochloride, imipenem, levofloxacin, linezolid, minocycline, minocycline hydrochloride, mezlocillin, mezlocillin sodium, nafcillin, nafcillin sodium, oxacillin, piperacillin, penicillin G, ciprofloxacin, ciprofloxacin hydrochloride, erythromycin, sulfisoxazole, sulfisoxazole acetyl, sulfamethoxazole, sulfamethoxazol-trimethoprim, tazobactam, tazobactam sodium, tetracycline, tobramycin, tobramycin sulfate, ticarcillin, ticarcillin-clavulanic acid mixture, ticarcillin disodium, ticarcillin monosodium, gentamicin, vancomycin and methicillin.

14. A method of treating a subject having a medical condition associated with a pathogenic microorganism in which an antimicrobial resistance has been uncovered following treating said subject with said antimicrobial agent, the method comprising:
   (i) administering to said subject, following a treatment with said antimicrobial agent and uncovering said antimicrobial resistance, a re-sensitizing effective amount of nitric oxide;
   (ii) administering to said subject a therapeutically effective amount of said antimicrobial agent,
wherein said antimicrobial agent is other than said nitric oxide and said re-sensitizing effective amount of nitric oxide is lower than a therapeutically effective amount of nitric oxide with respect to said microorganism.

15. A method for sensitizing or re-sensitizing a microorganism to an antimicrobial agent, comprising:
   (i) contacting said microorganism with a sensitizing or re-sensitizing effective amount of nitric oxide; and
   (ii) contacting said microorganism with a therapeutically effective amount of said antimicrobial agent, wherein said antimicrobial agent is other than said nitric oxide and said sensitizing or re-sensitizing effective amount being lower than a therapeutically effective amount of said nitric oxide with respect to said pathogenic microorganism; and
wherein said pathogenic microorganism exhibits a resistance to said antimicrobial agent prior to said administering said potentiating effective amount of nitric oxide.

16. The method of claim 15, wherein said sensitizing or re-sensitizing effective amount is lower than 1 MIC unit of nitric oxide with respect to said pathogenic microorganism.

17. The method of claim 15, wherein contacting said microorganism with said nitric oxide comprises administering to a subject having a medical condition associated with said microorganism, said sensitizing or re-sensitizing effective amount of said nitric oxide; and wherein contacting said microorganism with said therapeutically effective amount of said antimicrobial agent comprises administering to said subject said antimicrobial agent.

18. The method of claim 15, wherein said antimicrobial agent is inactive when used against said pathogenic microorganism.

* * * * *

UNITED STATES PATENT AND TRADEMARK OFFICE
CERTIFICATE OF CORRECTION

PATENT NO. : 11,890,421 B2
APPLICATION NO. : 16/787921
DATED : February 6, 2024
INVENTOR(S) : Yossef Av-Gay, David Greenberg and Asher Tal It is certified that error appears in the above-identified patent and that said Letters Patent is hereby corrected as shown below:

In the Claims

Column 65, Claim 12, Lines 23-24: please delete "sulfacarb ami de" and insert --sulfacarbamide--;
    Line 33: please delete "sulfatol ami de" and insert -- sulfatolamide-- and delete "sulfi somi dine" and insert --sulfisomidine--;
    Lines 33-34: delete "sulfi soxazole" and insert --sulfisoxazole--.

Signed and Sealed this
Twenty-sixth Day of March, 2024

Katherine Kelly Vidal
*Director of the United States Patent and Trademark Office*